United States Patent [19]

Quax et al.

[11] Patent Number: 5,376,536
[45] Date of Patent: Dec. 27, 1994

[54] GLUCOSE ISOMERASE ENZYMES AND THEIR USE

[75] Inventors: Wilhemus J. Quax, VB Voorschoten; Rudolf G. M. Luiten, KR Leiden; Paul W. Schuurhuizen, NT Delft, all of Netherlands; Nadir Mrabet, Hoeilaart, Belgium

[73] Assignees: Gist-Brocades, N.V., Delft, Netherlands; Plant Genetic Systems, N.V., Brussels, Belgium

[21] Appl. No.: 640,476

[22] Filed: Jan. 10, 1991

Related U.S. Application Data

[63] Continuation-in-part of Ser. No. 466,670, Jan. 17, 1990, abandoned, and a continuation-in-part of Ser. No. 398,519, Aug. 25, 1989, abandoned, and a continuation-in-part of Ser. No. 398,706, Aug. 25, 1989, Pat. No. 5,290,690.

[30] Foreign Application Priority Data

Jul. 15, 1988 [EP] European Pat. Off. ........ 88201539.9
Nov. 4, 1988 [EP] European Pat. Off. ........ 88402789.7
Jul. 17, 1989 [WO] WIPO ................ PCT/EP89/00838
Jul. 17, 1989 [WO] WIPO ................ PCT/EP89/00839

[51] Int. Cl.$^5$ .......................... C12N 9/00; C12N 9/92; C12N 11/02; C12N 15/61
[52] U.S. Cl. ................... 435/100; 435/234; 435/827; 435/172.3; 536/23.2
[58] Field of Search .................. 435/234, 827, 172.3, 435/69.1, 100; 536/4.1, 125, 23.1, 23.2

[56] References Cited

U.S. PATENT DOCUMENTS 4,567,142 1/1986 Lloyd ...................... 435/94

FOREIGN PATENT DOCUMENTS 0275202 7/1988 European Pat. Off. .

OTHER PUBLICATIONS

Mozhaev, V. V. et al., "Structure-stability relationships in proteins: new approaches to stabilizing enzymes." *Enzyme Microb. Technol.* 6:50–59 (1984).

Argos, R. et al. "Xylose isomerase from Actinoplanes missouriensis." *Nucleic Acids Res.* 17:7515 (1989).
Allenza, Paul et al. *ASM Abstracts* 88(0)262 (May 1988).
Chen, *Process Biochemistry* (Jun./Jul., 1980) 15:30–35.
Chen, *Process Biochemistry* (Aug./Sep., 1980) 15:36–41.
Svendsen, *Carlsberg Research Communications* (1976) 41(5):237–291.
Wilhelm et al., *Nucleic Acids Research* (1985) 13(15):5717–5722.
Wigley et al., *Biochem. Biophys. Res. Comm.* (1987) 149(3):927–929.
Mueller, *J. Biol. Chem.* (1988) 263 (12):5634–5639.
Beyer et al., *J. Biol. Chem.* (1987) 262(23):11182–11187.
Argos et al., *Biochem.* (1979) 18(25):5698–5703.
Baldwin et al., *Protein Eng.* (1987) Alan R. Liss, Inc., pp. 127–148.
Van Belle et al., *Biol. Abstracts* (1988) 85(7):AB-64 (abstract No. 64692).
Beyer et al., *Chem. Abstracts* (1989) 110(1):345 (abstract No. 3695f).
Rey et al., *Biol. Abstracts* (1989) 87(6):AB-929 (abstract No. 63577).
Hart et al., *Biochem. Biophys. Res. Comm.* (1987) 146(1):346–353.
Shaw et al., *Protein Eng.* (1987) 1(3):267 (abstract no. 154).
Querol et al., *Enzyme Microb. Technol.* (1987) 9:238–244.
R. Amore and C. P. Hollenberg, Xylose Isomerase from Actinoplanes Missouriensis; Primary Structure of the Gene and the Protein, vol. 17, No. 18, 1989, Nucleic Acids Research.

*Primary Examiner*—Robert A. Wax
*Assistant Examiner*—Dian C. Jacobson
*Attorney, Agent, or Firm*—Morrison & Foerster

[57] ABSTRACT

New mutant glucose isomerases are provided exhibiting improved properties under application conditions. These glucose isomerases are obtained by expression of a gene encoding said enzyme, having an amino acid sequence which differs at least in one amino acid from the wildtype glucose isomerase. Preferred mutant enzymes are those derived from *Actinoplanes missouriensis* glucose isomerase.

8 Claims, 33 Drawing Sheets

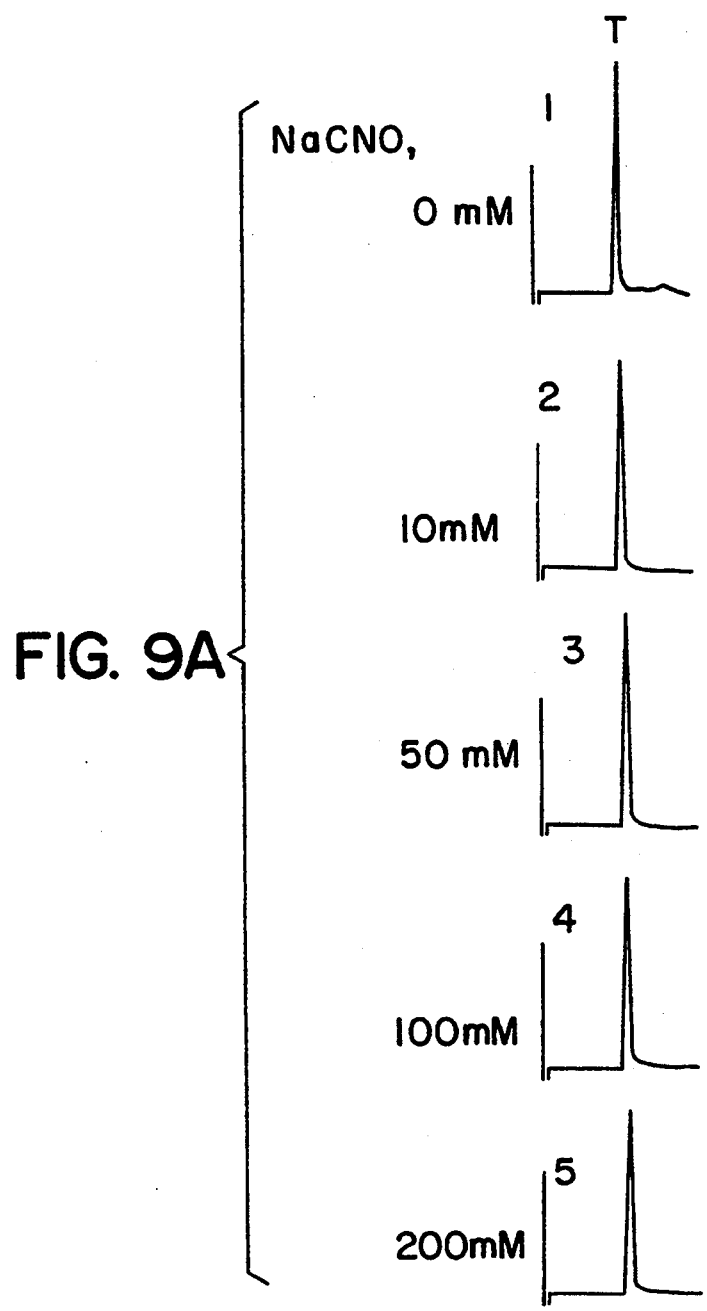

FIG. 9B

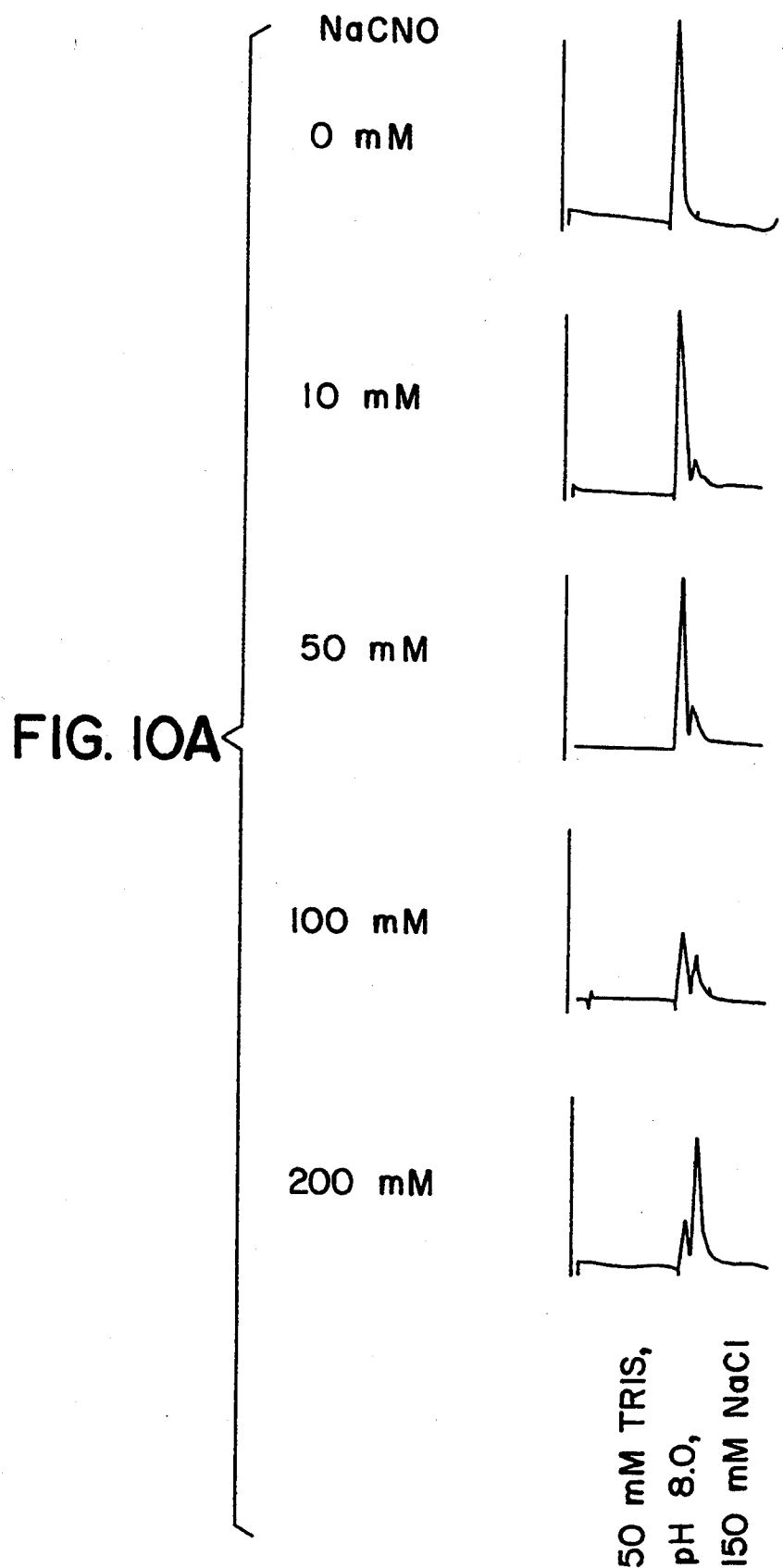

TETRAMER →

DIMER → {

CONTROL | 0 mM | 10 mM | 50 mM | 100 mM | 200 mM | CONTROL

---NaCNO---

TETRAMER →

FIG. 10B

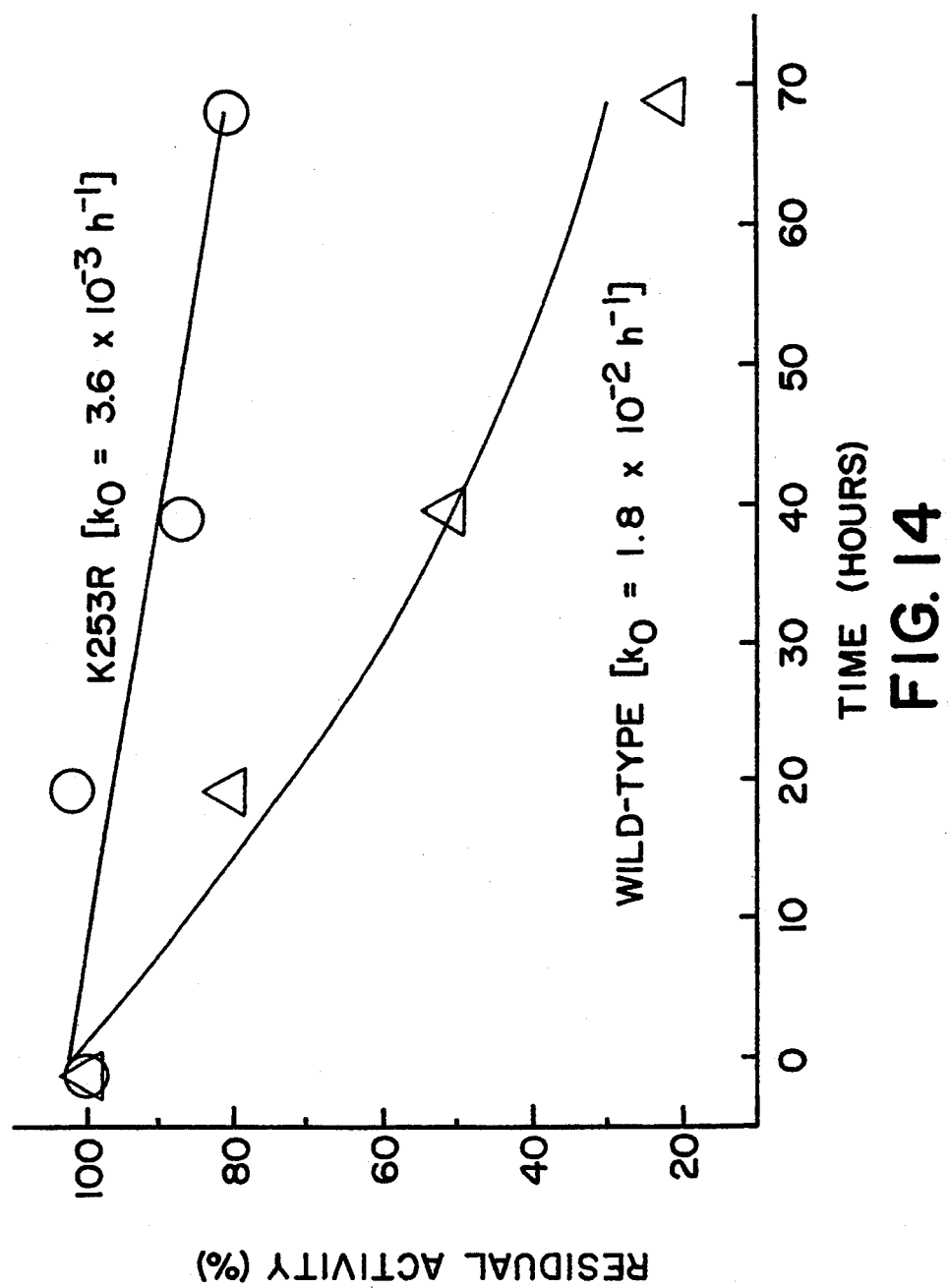

```
         10        20        30        40        50        60
AATTCACCTCGAAAGCAAGCTGATAAACCGATACAATTAAAGGCTCCTTTTGGAGCCTTT 70        80        90       100       110       120
TTTTTTGGAGATTTTCAACGTGAAAAAATTATTATTCGCAATTCCAAGCTAATTCACCTC 130       140       150       160       170       180
GAAAGCAAGCTGATAAACCGATACAATTAAAGGCTCCTTTTGGAGCCTTTTTTTTTGGAG 190       200       210       220       230       240
ATTTTCAACGTGAAAAAATTATTATTCGCAATTCCAAGCTCTGCCTCGCGCGTTTCGGTG 250       260       270       280       290       300
ATGACGGTGAAAACCTCTGACACATGCAGCTCCCGGAGACGGTCACAGCTTGTCTGTAAG 310       320       330       340       350       360
CGGATGCAGATCACGCGCCCTGTAGCGGCGCATTAAGCGCGGCGGGTGTGGTGGTTACGC 370       380       390       400       410       420
GCAGCGTGACCGCTACACTTGCCAGCGCCCTAGCGCCCGCTCCTTTCGCTTTCTTCCCTT 430       440       450       460       470       480
CCTTTCTCGCCACGTTCGCCGGCTTTCCCCGTCAAGCTCTAAATCGGGGCTCCCTTTAG 490       500       510       520       530       540
GGTTCCGATTTAGTGCTTTACGGCACCTCGACCCCAAAAAACTTGATTAGGGTGATGGTT 550       560       570       580       590       600
CACGTAGTGGGCCATCGCCCTGATAGACGGTTTTTCGCCCTTTGACGTTGGAGTCCACGT 610       620       630       640       650       660
TCTTTAATAGTGGACTCTTGTTCCAAACTGGAACAACACTCAACCCTATCTCGGTCTATT 670       680       690       700       710       720
CTTTGATTTATAAGGGATTTTGCCGATTTCGGCCTATTGGTTAAAAAATGAGCTGATTT 730       740       750       760       770       780
AACAAAAATTTAACGCGAATTTTAACAAAATATTAACGTTTACAATTTGATCTGCGCTCG 790       800       810       820       830       840
GTCGTTCGGCTGCGGCGAGCGGTATCAGCTCACTCAAAGGCGGTAATACGGTTATCCACA 850       860       870       880       890       900
GAATCAGGGGATAACGCAGGAAAGAACATGTGAGCAAAAGGCCAGCAAAAGGCCAGGAAC 910       920       930       940       950       960
CGTAAAAAGGCCGCGTTGCTGGCGTTTTTCCATAGGCTCCGCCCCCCTGACGAGCATCAC 970       980       990      1000      1010      1020
AAAAATCGACGCTCAAGTCAGAGGTGGCGAAACCCGACAGGACTATAAAGATACCAGGCG 1030      1040      1050      1060      1070      1080
TTTCCCCCTGGAAGCTCCCTCGTGCGCTCTCCTGTTCCGACCCTGCCGCTTACCGGATAC
```

FIG. 15A-1

```
         1090      1100      1110      1120      1130      1140
CTGTCCGCCTTTCTCCCTTCGGGAAGCGTGGCGCTTTCTCATAGCTCACGCTGTAGGTAT 1150      1160      1170      1180      1190      1200
CTCAGTTCGGTGTAGGTCGTTCGCTCCAAGCTGGGCTGTGTGCACGAACCCCCCGTTCAG 1210      1220      1230      1240      1250      1260
CCCGACCGCTGCGCCTTATCCGGTAACTATCGTCTTGAGTCCAACCCGGTAAGACACGAC 1270      1280      1290      1300      1310      1320
TTATCGCCACTGGCAGCAGCCACTGGTAACAGGATTAGCAGAGCGAGGTATGTAGGCGGT 1330      1340      1350      1360      1370      1380
GCTACAGAGTTCTTGAAGTGGTGGCCTAACTACGGCTACACTAGAAGGACAGTATTTGGT 1390      1400      1410      1420      1430      1440
ATCTGCGCTCTGCTGAAGCCAGTTACCTTCGGAAAAAGAGTTGGTAGCTCTTGATCCGGC 1450      1460      1470      1480      1490      1500
AAACAAACCACCGCTGGTAGCGGTGGTTTTTTTGTTTGCAAGCAGCAGATTACGCGCAGA 1510      1520      1530      1540      1550      1560
AAAAAAGGATCTCAAGAAGATCCTTTGATCTTTTCTACGGGGTCTGACGCTCAGTGGAAC 1570      1580      1590      1600      1610      1620
GAAAACTCACGTTAAGGGATTTTGGTCATGAGATTATCAAAAAGGATCTTCACCTAGATC 1630      1640      1650      1660      1670      1680
CTTTTAAATTAAAAATGAAGTTTTAAATCAATCTAAAGTATATATGAGTAAACTTGGTCT 1690      1700      1710      1720      1730      1740
GACAGTTACCAATGCTTAATCAGTGAGGCACCTATCTCAGCGATCTGTCTATTTCGTTCA 1750      1760      1770      1780      1790      1800
TCCATAGTTGCCTGACTCCCCGTCGTGTAGATAACTACGATACGGGAGGGCTTACCATCT 1810      1820      1830      1840      1850      1860
GGCCCCAGTGCTGCAATGATACCGCGAGACCCACGCTCACCGGCTCCAGATTTATCAGCA 1870      1880      1890      1900      1910      1920
ATAAACCAGCCAGCCGGAAGGGCCGAGCGCAGAAGTGGTCCTGCAACTTTATCCGCCTCC 1930      1940      1950      1960      1970      1980
ATCCAGTCTATTAATTGTTGCCGGGAAGCTAGAGTAAGTAGTTCGCCAGTTAATAGTTTG 1990      2000      2010      2020      2030      2040
CGCAACGTTGTTGCCATTGCTGCAGGCATCGTGGTGTCACGCTCGTCGTTTGGTATGGCT 2050      2060      2070      2080      2090      2100
TCATTCAGCTCCGGTTCCCAACGATCAAGGCGAGTTACATGATCCCCCATGTTGTGCAAA 2110      2120      2130      2140      2150      2160
AAAGCGGTTAGCTCCTTCGGTCCTCCGATCGTTGTCAGAAGTAAGTTGGCCGCAGTGTTA
```

FIG. 15A-2

```
      2170      2180      2190      2200      2210      2220
TCACTCATGGTTATGGCAGCACTGCATAATTCTCTTACTGTCATGCCATCCGTAAGATGC 2230      2240      2250      2260      2270      2280
TTTTCTGTGACTGGTGAGTACTCAACCAAGTCATTCTGAGAATAGTGTATGCGGCGACCG 2290      2300      2310      2320      2330      2340
AGTTGCTCTTGCCCGGCGTCAACACGGGATAATACCGCGCCACATAGCAGAACTTTAAAA 2350      2360      2370      2380      2390      2400
GTGCTCATCATTGGAAAACGTTCTTCGGGGCGAAAACTCTCAAGGATCTTACCGCTGTTG 2410      2420      2430      2440      2450      2460
AGATCCAGTTCGATGTAACCCACTCGTGCACCCAACTGATCTTCAGCATCTTTTACTTTC 2470      2480      2490      2500      2510      2520
ACCAGCGTTTCTGGGTGAGCAAAAACAGGAAGGCAAAATGCCGCAAAAAAGGGAATAAGG 2530      2540      2550      2560      2570      2580
GCGACACGGAAATGTTGAATACTCATACTCTTCCTTTTTCAATATTATTGAAGCAGACAG 2590      2600      2610      2620      2630      2640
TTTTATTGTTCATGATGATATATTTTTATCTTGTGCAATGTAACATCAGAGATTTTGAGA 2650      2660      2670      2680      2690      2700
CACAACGTGGCTTTGTTGAATAAATCGAACTTTTGCTGAGTTGACTCCCCGCGCGCGATG 2710      2720      2730      2740      2750      2760
GGTCGAATTTGCTTTCGAAAAAAAAGCCCGCTCATTAGGCGGGCTAAAAAAAAGCCCGCT 2770      2780      2790      2800      2810      2820
CATTAGGCGGGCTCGAATTTCTGCCATTCATCCGCTTATTATCACTTATTCAGGCGTAGC 2830      2840      2850      2860      2870      2880
AACCAGGCGTTTAAGGGCACCAATAACTGCCTTAAAAAAATTACGCCCCGCCCTGCCACT 2890      2900      2910      2920      2930      2940
CATCGCAGTACTGTTGTAATTCATTAAGCATTCTGCCGACATGGAAGCCATCACAGACGG 2950      2960      2970      2980      2990      3000
CATGATGAACCTGAATCGCCAGCGGCATCAGCACCTTGTCGCCTTGCGTATAATATTTGC 3010      3020      3030      3040      3050      3060
CCATAGTGAAAACGGGGGCGAAGAAGTTGTCCATATTCGCCACGTTTAAATCAAAACTGG 3070      3080      3090      3100      3110      3120
TGAAACTCACCCAGGGATTGGCTGAGACGAAAAACATATTCTCAATAAACCCTTTAGGGA 3130      3140      3150      3160      3170      3180
AATAGGCCAGGTTTTCACCGTAACACGCCACATCTTGCGAATATATGTGTAGAAACTGCC 3190      3200      3210      3220      3230      3240
GGAAATCGTCGTGGTATTCACTCCAGAGCGATGAAAACGTTTCAGTTTGCTCATGGAAAA
```

FIG. 15A-3

```
       3250      3260      3270      3280      3290      3300
CGGTGTAACAAGGGTGAACACTATCCCATATCACCAGCTCACCGTCTTTCATTGCCATAC 3310      3320      3330      3340      3350      3360
GAAATTCCGGATGAGCATTCATCAGGCGGGCAAGAATGTGAATAAAGGCCGGATAAAACT 3370      3380      3390      3400      3410      3420
TGTGCTTATTTTTCTTTACGGTCTTTAAAAAGGCCGTAATATCCAGCTAAACGGTCTGGT 3430      3440      3450      3460      3470      3480
TATAGGTACATTGAGCAACTGACTGAAATGCCTCAAAATGTTCTTTACGATGCCATTGGG 3490      3500      3510      3520      3530      3540
ATATATCAACGGTGGTATATCCAGTGATTTTTTTCTCCATTTTAGCTTCCTTAGCTCCTG 3550      3560      3570      3580      3590      3600
AAAATCTCGATAACTCAAAAAATACGCCCGGTAGTGATCTTATTTCATTATGGTGAAAGT 3610      3620      3630      3640      3650      3660
TGGAACCTCTTACGTGCCGATCAACGTCTCATTTTCGCCAAAAGTTGGCCCAGGGCTTCC 3670      3680      3690      3700      3710      3720
CGGTATCAACAGGGACACCAGGATTTATTTATTCTGCGAAGTGATCTTCCGTCACAGGTA 3730      3740      3750      3760      3770      3780
TTTATTCGAAGACGAAAGGGCATCGCGCGCGGGAATTCCCGGGGATCCGTCGACCTGCA 3790      3800
GCCAAGCTTGGTCTAGAGGTCGA
```

FIG. 15A-4

```
          10        20        30        40        50        60
GAATTCCGCAAGGGATAAATATCTAACACCGTGCGTGTTGACTATTTTACCTCTGGCGGT 70        80        90       100       110       120
GATAATGGTTGCATGTACTAAGGAGGTTGTATGGAACAACGCATAACCCTGAAAGATAGC

TTGGGATCC
```

Figure 15C

```
          10        20        30        40        50        60
GAATTCGAGCTCGAGCTTACTCCCCATCCCCCTGTTGACAATTAATCATCGGCTCGTATA 70        80        90       100
ATGTGTGGAATTGTGAGCGGATAACAATTTCACACAGGAAACAGGATCC
```

FIG. 15B

```
                    .         30         .         .         60
        GTGTCTGTCCAGGCCACACGCGAAGACAAGTTCTCCTTCGGTCTCTGGACCGTTGGATGG
         M  S  V  Q  A  T  R  E  D  K  F  S  F  G  L  W  T  V  G  W

.         90         .         .        120
        CAGGCTCGTGACGCGTTCGGTGACGCCACGCGTACGGCACTCGACCCGGTCGAGGCCGTG
         Q  A  R  D  A  F  G  D  A  T  R  T  A  L  D  P  V  E  A  V

.        150         .         .        180
        CACAAGCTCGCTGAGATCGGCGCCTACGGCATCACGTTCCACGACGACGACCTGGTGCCC
         H  K  L  A  E  I  G  A  Y  G  I  T  F  H  D  D  D  L  V  P

.        210         .         .        240
        TTCGGCTCGGACGCCCAGACCCGCGACGGCATCATCGCGGGCTTCAAGAAGGCGCTCGAC
         F  G  S  D  A  Q  T  R  D  G  I  I  A  G  F  K  K  A  L  D

.        270         .         .        300
        GAGACCGGCCTGATCGTCCCGATGGTGACCACCAACCTCTTCACCCACCCGGTGTTCAAG
         E  T  G  L  I  V  P  M  V  T  T  N  L  F  T  H  P  V  F  K

.        330         .         .        360
        GACGGCGGCTTCACCAGCAACGACCGTTCCGTGCGGCGCTACGCGATCCGCAAGGTGCTG
         D  G  G  F  T  S  N  D  R  S  V  R  R  Y  A  I  R  K  V  L

.        390         .         .        420
        CGCCAGATGGACCTCGGCGCCGAGCTGGGCGCGAAGACGCTCGTCCTCTGGGGCGGCCGC
         R  Q  M  D  L  G  A  E  L  G  A  K  T  L  V  L  W  G  G  R

.        450         .         .        480
        GAGGGCGCCGAGTACGACTCGGCCAAGGACGTCAGCGCCGCCCTCGACCGCTACCGCGAG
         E  G  A  E  Y  D  S  A  K  D  V  S  A  A  L  D  R  Y  R  E

.        510         .         .        540
        GCGCTCAACCTGCTCGCGCAGTACTCCGAGGACCGCGGGTACGGCCTGCGCTTCGCCATC
         A  L  N  L  L  A  Q  Y  S  E  D  R  G  Y  G  L  R  F  A  I

.        570         .         .        600
        GAGCCGAAGCCGAACGAGCCCCGCGGCGACATCCTGCTCCCGACCGCCGGCCACGCCATC
         E  P  K  P  N  E  P  R  G  D  I  L  L  P  T  A  G  H  A  I

.        630         .         .        660
        GCGTTCGTGCAGGAGCTGGAGCGTCCCGAGCTCTTCGGCATCAACCCGGAGACCGGGCAC
         A  F  V  Q  E  L  E  R  P  E  L  F  G  I  N  P  E  T  G  H

.        690         .         .        720
        GAGCAGATGTCGAACCTCAACTTCACCCAGGGCATCGCCCAGGCGCTGTGGCACAAGAAG
         E  Q  M  S  N  L  N  F  T  Q  G  I  A  Q  A  L  W  H  K  K

.        750         .         .        780
        CTGTTCCACATCGACCTGAACGGTCAGCACGGCCCGAAGTTCGACCAGGACCTGGTCTTC
         L  F  H  I  D  L  N  G  Q  H  G  P  K  F  D  Q  D  L  V  F
```

FIG. 16A

```
                          810                    840
GGCCACGGTGACCTGCTCAACGCGTTCTCGCTGGTCGACCTCCTGGAGAACGGCCCGGAC
 G  H  G  D  L  L  N  A  F  S  L  V  D  L  L  E  N  G  P  D 870                    900
GGCGCCCCGGCGTACGACGGACCCCGTCACTTCGACTACAAGCCGTCCCGTACCGAGGAC
 G  A  P  A  Y  D  G  P  R  H  F  D  Y  K  P  S  R  T  E  D 930                    960
TACGACGGCGTCTGGGAGTCGGCGAAGGCCAACATCCGGATGTACCTGCTGCTCAAGGAG
 Y  D  G  V  W  E  S  A  K  A  N  I  R  M  Y  L  L  L  K  E 990                   1020
CGGGCCAAGGCGTTCCGCGCCGACCCCGAGGTGCAGGAGGCGCTCGCCGCCAGCAAGGTC
 R  A  K  A  F  R  A  D  P  E  V  Q  E  A  L  A  A  S  K  V 1050                   1080
GCGGAGCTGAAGACCCCGACCCTGAACCCGGGCGAGGGATACGCCGAGCTGCTCGCCGAC
 A  E  L  K  T  P  T  L  N  P  G  E  G  Y  A  E  L  L  A  D 1110                   1140
CGCAGCGCGTTCGAGGACTACGACGCCGACGCCGTGGGCGCCAAGGGCTTCGGCTTCGTC
 R  S  A  F  E  D  Y  D  A  D  A  V  G  A  K  G  F  G  F  V

1170
AAGCTGAACCAGCTCGCGATCGAGCACCTGCTCGGAGCCCGC
 K  L  N  Q  L  A  I  E  H  L  L  G  A  R
```

FIG. 16B

```
                          .         30         .         60
         ATGAGCTTCCAGCCCACCCCGGAGGACAGGTTCACCTTCGGTCTGTGGACCGTCGGCTGG
          M  S  F  Q  P  T  P  E  D  R  F  T  F  G  L  W  T  V  G  W

.         90         .        120
         CAGGGAAGGGACCCGTTCGGCGACGCCACCCGCCCGGCCCTCGACCCGGTCGAGACGGTG
          Q  G  R  D  P  F  G  D  A  T  R  P  A  L  D  P  V  E  T  V

.        150         .        180
         CAGCGCCTGGCCGAGCTGGGCGCCTACGGAGTGACCTTCCACGACGACGACCTGATCCCC
          Q  R  L  A  E  L  G  A  Y  G  V  T  F  H  D  D  D  L  I  P

.        210         .        240
         TTCGGGTCCTCCGACACCGAGCGCGAGTCGCACATCAAGCGCTTCCGCCAGGCCCTGGAC
          F  G  S  S  D  T  E  R  E  S  H  I  K  R  F  R  Q  A  L  D

.        270         .        300
         GCCACCGGCATGACGGTGCCCATGGCCACCACCAACCTCTTCACCCACCCGGTCTTCAAG
          A  T  G  M  T  V  P  M  A  T  T  N  L  F  T  H  P  V  F  K

.        330         .        360
         GACGGCGGCTTCACCGCCAACGACCGCGACGTACGCCGGTACGCGCTGCGCAAGACGATC
          D  G  G  F  T  A  N  D  R  D  V  R  R  Y  A  L  R  K  T  I

.        390         .        420
         GGCAACATCGACCTGGCGGCCGAACTGGGTGCCAAGACGTATGTCGCCTGGGGCGGCCGT
          G  N  I  D  L  A  A  E  L  G  A  K  T  Y  V  A  W  G  G  R

.        450         .        480
         GAGGGCGCCGAGTCCGGTGGCGCCAAGGACGTGCGCGACGCCCTCGACCGCATGAAGGAG
          E  G  A  E  S  G  G  A  K  D  V  R  D  A  L  D  R  M  K  E

.        510         .        540
         GCGTTCGACCTCCTCGGCGAGTACGTCACCGCCCAGGGCTACGACCTCCGCTTCGCCATC
          A  F  D  L  L  G  E  Y  V  T  A  Q  G  Y  D  L  R  F  A  I

.        570         .        600
         GAGCCCAAGCCCAACGAGCCCCGCGGCGACATCCTGCTGCCCACCGTCGGCCACGCCCTG
          E  P  K  P  N  E  P  R  G  D  I  L  L  P  T  V  G  H  A  L

.        630         .        660
         GCCTTCATCGAGCGCCTGGAGCGCCCGGAGCTGTACGGCGTCAACCCGGAGGTCGGCCAC
          A  F  I  E  R  L  E  R  P  E  L  Y  G  V  N  P  E  V  G  H

.        690         .        720
         GAGCAGATGGCCGGCCTGAACTTCCCGCACGGCATCGCGCAGGCCCTGTGGGCGGGCAAG
          E  Q  M  A  G  L  N  F  P  H  G  I  A  Q  A  L  W  A  G  K

.        750         .        780
         CTCTTCCACATCGACCTCAACGGCCAGTCCGGCATCAAGTACGACCAGGACCTGCGGTTC
          L  F  H  I  D  L  N  G  Q  S  G  I  K  Y  D  Q  D  L  R  F
```

FIG. 19A

```
                    .         810         .         .        840
         GGCGCCGGCGACCTGCGGGCGGCGTTCTGGCTGGTCGACCTCCTGGAGACCGCCGGTTAC
          G  A  G  D  L  R  A  A  F  W  L  V  D  L  L  E  T  A  G  Y

.         870         .         .        900
         GAGGGCCCGCGGCACTTCGACTTCAAGCCGCCGCGGACCGAGGACTTCGACGGCGTGTGG
          E  G  P  R  H  F  D  F  K  P  P  R  T  E  D  F  D  G  V  W

.         930         .         .        960
         GCCTCGGCCGCGGGCTGCATGCGCAACTACCTGATCCTCAAGGACCGTGCGGCCGCCTTC
          A  S  A  A  G  C  M  R  N  Y  L  I  L  K  D  R  A  A  A  F

.         990         .         .       1020
         CGTGCCGACCCGGAGGTGCAGGAGGCGCTGCGTGCCGCGCGTCTGGACCAGCTGGCCCAG
          R  A  D  P  E  V  Q  E  A  L  R  A  A  R  L  D  Q  L  A  Q

.        1050         .         .       1080
         CCGACCGCGGCCGACGGCCTTGACGCCCTGCTCGCCGACCGCGCGGCGTTCGAGGACTTC
          P  T  A  A  D  G  L  D  A  L  L  A  D  R  A  A  F  E  D  F

.        1110         .         .       1140
         GACGTCGATGCCGCCGCGGCGCGCGGTATGGCGTTCGAGCACCTCGACCAGCTGGCGATG
          D  V  D  A  A  A  A  R  G  M  A  F  E  H  L  D  Q  L  A  M

.           .
         GACCACCTGCTGGGCGCGCGCGGC
          D  H  L  L  G  A  R  G
```

```
              10        20        30        40        50
Aml  MSVQATREDKFSFGLWTVGWQARDAFGDATRTALDPVEAVHKLAEIGAYG
Amp      L      PD                                    
Act            PPA    H              TGA P           L
Smu      F     PP     R              G  P V          L
Svn      F     PP     T              G  P            L
Svr    NY      PP     T              G  P          S L
Sth      Y     PP     R              G  P            L
                                      A              
                                     GT 60        70        80        90       100
Aml  ITFHDDDLVPFGSDAQTRDGIIAGFKKALDETGLIVPMVTTNLFTHPVFK
Amp    V          A    V
Act         N   DATEAE EK LGD     KD
Smu         V   SDTE   ESH KR  A  A   MT   A       S
Svn         V   SDTE   ESH KR  A  A   MT   A
Svr         V   SDTE   ESH KR  A  A   MK   A
Sth             AAEDE  EAHVKR  A  A   MT   A 110       120       130       140       150
Aml  DGGFTSNDRSVRRYAIRKVLRQMDLGAELGAKTLVLWGGREGAEYDSAKD
Amp         I F LA        A   M  E F M           S  GS
Act                                                 SGG
Smu      A   D    TIGNIH   A       Y A              SGG
Svn      A   D    TI NIH   A     SV Y A             SGA
Svr      A   D    TI NIH  AV       R A              SGA
Sth      A   D    TI NIH  AV
```

```
                   160              170              180              190           200
       Ami  V S A A L D R Y R E A L N L L A Q Y S E D R G Y G L R F A I E P K P N E P R G D I L L P T A G H A I
       Amp                                            Q                                               G L
       Art  L A       G V D T A G                     I K K           N         I L                   V L L
       Smu  R D       M K   F D     G E               V T A Q         D         F                     V L L
       Svn  R D       M K   F D     G E               V T A Q         D                                 L L
       Svr  R D       M K   F D     G E               V T E Q         D K                              V L
       Sth  R         M K   F D     G E               V T S Q         D I                              V L 210              220              230              240           250
       Ami  A F V Q E L E R P E L F G I N P E T G H E Q M S N L N F T Q G I A Q A L W H K K L F H I D L N G Q H
       Amp       I E Q         H G D I V L                                         A E                     R
       Art       I E R                 Y V             A G           P H           A G                     S
       Smu       I E R                 Y V             A G           P H           A G                     S
       Svn       I E R                 Y V             A G           P H           A G                     S
       Svr       I E R                 Y               A G           P H           A G
       Sth       I E R                                 A G                         A G                     S 260              270              280              290           300
       Ami  G P K F D Q D L V F G H G D L L N A F S L V D L L E N G - P D G A P A Y D G P R H F D Y K P S R T E D
       Amp       I Y                         T S F T           F N G K T                                   D G
       Art       I Y           R A           R A W             T A - - - E - - -                           F P
       Smu       I Y           R A           R A W             S A - - - E - - -                           F P
       Svn       I Y           R A           R A W       G     R A - - - K - - -                           F P
       Svr       I Y           R A           R A W             S S - - - A - - -                           F P
       Sth       I Y           R             R A W

F I G.  21B
```

```
                     310              320              330              340          350
Ami   Y D G V W E S A K A N I R M Y L L L K E R A K A F R A D P E V Q E A L A A S K V A E L K T P T L N P
Amp                 F                   D                         A   E   D   R       G E T       A
Act                                                                   M K T G F       A Q       A A D
Smu   F           D         A G C M   N   I         L                 R   A R L D Q   A Q       A A D
Svn   F           A         E G C M   N   I         A                 R   A R L D Q   A Q       A E D
Svr   F           A         A G C M   N   I         A                         A R L D   A R       A A D
Sth   L           A         A G C M   N   I       S A             Q       R   R L D Q   A Q       A A D 360              370              380              390
Ami   G E G Y A E L L A D R S A F E D Y D A D A V G A K G F G - F V K L N Q L A I E H L L G A R -   - G -
Amp         T       D                         E     A A E R N   A -   I R                   D     S
Act         S A D   M N S A S   A G F       V     A A   R   M A -     E H   D               M D       G
Smu   L D - -           A                   F   V E A A   R A A W P   E R   D               M D
Svn   L E - -           T                   F           A A   R   M A -     E H   D               M D       G
Svr           Y D T F   V                                   A A   R   M A -                                 .
Sth   L A - -           .       .     .       .     .       .       .       .       .       .
```

GLUCOSE ISOMERASE ENZYMES AND THEIR USE

This application is a continuation-in-part of U.S. Ser. No. 466,670, filed Jan. 17, 1990, and of U.S. Ser. No. 398,519, filed Aug. 25, 1989, both now abandoned, and of U.S. Ser. No. 398,706, filed Aug. 25, 1989, now U.S. Pat. No. 5,290,690.

TECHNICAL FIELD

The present invention relates to novel glucose isomerases, which are suitable for application in industrial processes, especially the conversion of glucose into fructose. The invention relates also to the use of these novel enzymes in the production of fructose syrups, in particular, high fructose corn syrups.

BACKGROUND OF THE INVENTION

Glucose isomerase catalyzes the reversible isomerization of glucose to fructose. Fructose is nowadays commonly applied as sugar substitute due to its higher sweetness compared to, e.g., sucrose and glucose. Many microorganisms are known to produce glucose isomerase, see, for example, the review articles by Wen-Pin Chen in Process Biochemistry, 15 June/July (1980) 30–41 and August/September (1980) 36–41, in which a large number of microorganisms capable of producing glucose isomerase are listed.

Several microorganisms have been applied industrially. The Wen-Pin Chen reference describes culture conditions of the microorganisms and recovery and purification methods of the produced glucose isomerase.

The production of glucose isomerase, which is an intracellular enzyme, is relatively expensive. Special formulations have been developed to enable repeated and continuous use of the enzyme. By immobilizing the enzyme, usually in water-insoluble form, it can be used both in batch and continuous processes (e.g., packed-bed reactors). One of the major drawbacks of immobilization of glucose isomerase is the substantial decrease of specific activity, due to the presence of inert material. The situation becomes even worse during application, since glucose isomerase is inactivated at elevated temperatures. An irreversible loss of activity will be the result of the heat-induced deterioration.

Despite efforts to retain enzyme stability substantial activity loss is still encountered under normal application conditions. There is, therefore, a continuous need for new enzymes such as glucose isomerase with improved properties. Improved thermostability of glucose isomerase, for example, will allow to take advantage of the fact that the equilibrium of the isomerisation is shifted towards fructose at higher temperatures. Most glucose isomerases are applied at pH 7.5. However, fructose is not stable at this pH. Therefore, there is also a need for glucose isomerases which can be applied below pH 7.5.

Enzymes with improved properties can be developed or found in several ways, for example by classical screening methods, by chemical modification of existing proteins, or by using modern genetic and protein engineering techniques.

Screening for organisms or microorganisms that display the desired enzymatic activity, can be performed for example by isolating and purifying the enzyme from a microorganism or from a culture supernatant of such microorganisms, determining its biochemical properties and checking whether these biochemical properties meet the demands for application.

If the identified enzyme cannot be obtained from its natural producing organism, recombinant-DNA techniques may be used to isolate the gene encoding the enzyme, express the gene in another organism, isolate and purify the expressed enzyme and test whether it is suitable for the intended application.

Modification of existing enzymes can be achieved inter alia by chemical modification methods. See, for example, I. Svendsen, Carlsberg Res. Commun. 44 (1976), 237–291. In general, these methods are too unspecific in that they modify all accessible residues with common side chains, or they are dependent on the presence of suitable amino acids to be modified, and often they are unable to modify amino acids difficult to reach, unless the enzyme molecule is unfolded. Enzyme modification through mutagenesis of the encoding gene does not suffer from the aspecificities mentioned above, and therefore is thought to be superior. Mutagenesis can be achieved either by random mutagenesis or by site-directed mutagenesis.

Random mutagenesis, by treating whole microorganisms with chemical mutagens or with mutagenizing radiation, may of course result in modified enzymes, but then strong selection protocols are necessary to search for mutants having the desired properties. Higher probability of isolating desired mutant enzymes by random mutagenesis can be achieved by cloning the encoding gene, mutagenizing it in vitro or in vivo and expressing the encoded enzyme by recloning of the mutated gene in a suitable host cell. Also in this case suitable biological selection protocols must be available in order to select the desired mutant enzymes. These biological selection protocols do not specifically select enzymes suited for application in the fructose production.

Site-directed mutagenesis (SDM) is the most specific way of obtaining modified enzymes, enabling specific substitution of one or more amino acids by any other desired amino acid.

SUMMARY OF THE INVENTION

In one aspect of the present invention new mutant glucose isomerases are provided, obtained by expression of genes encoding said enzymes having amino acid sequences which differ in at least one amino acid from the corresponding wildtype glucose isomerases and exhibiting improved properties.

In another aspect of the invention a process is provided for the preparation of such new mutant glucose isomerases, based on modifications of the inter- and intra-molecular interactions of the corresponding wild-type enzymes.

In still another aspect of the invention a method is provided for selecting mutant enzymes with improved properties during industrial application.

BRIEF DESCRIPTION OF THE DRAWINGS

FIG. 9A. SEC-HPLC of EcoAmi(DSM) GI pretreated with cyanate at 25° C. in the absence of urea. Elution buffer was 50 mM Tris/HCl pH 8.0, 150 mM NaCl, 0.02% NaN$_3$.

FIG. 9B. Native PAGE of EcoAmi(DSM) GI treated with cyanate at 25° C. in the absence of urea.

FIG. 10A. SEC-HPLC of EcoAmi(DSM) GI pretreated with cyanate in the presence of 5M urea at 25° C.

FIG. 10B. Native PAGE of EcoAmi (DSM) GI treated with cyanate in the presence of 5M urea at 25° C.

FIG. 14. Kinetics of the glycation-induced inactivation of EcoAmi(DSM) GI mutant K253R at 60° C. in 12.5 mM Potassium phosphate, pH 7.7.

FIG. 15A. (SEQ ID NO:1) structure of pMa/c5-8. In the pMa type vector nucleotide 3409 is changed from A to G, while in the pMc type vector nucleotide 2238 is changed from G to C, creating amber stopcodons in the chloramphenicol acetyl transferase gene and the β-lactamase gene, respectively, rendering said genes inactive (P. Stanssens et al. (1987) in "Oligonucleotide-directed construction of mutations by the gapped duplex DNA method using the pMa/c phasmid vectors" Manual used at the EMBO laboratory course, "Directed Mutagenesis and Protein Engineering" held at the Max Planck Institut für Biochemie, Martinsried, July 4-18, 1987). The sequence displayed in the Figure is that of pMa5-8.

FIG. 15B. (SEQ ID NO:2) Lambda P$_R$ promoter sequence as present in the expression vector pMa/c5P$_R$ (replacing nucleotides 3754 to 3769 of pMa/c5-8).

FIG. 15C. (SEQ ID NO: 3) Tac promoter sequence as present on the expression vector pMa/c5T (replacing nucleotides 3754 to 3769 of pMa/c5-8).

FIG. 16. (SEQ ID NO: 4) and )SEQ ID NO: 5) The complete gene sequence and derived amino acid sequence of wildtype Actinoplanes missouriensis glucose isomerase.

FIG. 19 (SEQ ID NO:6) and (SEQ ID NO:7) The complete gene sequence and derived amino acid sequence of wildtype streptomyces murinus glucose isomerase.

FIG. 21. (SEQ ID NO:5), (SEQ ID NO:7), (SEQ ID NO:8), (SEQ ID NO:9), (SEQ ID NO:10), (SEQ ID NO:11), and (SEQ ID NO:12). Alignment of amino acid sequences of glucose isomerases from different sources. The complete sequence of the *Actinoplanes missouriensis* glucose isomerase is given whereas for the glucose isomerases from other sources only the amino acid residues differing from those of *Actinoplanes missouriensis* glucose isomerase are shown. The amino acid sequence of the Ampullariella glucose isomerase differs from that of the published sequence (Saari, J. Bacteriol., 169 (1987) 612) by one residue: Proline 177 in the published sequence was found to be an Arginine. The *Streptomyces thermovulgaris* sequence has only been established upto amino acid 346; undetermined residues are indicated by a block (•). A dash (-) indicates the absence of an amino acid residue at this position as compared to any of the other sequences. The different species are indicated by the following symbols:

Figure 1:
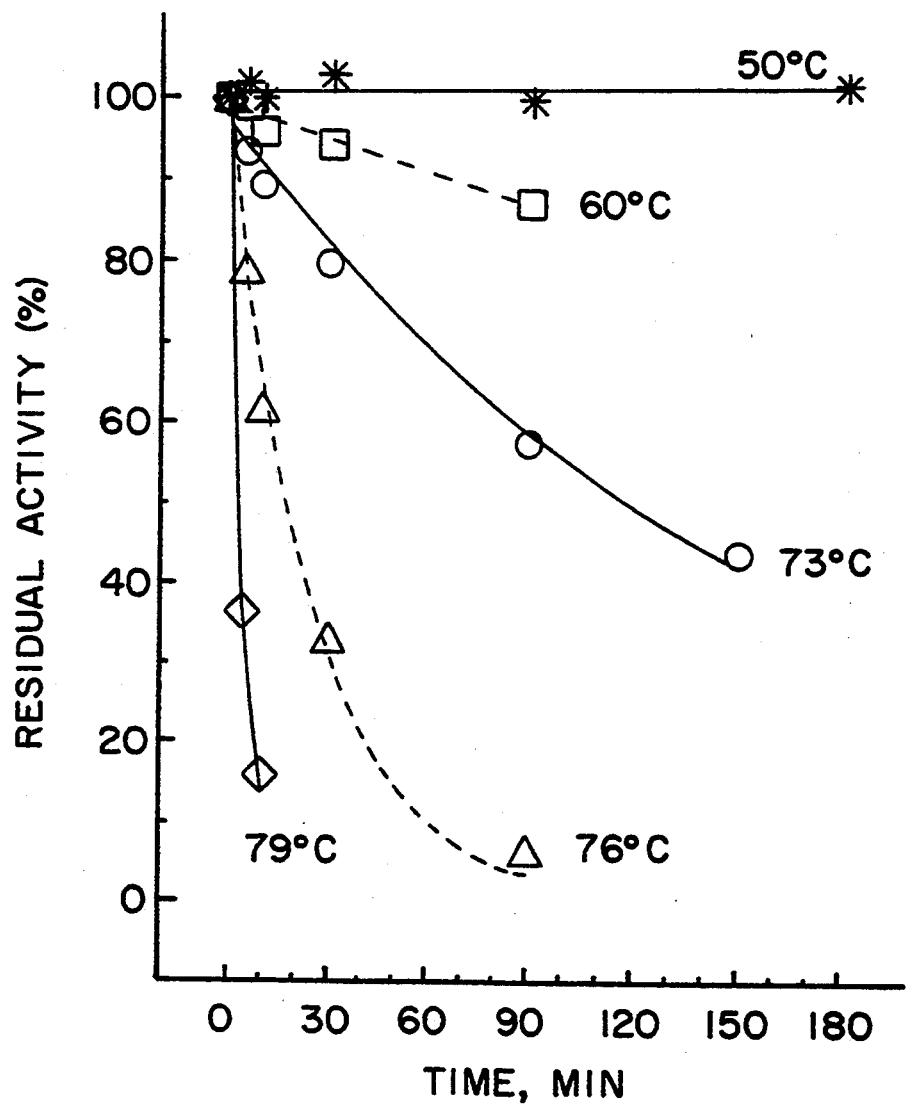
FIG. 1. Heat inactivation kinetics of metal-free glucose isomerase of EcoAmi(DSM) GI in 50 mM MOPS, pH 7.2 at 25° C. No metal was added.

Ami: *Actinoplanes missouriensis* DSM 4643
Amp: Ampullariella species ATCC 31351
Art: Agrobacter species
Smu: *Streptomyces murinus* DSM 40091
Svn: *Streptomyces Violaceoniger* CBS 409.73
Svr: *Streptomyces violaceroruber* LMG 7183
Sth: *Streptomyces thermovulgaris* DSM 40444

DETAILED DESCRIPTION OF THE INVENTION

According to this invention mutant glucose isomerase enzymes can be designed based on a careful examination of the structure of wildtype glucose isomerases, combined with careful biochemical investigation of the process leading to inactivation of the original glucose isomerases, under application conditions, followed by a rational modification of the wildtype gene sequence. Extensive investigation of designed mutants under industrial application conditions has resulted in the identification of mutants with improved properties.

By "improved properties" as used herein in connection with the present glucose isomerase enzymes, we mean higher conversion performance and/or improved stability, especially heat stability, relative to the corresponding wildtype enzymes. In addition, increased stability at different pH as such or in combination with enhanced thermostability is considered witch the term "improved properties".

The present invention is based on the discovery that the activity of certain enzymes is optimal when the enzyme is in multimeric (dimeric, trimeric, tetrameric, etc.) form and that said activity may decrease due to loss of interaction between the subunits. For example, it has been found that the enzymatic activity of *Actinopla-*

*nes missouriensis* glucose isomerase is unique to the tetrameric structure. This activity is substantially lost upon dissociation of the native tetramer structure into dimers.

Therefore, the present invention provides novel mutant glucose isomerases in which the interaction between subunits (monomers, dimers, etc.) is enhanced resulting in improved properties of the enzymes, especially under application conditions. The invention provides also methods for enhancing the interactions between glucose isomerase subunits.

According to a preferred embodiment the stabilization of the tetrameric structure of glucose isomerase is achieved by strengthening the interaction between the dimers in the tetramer.

A suitable method to improve the stability of the tetrameric structure is, for example, the introduction of ionic bridges. Electrostatic effects are well known to play a fundamental role in enzyme function and structures (see J. A. Matthew et al., CRC Critical Reviews in Biochemistry, 18 (1985) 91–197). They account, for example, for the pH dependence of enzyme catalysis since the optimum pH for a given protein is determined by the presence of ionizable groups surrounding the active site. Electrostatic interactions involved in hydrogen bonds and ionic (salt) bridges are important in stabilizing the overall protein structure (see A. J. Russell and A. R. Fersht, Nature 36 (1987) 496–500). According to the assumption that the dissociation of the glucose isomerase tetramer into dimers is mainly responsible for the enzyme denaturation, this process can be prevented by introducing, in the interfaces, additional stabilizing interactions such as supplementary salt bridges.

To introduce new salt bridges in a given protein, one possibility is to substitute two neighbouring residues into oppositely charged amino acids like, for example, Asp and Arg and then check, for example by energy map calculations, that an ionic interaction could be formed. This introduction of a new salt bridge requires two point mutations. Alternatively, one may create a salt bridge by substituting a residue close to an isolated charged amino acid, thus creating an ionic pair by a single point mutation.

Another suitable method to improve the stability of the tetrameric structure is the introduction of disulfide bridges. Disulfide bonds are a common feature of many extracellular proteins. The role of these cross-linkings is mainly to stabilize proteins, this effect being one of the best understood. It is commonly explained by a decrease of the entropy of the unfolded state, but several facts remain unexplained by such a simple description. T. E. Creighton, Bioessays 8 (1988) 57–63 shows that the perturbation introduced in the native state must also be taken into account.

Many attempts have been made and reported in the literature to engineer disulfide bridges, with varying success. Pantoliano et al., Biochemistry 26 (1987) 2077–2082, having introduced two cysteine residues into subtilisin via point mutations in the gene, obtain a 3° C. increase of the melting temperature. J. E. Villafranca et al., Biochemistry 26 (1987) 2182–2189, have introduced a cysteine residue by point mutation into dihydrofolate reductase and taken advantage of the presence of a free cysteine in the wildtype enzyme to form a disulfide bridge. This disulfide bond, however, has an unexpected effect, since the mutant enzyme has no increased resistance to thermal denaturation, but is more resistant to guanidine hydrochloride denaturation. In these two cases, the mutated enzymes are not as stable as expected.

These two common ways are suitable for making either a double or a single point mutation, as illustrated above. For multimeric proteins (enzymes) composed of monomeric units related by symmetry axis, a third possibility may exist: create a disulfide bridge by a single point mutation without any requirement of a free Cys. This method was successfully used by Sauer et al., Biochemistry 25 (1986) 5992–5998, in lambda-repressor: they obtained a 10° C. increase of the melting temperature, a 60% increase of resistance towards urea denaturation and moreover the binding constant was improved.

As a prerequisite for the latter method a symmetry axis is needed between at least two monomers. A symmetry axis being also a rotational axis, one of the properties of these axes is that the distance between one point and the axis during rotations is maintained. Thus, a point mutation introduced near the symmetry axis of a multimeric structure will be reproduced closely to this point. This method offers the advantage of introducing an intermonomer disulfide bridge by a single point mutation.

According to another preferred embodiment of the invention enhanced stability of the tetrameric structure of glucose isomerase is achieved by stabilizing the dimeric structure. This can be envisioned as the denaturation of the enzyme being an at least partly, reversible reaction of the tetramer into the dimers, and a subsequent dissociation of the dimers into two monomers each. By stabilizing the dimeric structure, the denaturation of the dimer will progress more slowly, and consequently reassociation into a tetramer will improve. Substitutions which reduce the susceptibility of the monomeric and/or dimeric structure for chemical modification may also have a stabilizing effect since they undo the irreversibility of the unfolding of the protein.

In a further preferred embodiment of the invention the tetrameric structure is indirectly stabilised by stabilising the dimeric structure or even the monomeric structure of glucose isomerase by special mutations. By changing the packing of the monomeric and/or dimeric structures the conformational freedom of each of the parts of the tetrameric structure is decreased which causes a stabilizing effect on the tetramer.

It will be clear that mutations stabilizing the interactions between enzyme subunits will also be able to stabilize interactions between (folding) domains within a monomeric protein. For a more detailed explanation of the terms subunits and domains, reference is made to our copending application PCT/EP 89/00838, which has also been filed on Jul. 17, 1989.

It will also be evident to those skilled in the art that, if it is desired to provide for glucose isomerases with decreased stability, the stabilising forces as described above can be weakened by applying similar processes. Mutants with such properties and processes for obtaining such mutants form also part of this invention.

In the present specification both the three letter and the one letter code for amino acids is used. This code is explained in the following Table 1:

TABLE 1

| | | | | | |
|---|---|---|---|---|---|
| Alanine | Ala | A | Leucine | Leu | L |
| Arginine | Arg | R | Lysine | Lys | K |
| Asparagine | Asn | N | Methionine | Met | M |
| Aspartic acid | Asp | D | Phenylalanine | Phe | F |
| Cysteine | Cys | C | Proline | Pro | P |
| Glutamic acid | Glu | E | Serine | Ser | S |

TABLE 1-continued

| Glutamine | Gly | G | Tryptophane | Trp | W |
|---|---|---|---|---|---|
| Histidine | His | H | Tyrosine | Tyr | Y |
| Isoleucine | Ile | I | Valine | Val | V |

The invention provides also for a method of improving the interaction between glucose isomerase subunits, which is based on the insight of the three-dimensional ("3D") structure of the molecules. Information on the 3D structure of the enzyme (or enzyme complex) is of great importance to be able to make predictions as to the mutations which can be introduced.

Gross structural data have been reported for glucose isomerase of Streptomyces rubiginosus (Carell et al., J. Biol. Chem. 59 (1984) 3230-3236), Streptomyces olivochromogenes (Farber et al., Protein Eng. 1 (1987) 459-466, and Arthrobacter (Henrick et al., Protein Eng. 1 (1987) 467-475.

Although no amino acid sequence data are available for these enzymes the 3D-structural homology with Actinoplanes missouriensis glucose isomerase is striking (see F. Rey et al., Proteins 4 (1988) 165-172). To show the general applicability of the method disclosed in this specification the genes for glucose isomerase originating from various species have been cloned and sequenced. The amino acid sequences of glucose isomerases as deduced from the genes of Streptomyces violaceoruber, Streptomyces murinus, Arthrobacter spec. and Streptomyces thermovulgaris are shown to be homologous. Published amino acid sequences for the glucose isomerases of Ampullariella sp. (Saari, ibid.) and Streptomyces violaceoniger (Nucl. Acids Res. 16 (1988) 933), deduced from the nucleotide sequences of the respective genes, display a close homology to Actinoplanes missouriensis glucose isomerase. In addition, WO 89/01520 discloses that the amino acid sequence of Streptomyces rubiginosus glucose isomerase is homologous to Ampullariella sp. glucose isomerase.

Despite the absence of 3D structural data for most glucose isomerases, it can be concluded that all glucose isomerases from Actinomycetales have a similar tetrameric organisation.

According to an aspect of the invention ionic bridges can be introduced in glucose isomerase as follows. The glucose isomerase tetramer is screened, looking for negatively charged residues (Asp and Glu, ionized at pH values as used in the application conditions in question) whose carboxylate moieties are distant by at least 8 Å from possible positively charged atoms (distal nitrogens of Lys and Arg). Fourteen residues are found to satisfy this criterion. Among these candidates, residues are selected participating in the interfaces and furthermore being situated in the interior of the protein. This latter constraint is introduced in order to eliminate the possibility of forming salt bridges at the protein surface, which are expected to have smaller effects on the overall stability (exposed charged residues may indeed be involved in hydrogen bonding to water molecules and interacting with counter ions). Accordingly, the creation of a new salt bridge involving a buried residue combines two stabilizing contributions: firstly, removal of the (unfavorable) existence of a buried isolated charge and, secondly, creation of an ionic pair protected against the influence of the substrate or solvent.

Among the 14 negatively charged and isolated residues in Actinoplanes missouriensis glucose isomerase, 3 are situated at the interfaces: Asp 146, Glu 221 and Asp 264. They are all relatively buried (respective accessible surfaces in the tetramer: 46.9 and 42 Å$^2$). In a preferred embodiment of the invention new salt bridges involving these residues are created, using methods described hereinbefore. Similar mutations can be introduced in other glucose isomerases, e.g. those obtained from sources mentioned before.

Using the techniques as described above or other techniques known to people skilled in the art, several more point mutations can be made in order to enhance the stability of the tetrameric glucose isomerase structure. (For structural data of the Actinoplanes missouriensis glucose isomerase, see F. Rey et al., ibid.). Among these, the following mutations are concerned with the stability of one monomer subunit:

- substitution of Gly residues into other residues (α-helix B) with the aim of decreasing the entropy of the unfolded state
- excision of a flexible loop (between α-helix G and β-strand H) for reducing the hydrophobic exposed surface
- introduction of a Pro residue at the beginning of β-strand E) (decrease of entropy of the unfolded state)
- mutation into Phe (α-helix G) in order to form an aromatic cluster to put an extra-contribution in the protein structure stabilization. In a further preferred embodiment of the invention substitution of arginine for lysine is performed at sites in the glucose isomerase molecule, stability of which is sought to be increased. Both residues have to be sterically accommodated in the 3D-structure of the protein.

In proteins, lysine residues, but not arginines, are prone to chemical modification. Thus, the epsilon amino group in lysine is known to react with aldehydes and ketones to generate Schiff base adducts and further modification products, which eventually results in the loss of biological activity (see e.g. P. Higgins & H. Bunn, J. Biol. Chem. 256 (1981) 5204-5208). In particular, in glucose isomerase application where high concentrations of glucose and fructose are present at elevated temperatures, such chemical modifications are an important factor in enzyme inactivation. Where lysine residues occur within interfaces between domains and-/or subunits, chemical modification at such sites is likely to promote domain or subunit dissociation and/or to hamper the correct reassociation of the subunits and/or domains which are consequently irreversible trapped in the dissociated state. At such sites mutations of lysine residues to arginine residues will eliminate chemical modifications involving the epsilon amino group of lysine. Reference is made in this connection to our co-pending patent application PCT/EP89/00838, also filed on Jul. 17, 1989.

By substituting arginine residues for specific lysine residues in glucose isomerase, the extent of chemical modification and its effect on enzyme activity and/or stability is reduced. Consequently, a change of a lysine residue to arginine will improve the stability of glucose isomerase during application.

Also, at sites which sterically accomodate the lysine to arginine mutations, a substitution of the arginine residues for the lysine residues will still result in an increased stability of the protein. Because the side chain flexibility for arginine is less than for lysine, due to the presence of the guanidinium group, the mutation of lysine to arginine is favored on entropic grounds. In addition, the guanidinium group is capable of forming more hydrogen bonds with neighbouring residues in the protein also leading to improved stability.

In still another preferred embodiment of the invention, particularly where enhancement of thermal stability of glucose isomerase is sought, at least one lysine residue occurring initially and particularly at a location of the type defined hereinafter is changed to arginine. The substitution of arginine for lysine will improve the electrostatic interactions in which the substitute arginine residue then participates, particularly interactions within the interface between subunits and/or domains. In this embodiment, the lysine residue to be replaced should preferably comply with the following requirements with respect to the folded, native, protein conformation:

1. The residue to be replaced should be directly involved in electrostatic interactions, preferably in the interface between subunits and/or domains.
2. The mutation should occur at a site that can sterically accommodate the amino acid residue that is introduced.
3. The residue should occur at a site of low solvent accessibility and, preferably be part of an interface between subunits and/or domains.

Preferably, one should search for amino acid residues in glucose isomerase which, while fulfilling criteria (1) and (2), have the lowest accessible surface area ("ASA") in the protein, simultaneously requiring that the ASA has a value lower than the average determined for the given residues. In sites which satisfy these prerequisites, arginine, as compared to lysine, provides an improved electrostatic interaction due to the physical-chemical properties of its side-chain guanidinium group (see e.g. D. Wigley et al., Biochem. Biophys. Res. Comm. 149 (1987) 927–929).

It is generally desired to retain a substantial amount of enzymatic activity of the mutant glucose isomerases, modified as taught by the present invention. To retain such enzymatic activity, the amino acid residues that are to be replaced should preferably not be those that have been identified as catalytic residues or as being substantially involved in cofactor binding.

It is clear that a specific amino acid substitution in accordance with the present invention can modify the stability of glucose isomerase by the combined effects mentioned above, e.g. effects such as changing the strength of an electrostatic interaction, changing the number of hydrogen bonds with neighbouring residues, by changing the conformational entropy of the enzyme or by influencing the extent of chemical modification.

A mutant glucose isomerase according to the present invention can be produced by the following general procedure. First, a careful analysis of the mechanism or mechanisms involved in glucose isomerase inactivation under specific denaturing conditions is carried out. Using the knowledge obtained from this analysis, specific lysine or arginine residues can then be identified as candidates for replacement. This is done by careful examination of the 3D structure of the enzyme, determined by methods such as crystallography (H. Wyckoff et al., (1985) "Diffraction Methods for Biological Macromolecules", Meth. Enzymol. Vols. 11–115, Aced. Press), NMR analysis (K. Wuthrich, (1986) in "NMR of Proteins and Nucleic acids", J. Wiley & sons), or, alternatively, from structure predictions based on analysis of the primary structure (for a review, see W. Taylor, Protein Engineering 2 (1988) 77) or structure derivations based on available 3D structures from homologous proteins (see e.g. T. Blundell et al., Nature 3 (1987) 347).

Finally, the substitution of the amino acid residue, located at a preferred side can be achieved by conventional methods, particularly site-directed mutagenesis of the DNA sequence encoding the glucose isomerase, using for example the vectors and procedures as described by Stanssens et al. (ibid.) and bacterial strains described by Zell and Fritz The mutations discussed above are only given by way of illustration of the invention without intending to limit the scope. The invention is further illustrated by the following non-limitative examples.

Unless otherwise specified in the examples, all procedures for making and manipulating recombinant DNA were carried out by the standardized procedures described by Maniatis et al. (1982).

The following plasmids, vectors and bacterial strains, used or prepared in the Examples have been deposited in the Deutsche Sammlung für Mikroorganismen, Göttingen, West-Germany, under the provisions of the Budapest Treaty, or at the Centraal Bureau voor Schimmelcultures ( CBS), Baarn, The Netherlands:

| pMc5-8 | DSM 4566 |
|---|---|
| pMa5-8 | DSM 4567 |
| pECOR251 | DSM 4711 |
| E. coli K527 | CBS 471.88 |

EXAMPLE 1

Isolation and cloning of the glucose isomerase gene from Actinoplanes missouriensis (DSM 43046) Production of D-glucose isomerase in E. coli D-glucose isomerase (GI) is synonymously used for D-xylose isomerase (D-xylose) ketol-isomerase, (EC 5.3.1.5), an enzyme that converts D-xylose into D-xylulose. The D-glucose isomerase from *Actinoplanes missouriensis* produced by engineered *E. coli* strains is designated as EcoAmi (DSM) GI. To distinguish the *Actinoplanes missouriensis* gene coding for GI from the analogous *E. coli* xylA gene, the former will be designated as GI.

Total DNA from *Actinoplanes* missouriensis DSM 43046 was partially digested with Sau3A. The digest was fractionated on a sucrose gradient and fragments with lengths between 2 and 7 kilobases (kb) were ligated in the unique BglII site of plasmid pECOR251. The xylose isomerase deficient *E. coli strain AB* 1886— as described in Howard-Flanders et al. (Genetics 53 (1966) 1119) and derived from *E. coli* strain AB 1157 (DSM 1563)—was transformed with the ligation mix and subsequently grown on minimal agar plates (Miller ( 1972 ) in "Experiments in Molecular Genetics", Cold Spring Harbor Laboratory, Cold Spring Harbor, N.Y.) supplemented with 100 mg/l ampicillin and 0.2% (w/v) xylose (MMX). Thirty seven clones were recovered (designated pAMI1-137) and grown in LB medium containing 100 mg/l ampicillin. Recombinant plasmid DNA was isolated and analyzed by restriction digests. Two groups of plasmids could be recognized, one (e.g. pAMI7) containing a 2.8 kb insert, the other (e.g. pAMI25) containing an 4.0 kb insert. An extensive restriction analysis showed that both types of inserts had a region of about 2.0 kb in common. Sequence determination of this region by the chemical degradation method (A. Maxam and W. Gilbert, Proc. Natl. Acad. Sci. USA 74 (1977) 560) revealed an open reading frame with a length of 1182 nucleotides which was identified as the coding region of GI. The nucleotide sequence of GI, together with the derived amino acid sequence are shown in FIG. 15. In the following, the numbering of amino acids refer to FIG. 15.

Very high expression of GI could be achieved in *E. coli* by placing the gene under the transcriptional control of the rightward promoter ($P_R$) of bacteriophage lambda as follows:

Plasmid pLK94 (J. Botterman and .M. Zabeau, DNA 6 (1987) 583) was first modified to eliminate the PstI site in the β-lactamase gene. This was done by isolating the 880 bp EcoRI/PstI fragment of pLK70-70p (Botterman and Zabeau, ibid.) containing the N-terminal part of the β-lactamase gene, and the 1700 base pair (bp) EcoRI/PstI fragment of pLK94 containing the C-terminal part of the β-lactamase gene as well as the replication origin. Subsequent ligation of these fragments yielded pLK94p.

pAMI7 was cleaved with PstI and a mixture of two purified fragments of about 1800 bp in length, one of which contains the GI gene, were ligated into the PstI site of pLK94p. The ligation mixture was used to transform *E. coli* strain AB 1886. Ampicillin resistant, GI+- transformants were obtained by growing on MMX.

Plasmid DNA was isolated from a few selected transformants and characterized by restriction analysis. Plasmid pLK94p harboring the PstI fragment containing GI was designated as pLK94GI. The orientation of GI is such that the unique BamHI site is located about 470 bp upstream from the GTG initiation codon.

pLK70-70p was cleaved with PstI, made blunt end by DNA polymerase I (Klenow fragment) and subsequently digested with XbaI. pLK94GI was linearized with BamHI and digested with exonuclease Ba131. Samples were taken at various times—the reaction was stopped with disodium ethylenediaminetetraacetate (EDTA) — cleaved with XbaI and analyzed by gel electrophoresis to determine the average size of the resected BamHI-XbaI fragments. Fragments, ranging in size from 1350 to 1450 bp were eluted from the gel. The fragment were ligated in pLK70-70p. *E. coli* K514 (C. Colson et al., Genetics 52 (1965) 1043) was transformed with the ligation mixture and ampicillin resistant transformants were selected at 37° C. The plasmid DNA, isolated from several transformants was characterized by restriction analysis. Twenty four clones containing plasmids with in intact GI were retained and tested for production of EcoAmi (DSM) GI. Cultures were grown overnight at 37° C. whereafter total cellular extracts were fractionated by polyacrylamide gel electrophoresis (PAGE) on 12.5% sodium-dodecyl sulfate (SDS) (U. Laemmli, Nature 227 (1970) 680). When compared to an untransformed K514 control culture, one of the clones was found to direct high level synthesis of a new protein of molecular weight 42 kilodaltons (kd) which was identified as EcoAmi (DSM) GI by Western blotting using a polyclonal serum raised against purified *Actinoplanes missouriensis* GI. The plasmid conferring high EcoAmi (DSM) GI production on *E. coli* K514 was designated as pLK70GI.

The $P_R$-GI transcriptional unit could be excised as a EcoRI-XbaI fragment, the sequence of which is given in FIG. 16. After elution from an agarose gel, this fragment was ligated in both pMa5-8 and pMc5-8 which were digested with EcoRI and XbaI, yielding pMa5-GI and pMc5-GI respectively. These vectors were found to direct equal and efficient synthesis of EcoAmi(DSM) GI while the expression level did not differ significantly from that obtained with pLK70GI.

Expression of GI could be further increased by changing the GTG initiation codon into an ATG triplet. This was done by site directed mutagenesis as described in Example 4 using the following oligonucleotide primer:

5'-GGACAGACATGGTTACC-3' (SEQ ID NO:13)

Wildtype and mutant GI enzymes were produced in *E. coli* strain K514 grown in a medium composed of 1% tryptone, 1% NaCl, 0.5% yeast extract, and either ampicillin (100 mg/l) for pMA type vector or chloramphenicol (25 mg/l) for pMC type vector. Cells were grown overnight at 37° C. and centrifuged. The EcoAmi(DSM) GI enzyme could be purified as follows. The cell pellet was resuspended in a minimal volume of 0.05M Tris (hydroxymethyl) aminomethane (Tris/HCl)), 0.1 mM $CoCl_2$, 10 mM $MgCl_2$, 0.2M KCl, 5% glycerol, and 5 mM EDTA, pH 8.0, and lysozyme was added to a final concentration of 1.0 mg/ml. After standing for 20 min at 0° C., the cells were lysed using a French press, centrifuged (30 min at 23,000 g), and the supernatant diluted with an equal volume of 5% streptomycin sulfate. Incubation was maintained for 3 hours at 4° C. and followed by centrifugation (30 min at 23,000 g). The resulting supernatant was heated to 70° C. (except for the mutants K253Q and K100R which were heated to only 50° C.) for 30 min and centrifuged again. The soluble upper phase was made 80% with ammonium sulfate. The precipitate which contained most of the enzymatic activity was collected by centrifugation, and then dissolved in 0.02M Tris/HCl, 5 mM EDTA, 0.85M ammonium sulfate. The subsequent chromatographic steps included Phenyl-Superose, Sephacryl S-200 HR, and finally Mono-Q HR 10/10. Importantly, the addition of 5 mM EDTA to all buffers for chromatography was necessary in order to eliminate metal ions. Prior to use, the resulting enzyme was dialyzed 3 times against 200 volumes of 10 mM triethanolamine, pH 7.2, containing 10 mM EDTA (final pH is about 5.2), and again against 200 volumes of 5 mM (2-N-Morpholino)ethanesulfonic acid) (MES), ph 6.0, with 3 buffer changes. The metal content of the final enzyme preparation was determined by atomic absorption spectrometry on a Varian SpectrAA 30/40, and revealed that EcoAmi(DSM) GI was metal free; as an example, it could thus be shown that cobalt ions, which bind to the enzyme with very high affinity, accounted for only $\pm 1 \times 10^{-4}$ mol. per mol of EcoAmi(DSM) GI monomer (when EDTA was omitted in the chromatographic buffers, the latter value increased to 0.5 mol. cobalt per mol. enzyme monomer). The purity of the EcoAmi(DSM) GI was assessed by SDS-PAGE and silver staining, and also by reversed phase high performance liquid chromatography (HPLC) on a Vydac C4 column.

The enzymatic activity of glucose isomerase was assayed as described below (1 unit of enzymatic activity produces 1.0 micromole of product -D-xylulose or D-fructose-per minute; therefore, specific activity -spa- is expressed as units per mg of GI enzymes).

The triphenyltetrazoliumchloride (TTC) assay was previously described for the visualization of D-xylose isomerases on disc electrophoresis (K. Yamanaka, Bull.

Yamaguchi Med. School 18 (1971) 1). This staining method is based on the reaction of sugars with the tetrazolium salt to form formazan at room temperature; the reaction is specific for ketose at room temperature as aldose reacts only at 100° C. On gels, active xylose isomerase can thus be identified as a pink-red band. With minor modifications, this activity test was adapted for use in the Pharmacia PhastSystem. Briefly, following eletrophoresis, the native-PAGE gel was transferred to the PhastSystem staining chamber and incubated for 15 min at 50° C. in 20 mM Tris/HCl, pH 7.2, with 50 mM xylose, 10 mM MgC12, 0.1 mM $COCl_2$; after washing with demineralized water 0.5 min at 4° C., the gel was immersed for 3 min at 20° C. in 0.1% triphenyl-tetrazoliumchloride freshly prepared in 1N NaOH; the reaction was stopped by incubating the gel in 2N HCll for 15 min at 20° C.; final wash was in water (0.5 min at 4° C.).

GI activity can also be assayed directly by measuring the increase in absorbance at 278 nm of xylulose produced at 35° C. by isomerisation of xylose by glucose isomerases. This assay was performed in 50 mM triethanolamine buffer, pH 7.5, containing 10mM $MgSO_4$, in the presence of 0.1M xylose. Glucose isomerase final concentration in the assay was +0.01 mg/ml, and precisely determined, prior to dilution in the enzymatic assay mixture, by absorption spectroscopy using an extinction coefficient of 1.08 at 278 nm for a solution of enzyme of 1.0 mg/ml.

In the D-Sorbitol Dehydrogenase Coupled Assay, enzymatic determination of D-xylulose was performed at 35° C. as previously described (Kersters-Hilderson et al., Enzyme Microb. Technol. 9 (1987) 145) in 50 mM triethanolamine, pH 7.5, 10 mM $MgSO_4$, and 0.1M xylose, in the presence of $\pm 2 \times 10^{-8}$M D-sorbitol dehydrogenase (L-iditol : AND oxido-reductase, EC 1.1.14 ), and 0.15 nM NADH, except that the incubation buffer also included 1 mM ethylenebis(oxyethylenenitrilo)tetraacetic acid (EGTA). Glucose isomerase final concentration in this assay was $\pm 2.5 \times 10^{-3}$ mg/ml, and precisely determined as described above.

With glucose as a substrate GI activity can be assayed by the measurement of D-fructose produced during the isomerization reaction using the cysteine-carbazole method (CCM) which is based on the reaction of ketosugars with carbazole in acids to yield a purple product (Dische and Borenfreund, 1951).

EXAMPLE 2

Kinetics of heat inactivation of EcoAmi (DSM) GI.

Heat-inactivation kinetics experiments were performed on the metal-free glucose isomerase with the additions described in each specific case. In brief, the purified enzyme was equilibrated in the desired buffer and the solution was drawn up into a Hamilton gas-tight syringe with a Teflon needle, that had been previously inserted into a glass mantle connected to a circulating waterbath (Lauda, RM6) set at the indicated temperature. Previous experiments have shown that temperature equilibration of the enzyme solution from 25° to 85° C. is achieved in less than one minute. At appropriate times, aliquots were withdrawn into Eppendorf tubes and the heat denaturation process was quenched by cooling the samples to 0° C.

Alternatively, large samples were incubated as individual aliquots in Reacti-Vials (Pierce).

1. Temperature and metal dependence

The kinetics of heat-inactivation of EcoAmi(DSM) GI in 50 mM (3-(N-Morpholino)-propanesulfonic acid) (MOPS), pH 7.2 at 25° C. ($pK_a=7.15$ at 25° C.; dH/°C.=−0.001), as a function of temperature is illustrated in FIG. 1 (No metal added), FIG. 2 (+10 mM $MgSO_4$), and FIG. 3 (+10 mM $COCl_2$). All the data points are remarkably well fitted by theoretical decay curves corresponding to a first-order process regardless of the temperature used and of the presence or nature of the metal ion.

The data also demonstrate the stabilizing effect of magnesium and, even more so, of cobalt ions. Enzyme inactivation by heat was found to be irreversible; accordingly, heating was shown to induce protein aggregation In the presence of $Mg^{2+}$, we could demonstrate that loss of enzymatic activity correlated remarkably well with the extent of protein precipitation.

Figure 2:
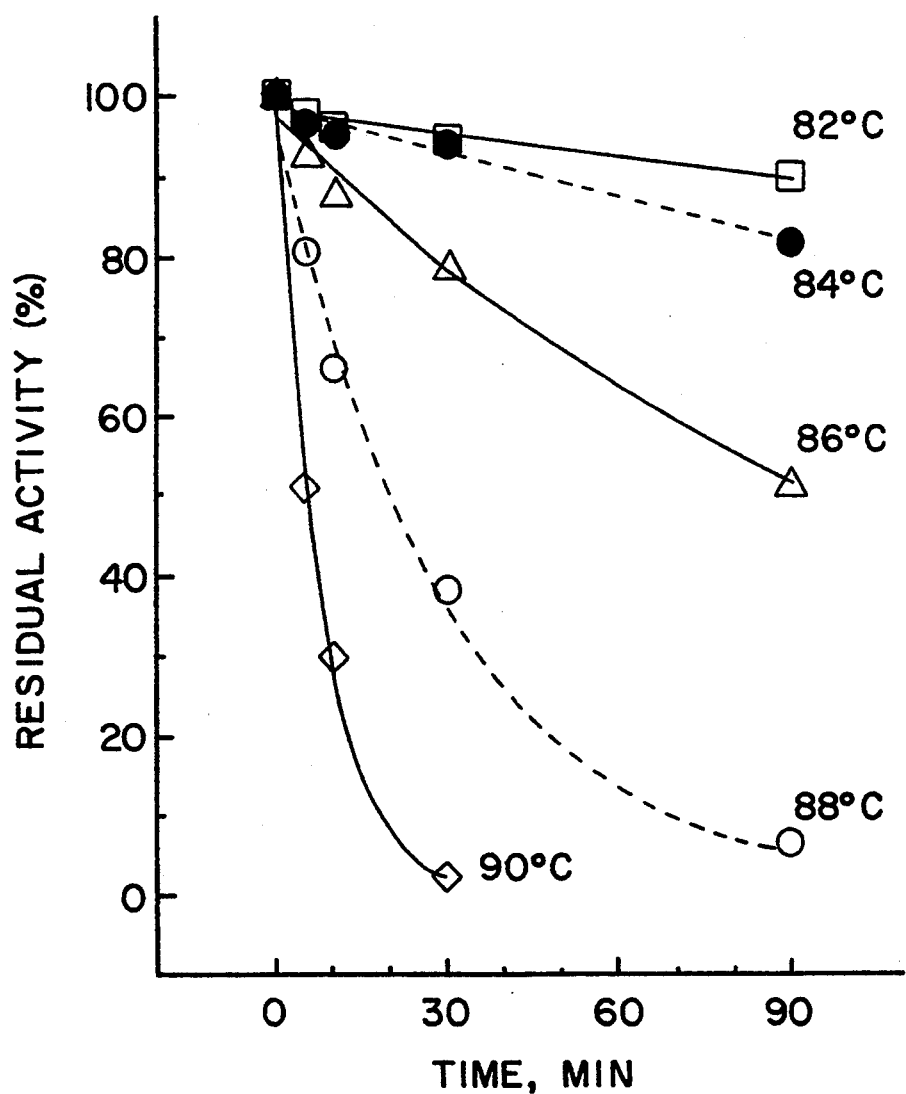
FIG. 2. Same as FIG. 1. 10 mM $Mg^{2+}$ was added.
Figure 3:
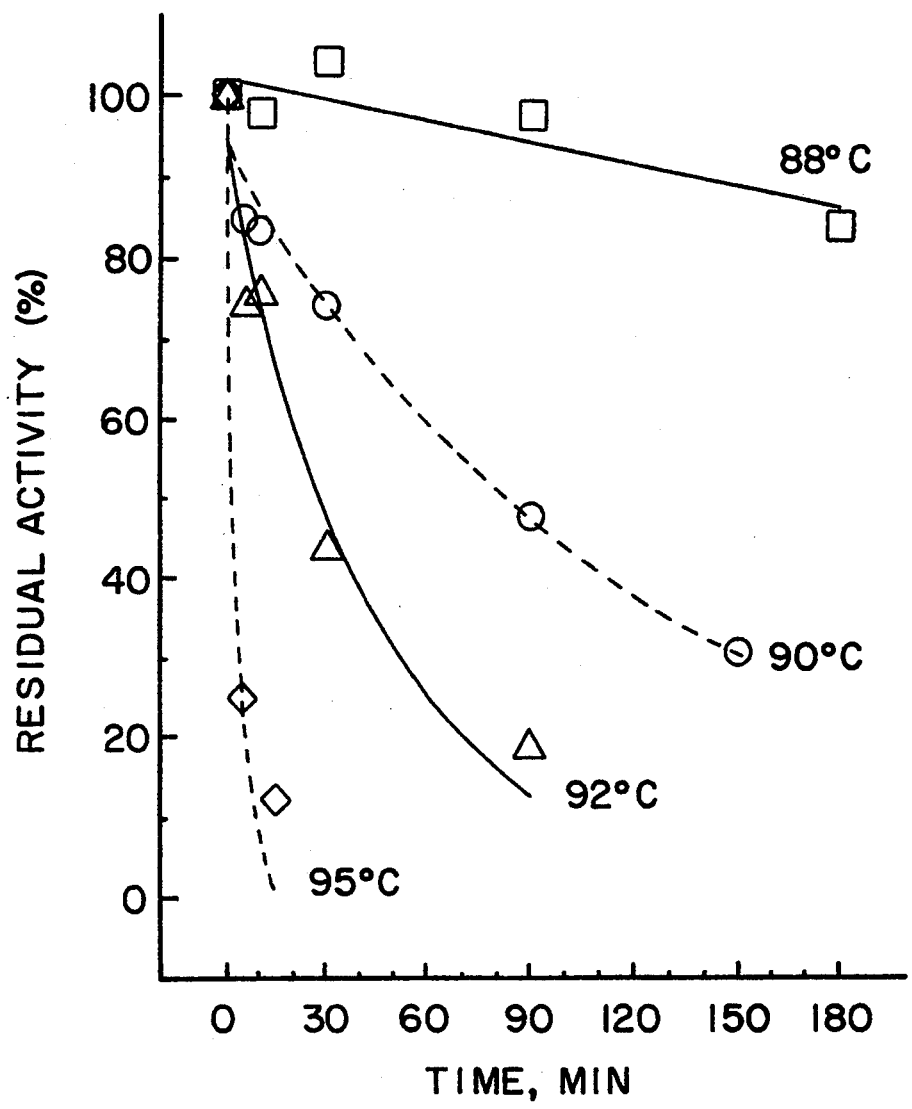
FIG. 3. Same as FIG. 1. 10 mM $Co^{2+}$ was added.
Figure 4:
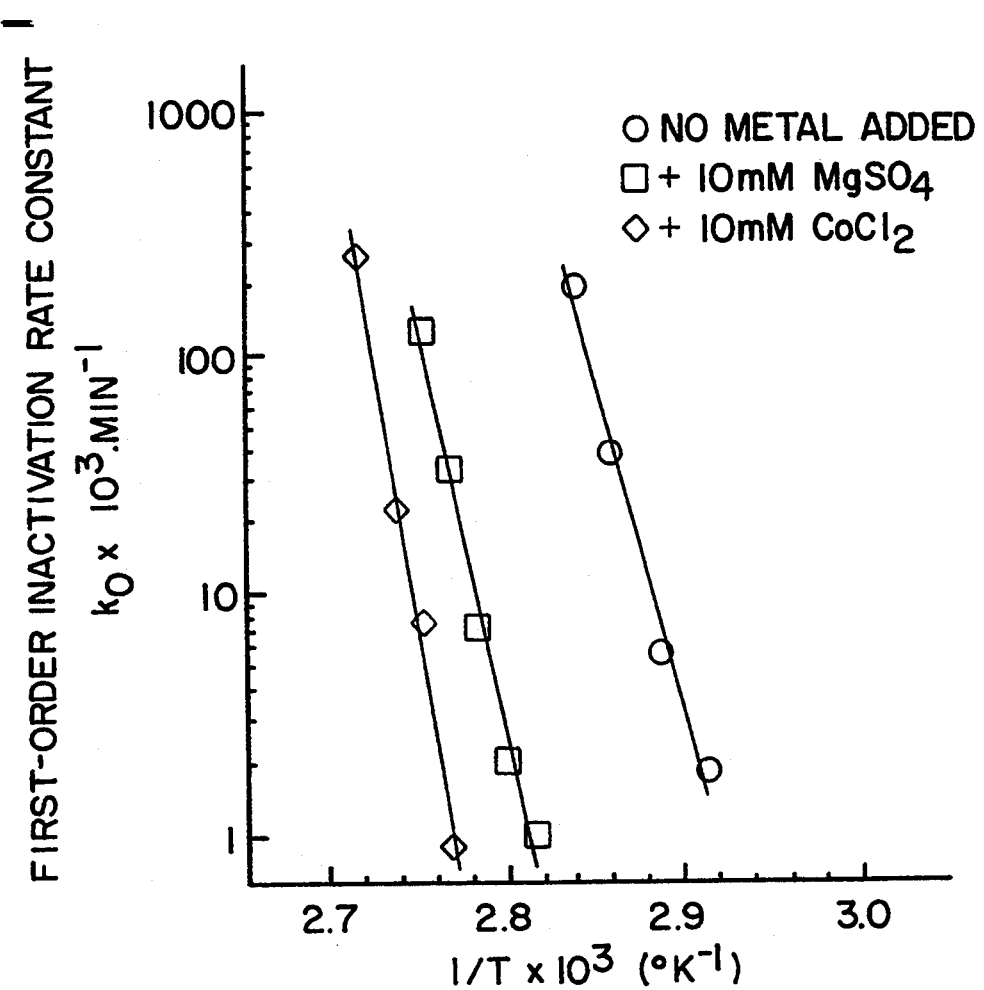
FIG. 4. Arrhenius plot of the temperature dependence for heat inactivation of EcoAmi(DSM) GI in 50 mM MOPS, pH 7.2 at 25° C.

FIG. 4 summarizes the data of FIGS. 1, 2 and 3, and shows that in the temperature intervals used the Arrhenius plot are linear whether metal is present or not.

These results indicate that thermal denaturation of EcoAmi(DSM) GI originates from one single event under all conditions tested; it is not known whether the same limiting step prevails in the absence and in the presence of metal, but the linearity of the Arrhenius plots supports the contention that this step is unique under a specific set of experimental conditions.

2. pH and ionic strength dependence

The affinity of GI stabilizing metals is strongly pH dependent; in particular, it is considerably reduced below pH 6. Consequently, the influence of pH on the thermostability of EcoAmi(DSM) GI was studied using the metal-free enzyme in the absence of added metals.

Figure 5:
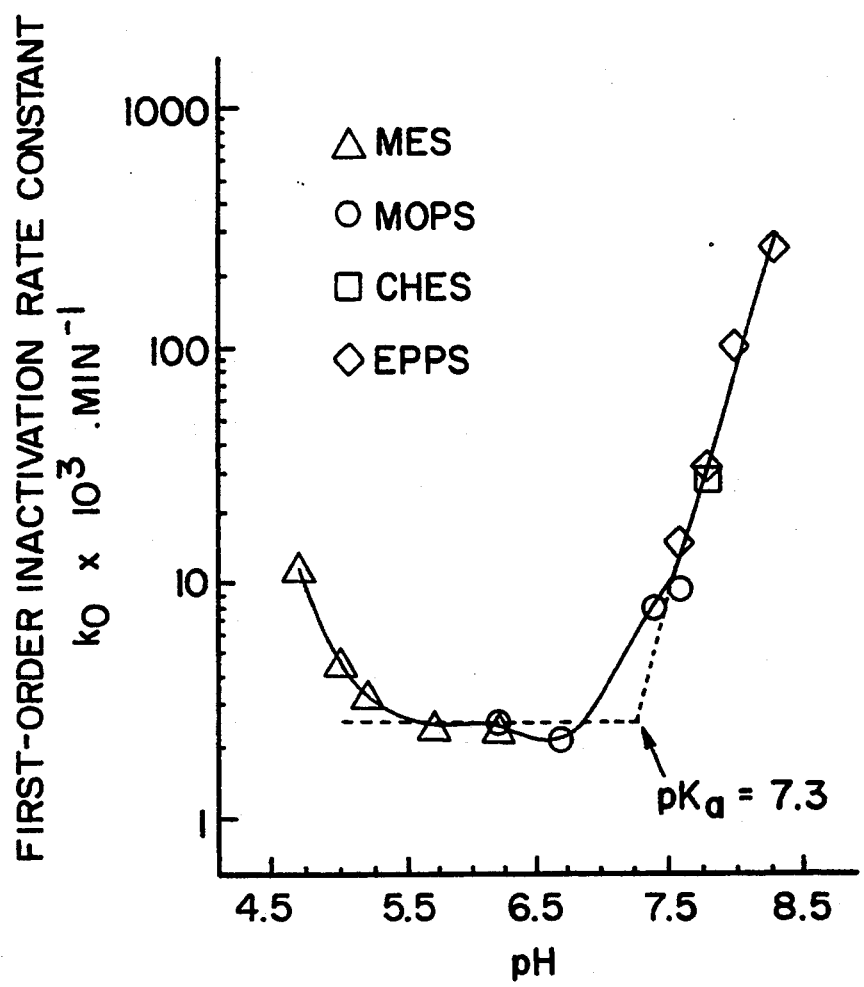
FIG. 5. pH dependence of heat inactivation of metal-free EcoAmi(DSM) GI at 72° C. in the absence of added metal. CHES=2-(cyclohexylamino) ethane sulfonic acid.

In the pH range of 4.7 to 8.3, the inactivation of EcoAmi(DSM) GI at 72° C. always followed first-order kinetics. FIG. 5 shows that the inactivation rate constant, $k_D$, remained practically unaltered between pH 5.5 and 6.7, but was increased on either side of this pH range.

Figure 6:
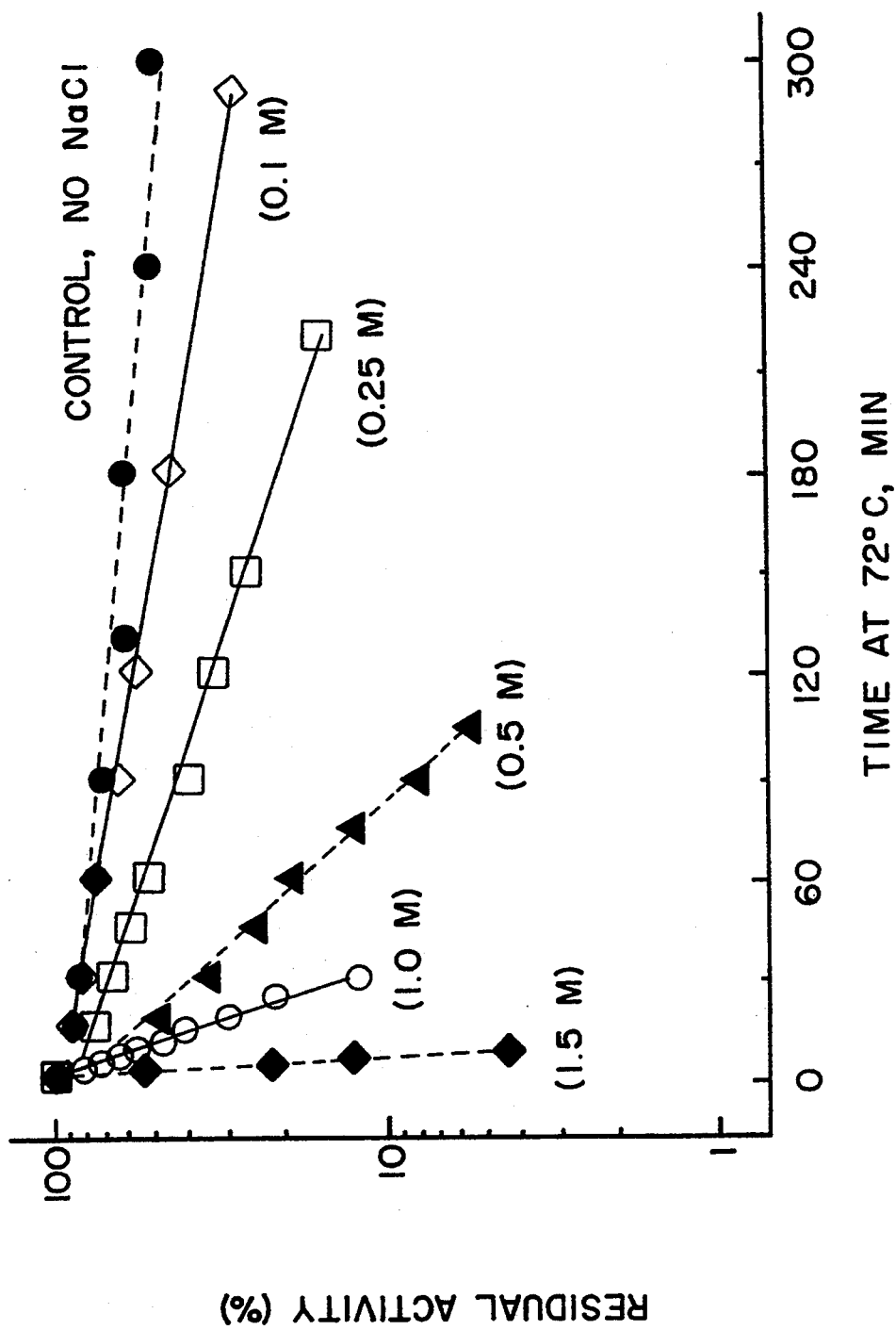
FIG. 6. Ionic strength effect on the kinetics of heat inactivation of metal-free EcoAmi(DSM) GI in 50 mM MOPS, pH 6.7, 72° C. No metal added.

FIG. 6 demonstrates that the kinetics of heat inactivation of the enzyme in the absence of added metal was increased as a function of the ionic strength. This, together with the pH dependence data, strongly indicates that polar residues are involved in the thermal stability of EcoAmi(DSM) GI.

Figure 7:
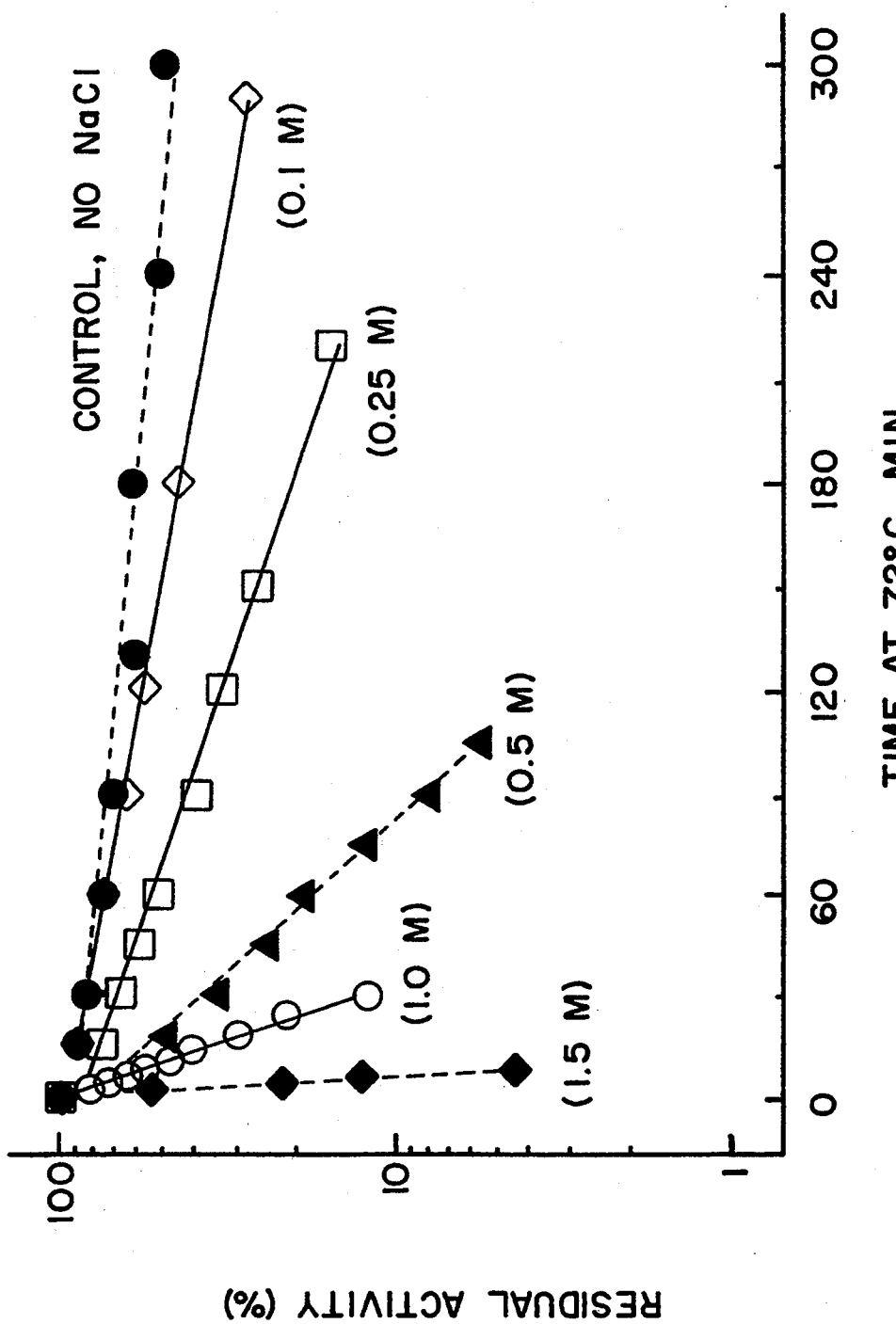
FIG. 7. Ionic strength effect on the heat inactivation kinetics of metal-free EcoAmi(DSM) GI in 50 mM MOPS, pH 7.6, 72° C. No metal added.

This condition is further supported by the data in FIG. 7 where it is shown that a moderate increase in pH (i.e. pH 6.7 to pH 7.6 at 72° C.) significantly amplified the destabilizing effect of sodium chloride.

3. Effects of urea and cyanate

GI is a tetramer made of four identical subunits (F. Rey et al., ibid. ).

The influence of urea and cyanate was assessed in an attempt to identify structural changes that might account for the loss of enzymatic activity as a result of heating i.e. subunit dissociation and/or unfolding.

Figure 8A:
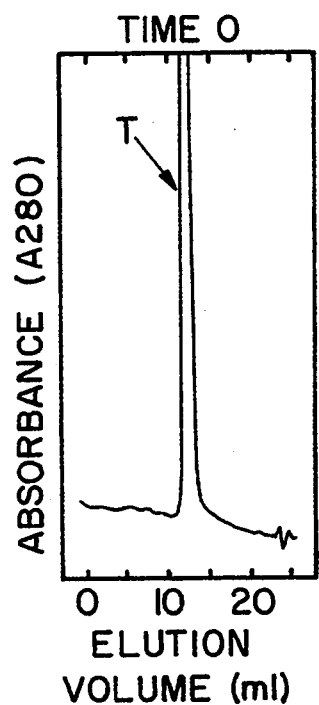
FIG. 8. SEC-HPLC of EcoAmi(DSM) GI after prolonged incubation of EcoAmi(DSM) GI in 7M urea at 25° C.
Figure 8B:
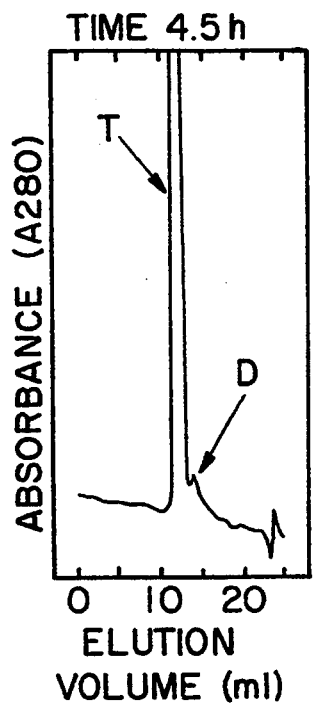
Figure 8C:
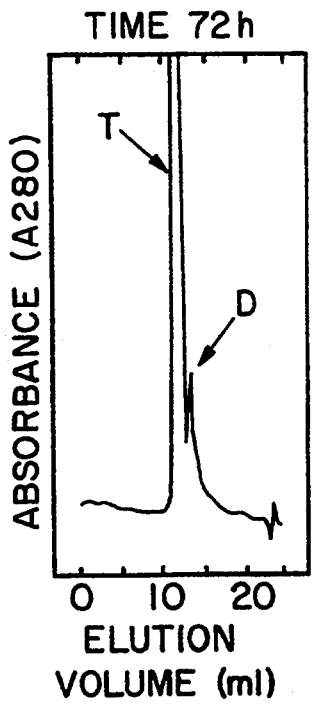

The oligomerization state of the enzyme was analysed by siz-exclusion high performance liquid chromatography (SEC-HPLC) on Superose-12 at room temperature using an elution buffer consisting of 50mM Tris/HCl pH 8.0 at 25° C. and 150 mM NaCl1 following prolonged incubation of the enzyme in 7M urea at room temperature. Native GI is shown to elute as a tetramer on SEC-HPLC. FIG. 8 shows that prolonged incubation in urea is necessary to induce a dissociation of the native EcoAmi(DSM) GI-tetramer into dimers.

Since cyanate is known to be generated from urea in solution on standing is was speculated that chemical modification of the enzyme by cyanate might be responsible for the observed subunit dissociation. To test this hypothesis, the enzyme was incubated for 16 to 24 days at room temperature in 0.2M borate pH 8.5 and 150 mM NaCl containing cyanate concentrations ranging from 0 to 200 mM and this in the absence or presence of freshly prepared 5.0M cyanate freed urea (a freshly prepared stock solution of 10M urea in Milli-Q water was passed over a column of AG 501-X8 (D) resin (Bio-Rad) according to the recommendations of the manufacturer; this treatment eliminates ionic contaminants among which cyanate).

The following observations were made:
1. Treatment with cyanate alone could not alter the elution profile of EcoAmi(DSM) GI on SEC-HPLC (FIG. 9a). Native PAGE did reveal a dose dependent chemical modification of the enzyme as evidence by the increase in negative charge (FIG. 9B), upper panel) but without apparent loss of enzymatic activity as shown by TTC-staining of the gel (FIG. 9B, lower panel).
2. After 16 days of incubation of EcoAmi (DSM) GI in 5.0M cyanate-freed urea, no dimer formation was apparent by SEC-HPLC (FIG. 10A). Some dimer-dimer dissociation however was observed after native PAGE (FIG. 10B, upper panel, 0 mM NaCNO) suggesting that at the urea concentration used (5 molar), generated cyanate induced minor chemical modification which, although not directly leading to tetramer dissociation, weakened the dimer-dimer association to an extent that dissociation could be brought forth under the influence of the electrical field applied during PAGE. Alternatively, it can also be proposed that the combined influence of urea and of the electrical field brings about tetramer to dimer dissociation.
3. The simultaneous addition of cyanate to EcoAmi(DSM) GI in 5.0M urea readily brought about tetramer to dimer dissociation in a concentration dependent fashion. This was demonstrated both by SEC-HPLC data (FIG. 10A) and by native PAGE (FIG. 10B, upper panel). The retardation in PAGE of the dimer after incubation at high cyanate concentrations is likely to result from an increased unfolding of the enzyme under these conditions. On native PAGE, the dimers showed no GI-activity after TTC staining (FIG. 10B, lower panel). This finding suggests that enzymatic activity is lost upon GI-tetramer dissociation into dimers and/or due to chemical modification.

In conclusion, the presence of both cyanate and urea is required to observe EcoAmi(DSM) GI tetramer dissociation into dimers. Since cyanate alone was ineffective, the chemically-modified amino group(s), involved in the stabilization of the tetramer structure of the enzyme, are not solvent-accessible in the absence of urea. Urea probably destabilizes the dimer/dimer interaction, thereby exposing amino acid(s) previously buried within the dimer/dimer interface. These residues, bearing either an alpha and/or an epsilon amino group, become thus available for carbamylation by cyanate. In turn, covalent attachment of cyanate to intersubunit contact residue(s) stabilizes the dimer form of the enzyme. It can therefore be proposed that the dissociation of EcoAmi(DSM) GI tetramers into dimers is probably one of the primary events in thermodenaturation. In support of this hypothesis, it could be observed that higher protein concentrations stabilized the enzyme against denaturation by heat (data not shown).

4. Glycation

Proteins have been shown to undergo glycation, i.e. nonenzymatic modification of alpha and epsilon amino groups by glucose and numerous other sugars. It was predicted that under application conditions (high glucose concentrations, pH 7.5, and prolonged utilization) glycation of EcoAmi(DSM) GI was likely to occur as well; in particular, if EcoAmi(DSM) GI tetramers dissociate into dimers at high temperature, one would anticipate that the same amino acid residue(s) reacting with cyanate in the presence of urea would become glycated with concomitant tetramer-dimer dissociation and possibly loss of catalytic activity.

Metal-free EcoAmi (DSM) GI was incubated in the absence of magnesium at 60° C. without or with D-glucose (250 mM) in 50 mM MOPS, pH 7.7 at 60° C. At appropriate times, aliquots were withdrawn, cooled to 25° C. and tested for residual enzymatic activity by the direct xylulose absorbance assay at 278 nm.

Figure 11A:
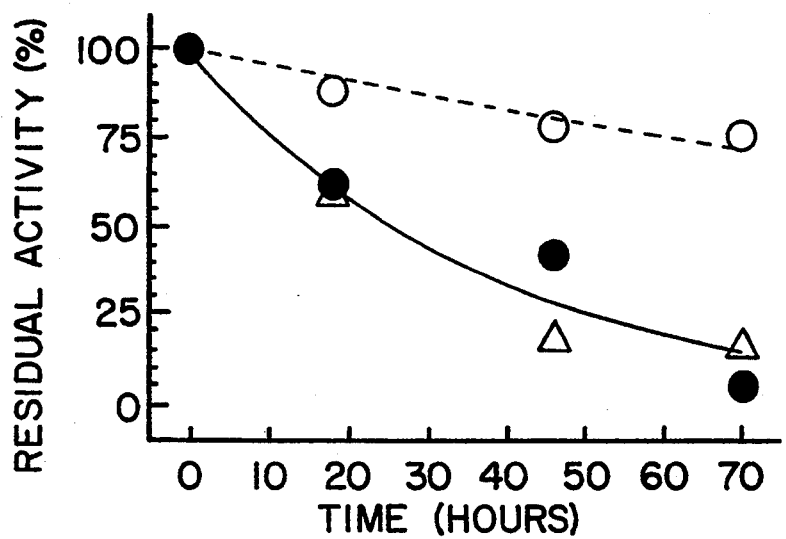
FIG. 11. Glycation of EcoAmi(DSM) GI in 50 mM MOPS, pH 7.7, 60° C. Open circles: no glucose added; Closed circles: +250 mM glucose; Triangles: incubation with glucose ( 250 mM) was followed by extensive dialysis to test for reversibility.
Figure 11B:
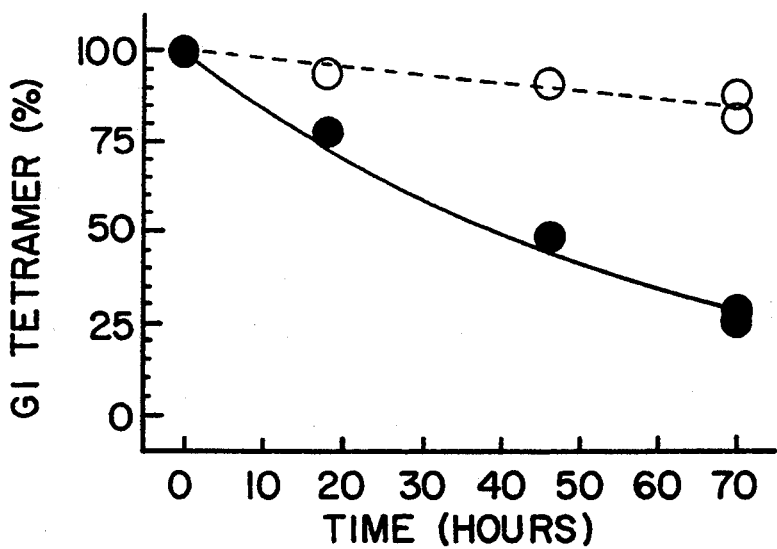
Figure 11C:
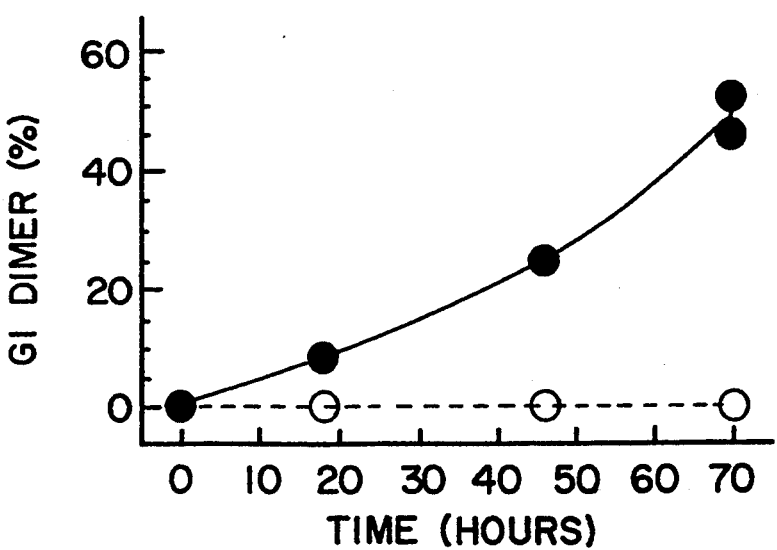

FIG. 11, Panel A, shows at that the presence of glucose significantly increased the rate of heat-inactivation of the enzyme at 60° C. This effect was not reversible as extensive buffer exchange against 50 mM MES, pH 6.0, at 4° C., could not restore the catalytic efficiency of EcoAmi(DSM) GI (triangles in FIG. 11, Panel A). Moreover, analysis of the reaction products by SEC-HPLC clearly demonstrated that, as predicted, glycation was accompanied by tetramer to dimer dissociation in a time-dependent fashion (FIG. 11, Panels B and C), a finding that supports the contention that tetramer splitting occurs at high temperature. Dissociated dimers are trapped by covalent modification with glucose of reactive amino groups likely to reside in the interdimer contacts.

FIG. 11, Panel D, shows that heating also caused formation of a protein aggregate having about the size of a hexadecamer of EcoAmi(DSM) GI (±700 kilodaltons, i.e. four GI tetramer molecules]; this aggregation was greatly enhanced in the presence of glucose. It is not known however whether aggregate formation occurs independently of, or only subsequent to, GI dissociation into dimers. Very similar results could be reproduced in a different buffer system; 12.5 mM potassium phosphate, pH 7.7 at 60° C.

It is interesting to recall that the presence of urea was necessary to cyanate to produce stable GI dimers, whereas glucose exhibited the same properties at high temperature in the absence of urea. Therefore we can conclude that both urea and heating cause the dissociation of EcoAmi(DSM) GI tetramers into dimers thereby exposing amino acid residues located in the interdimer interface; among these, previously inaccessible amino groups become available to react with cyanate or glucose thus trapping the enzyme in the dimer state.

EXAMPLE 3

Identification of lysine residues in the subunit interfaces of glucose isomerase of Actinoplanes missouriensis.

GI is a tetramer consisting of four identical subunits (A, B, C and D) (Rey et al., ibid.) which can be viewed as an assembly of two dimers (AB and CD). One can therefore distinguish two categories of subunit interfaces, interfaces between the monomers within one dimer (intradimer interface) and the interface between two dimers (inter-dimer interface).

A residue is said to participate in the subunit interface contacts if its accessible surface area (ASA) (B. Lee and F. Richards, J. Mol. Biol. 55 (1971) 379) calculated in the isolated subunit differs from that determined in the oligomer. Table 2 compiles the ASAs for the 20 subunit lysine residues both in the isolated monomer and the GI tetramer.

TABLE 2

| K | $ASA_T$ | $ASA_T$ | $A_b$ |
|---|---|---|---|
| 10 | 65.4 | 65.4 | 0.0 |
| 42 | 52.6 | 52.6 | 0.0 |
| 76 | 77.1 | 77.1 | 0.0 |
| 100 | 142.4 | 142.4 | 0.0 |
| 100 | 150.0 | 0.8 | 149.2 |
| 118 | 17.9 | 6.8 | 11.1 |
| 132 | 147.4 | 147.4 | 0.0 |
| 149 | 6.9 | 3.2 | 3.7 |
| 183 | 8.0 | 0.1 | 7.9 |
| 239 | 167.0 | 167.0 | 0.0 |
| 240 | 19.2 | 18.1 | 1.1 |
| 253 | 111.5 | 1.5 | 110.0 |
| 294 | 51.5 | 28.7 | 22.8 |
| 309 | 93.2 | 93.2 | 0.0 |
| 319 | 30.0 | 30.0 | 0.0 |
| 323 | 83.0 | 83.0 | 0.0 |
| 339 | 78.0 | 50.3 | 27.7 |
| 344 | 178.1 | 125.8 | 52.3 |
| 375 | 132.0 | 119.2 | 12.8 |
| 381 | 114.2 | 67.7 | 46.5 |

Eleven of these residues are seen to participate in subunit interfaces. Only LYS-100 and LYS-253 bury an extensive area ( 149 Å$^2$ and 110 Å$^2$, respectively) in the subunit interfaces and become almost completely buried in the tetramer. In other words, both of these residues have low solvent accessibility in the tetramer. Also, neither residue is implied in the catalytic activity of EcoAmi(DSM) GI. Furthermore, LYS-100 and LYS-253 are involved in electrostatic interactions in the subunit interfaces. LYS-100 in the S-subunit (A-LYS-100) stabilizes, through hydrogen bonding the last turn of a small helix near position 373 in the B=subunit. LYS-253 in the A-subunit ( A-LYS-252) on the other hand is involved in ionic interdimer interation with ASP-190 of the C-subunit. Using model building techniques (as described in P. Delhaise et al., J. Mol. Graph. 3 (1984) 116) it was observed that the environment of LYS-100 is not likely to accomodate a substitution to ARG, whereas the mutation of LYS-253 to ARG would be sterically possible because no bad physical contacts were apparent and ionic interations with ASP-190 remained favorable.

Another lysine residue, K294, is located at the dimer-dimer interface but is only partly buried in the tetramer (accessible surface area 22.8 Å$^2$). This residue is strictly conserved in all Actinomycete glucose isomerases (see Example 10 and FIG. 21); however K294 interacts also with N247 and D257, both of which are involved in metal binding. K294 thus will affect the stability of glucose isomerase by different mechanisms.

EXAMPLE 4

Amino acid replacements of Specific lysine residues in glucose isomerase of Actinoplanes missouriensis According to the present invention, the substitution of LYS-253 with arginine would stabilize the electrostatic interaction across the dimer-dimer interface and thereby increase the stability of EcoAmi(DSM) GI towards thermal inactivation. Moreover, this substitution would also prevent chemical modification (by glucose or cyanate) at position 253.

To assess the importance of electrostatic interactions of the A-LYS-253/C-ASP-190 ion pair in the heat stability of EcoAmi(DSM) GI, LYS-253 was mutated into glutamine to eliminate the ionic character of the lysine side-chain, this mutation being otherwise reasonably conservative.

Site directed mutagenesis was performed according to the gapped duplex DNA (gdDNA) method using the pMa5-8 and pMc5-8 like phasmid vectors (P. Stanssens et al. ibid.). Since the mutagenesis strategy requires the use of unique restriction sites upstream and downstream of the region to be mutagenized, two additional cleavage sites were introduced in the GI coding sequence without altering the encoded amino acid sequence. A KpnI site was created by nucleotide base-exchange of G at position 177 into A using the following oligonucleotide primer:

5'-CGAAGGGTACCAGG-3'   (SEQ ID NO:14)

A XhoI site was created by substitution of a C for a G at position 825 using the following oligonucleotide primer:

5'-GCCGTTCTCGAGGAGGTCG-3'   (SEQ ID NO:15)

The conversion of the GTG into an ATG codon (see Example 1) and the creation of the KpnI site were accomplished in a single mutagnesis experiment in which the relevant enzymatically phosphorylated oligonucleotides were annealed to a gdDNA derived from single stranded pMc5-GI and the large BamHI-AatII fragment of pMa5-GI.

The XhoI site was introduced in a separate experiment; the gdDNA used was constructed from single stranded pMc5-GI and the large SacI-SmaI fragment of pMa5GI. The three mutations were assembled in a single gene by combining the appropriate fragments of the double mutant and the XhoI mutant. The resultant triple mutant was designated as pMa-I. The complementary pMc5-I was constructed by insertion of the small EcoRI-XbaI fragment of pMa5-I, containing the $P_R$-GI hybrid gene, between the EcoRI and XbaI sites of pMc5-8.

pMa5-I and pMc5-I are the basic vectors used for the production of both the wildtype and mutant GI's. In all site-directed mutagenesis experiments, described hereinafter, use was made of a gdDNA prepared from the single stranded form of pMa5-I and a suitable fragment of pMc5-I.

1. LYSINE-253→GLUTAMINE

For the construction of the gdDNA, the large SacI-XhoI fragment of pMc5-I and the following oligonucleotide primer were used:

5'-CCTGGTCGAACTGCGGGCCG-3'   (SEQ ID NO:16)

The mutant enzyme was well expressed; specific activity using xylose as a substrate was 96% that of wildtype EcoAmi (DSM) GI (Table 3).

Figure 12A:
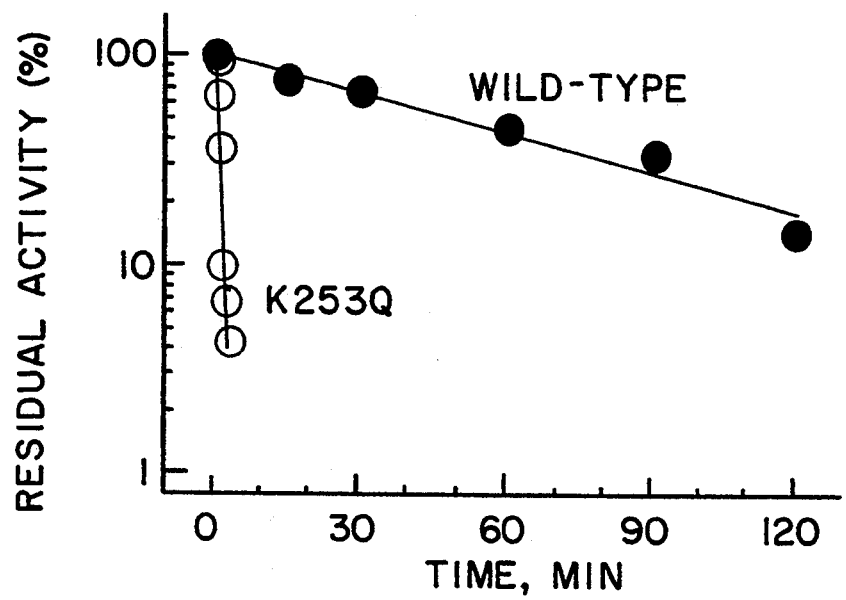
FIG. 12. Heat inactivation kinetics of EcoAmi(DSM) GI-mutant K253Q.
Figure 12B:
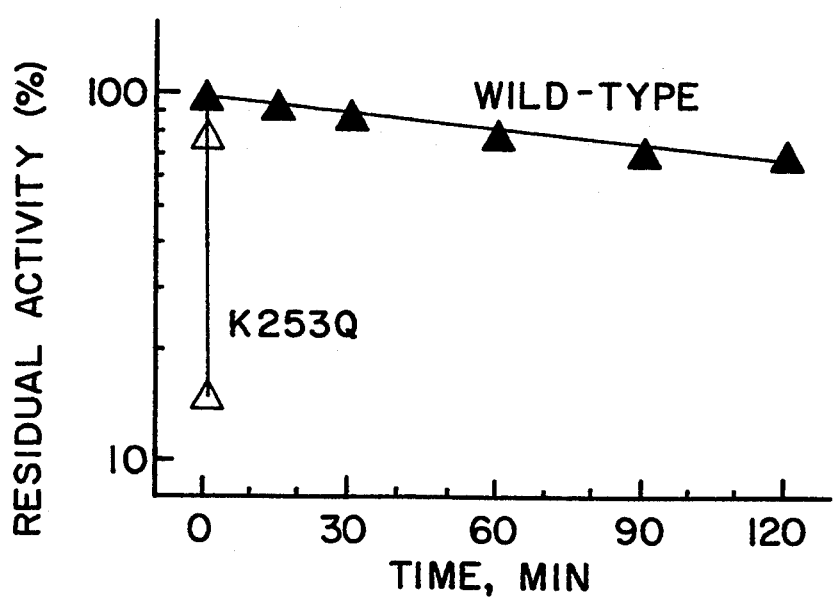

Heat-inactivation at 72° C. in 50 mM MOPS, pH 7.4 at 72° C., in the absence of metal, obeyed at first-order kinetics, and showed that the mutation provoked a 60- fold increase in the denaturation rate constant from $1.4 \times 10^{-2}$ min$^{-1}$ for wildtype to 0.9 min$^{-1}$ for K253Q (FIG. 12, Panel A). In the presence of 10 mM MgSO$_4$ at 85° C. in 50 mM MOPS, pH 6.5 at 85° C. (FIG. 12, Panel B), the first-order decay rate constant had a value of 1.2 min$^{-1}$ for K253Q, about 350 times higher than that of wildtype enzyme ($k_D = 3.4 \times 10^{-3}$ min$^{-1}$).

Figure 13A:
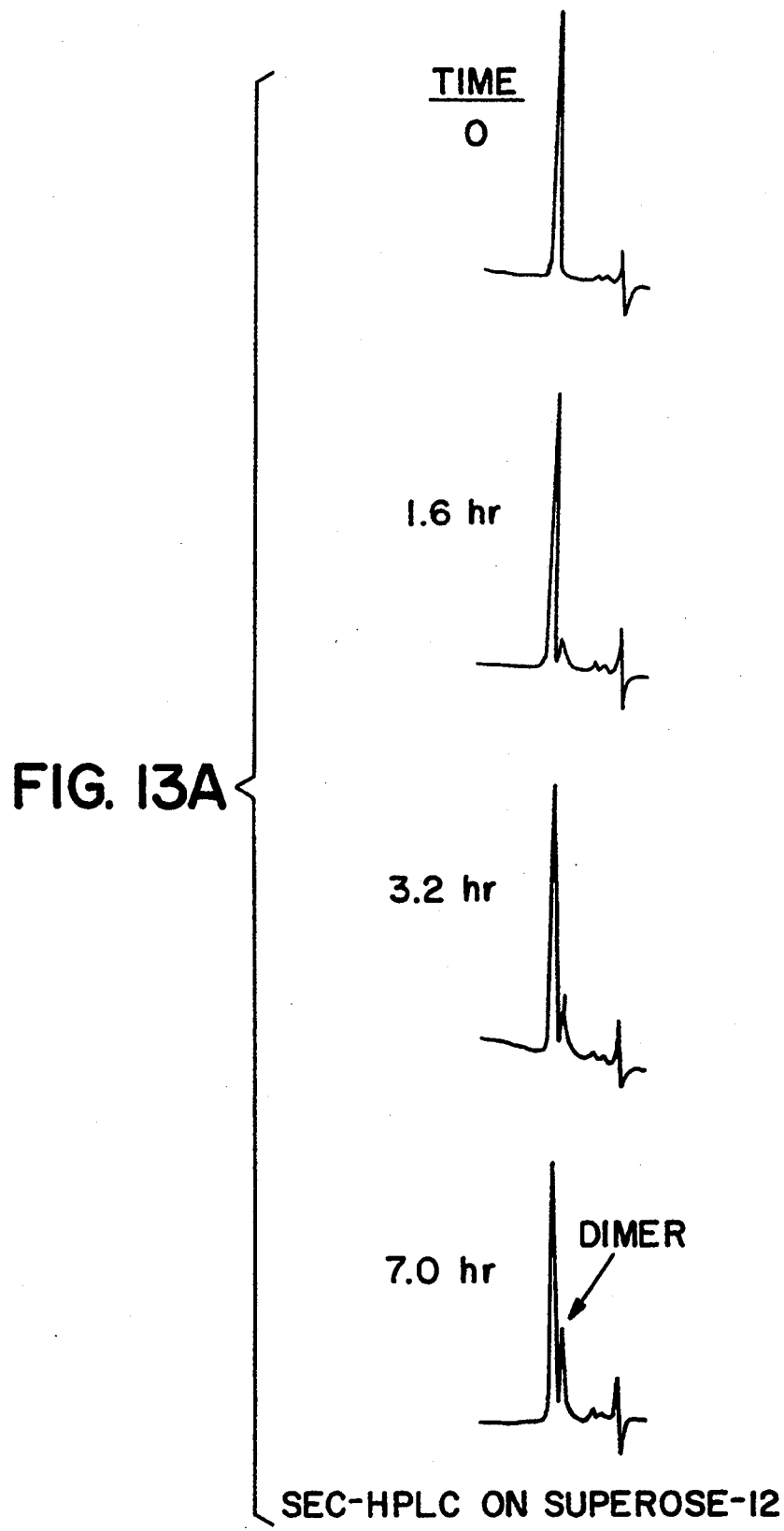
FIG. 13A-B. SEC-HPLC and Kinetics of tetramer-dimer dissociation at 25° C. in 5M urea of EcoAmi(DSM) GI mutant K253R.
Figure 13B:
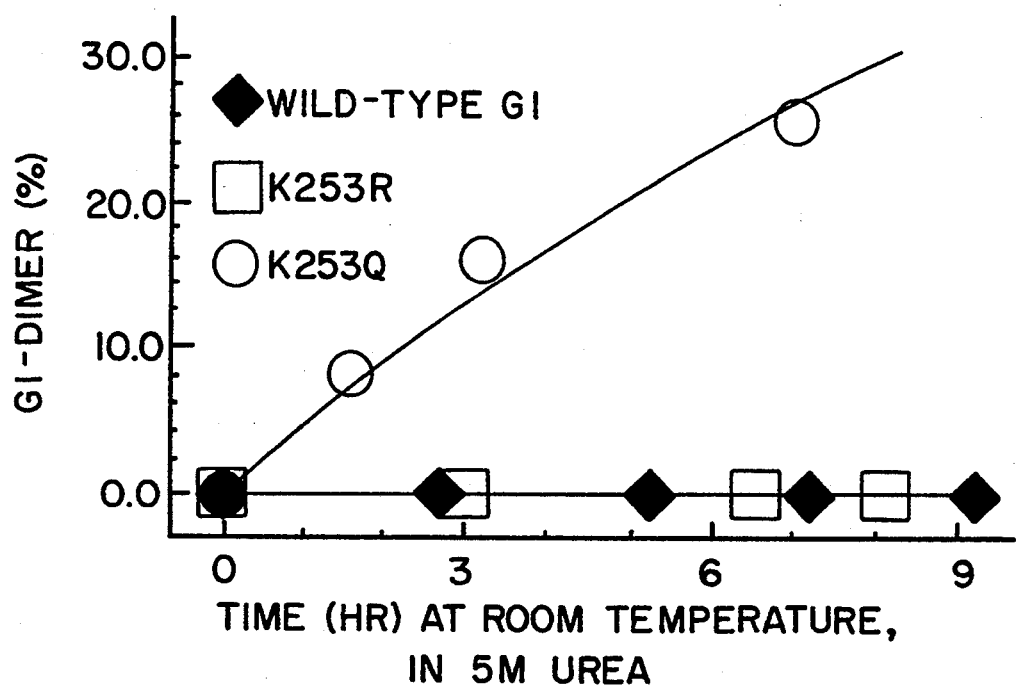
Figure 17:
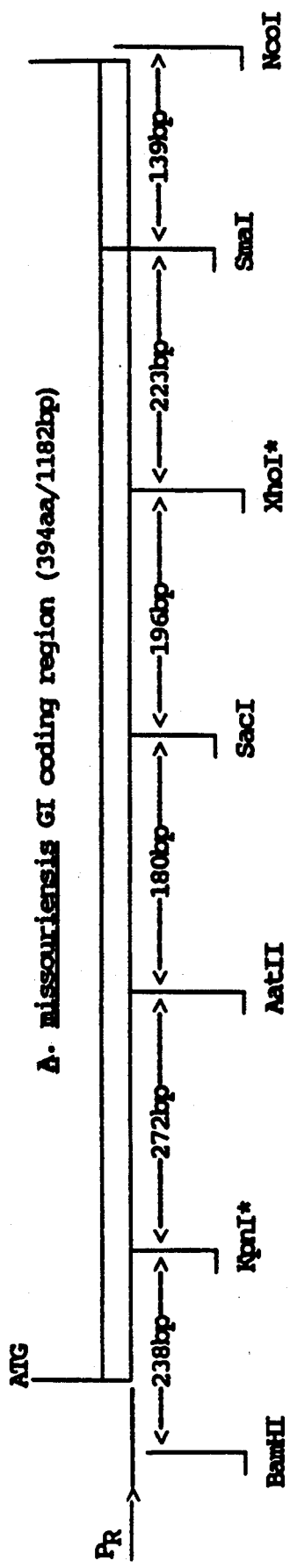
FIG. 17. Physical map of the glucose isomerase (GI) expression unit on pMa/c-I. The positions of relevant restriction sites, the P$_R$ promoter and the protein coding region are indicated. Asterisks indicate restriction sites introduced by site-directed mutagenesis.

Analysis of the oligomeric structure of the K253Q enzyme by size-exclusion chromatography revealed an intact tetramer. Prolonged incubation in 5 molar, cyanate-freed, urea in 0.2M borate, pH 8.5, 0.15M NaCl1, however, demonstrated that the K253Q mutant readily dissociated into dimers as shown in FIG. 13, Panel A; FIG. 13, Panel B, summarizes the data showing the progress curve for dimer formation for wildtype and mutant enzymes; the data show dissociation of tetramers into dimers in the mutant enzyme but not in the wildtype enzyme.

The experiments described above probe the structural basis of the stability of the EcoAmi(DSM) GI molecule. Specific alteration of residue K253 into glutamine introduces a temperature and also a urea sensitive mutation and consequently identifies a locus of essential interactions. A clear correlation is established between the susceptibility of the mutant to heat-inactivation and the extent of tetramer dissociation into dimers promoted by urea at room temperature.

2. LYSINE-253→>ARGININE

For the construction of the gdDNA, the large SacI-XhoI fragment of pMc5-I and the following oligonucleotide primer were used:

5'-CCTGGTCGAACCGCGGGCCG-3'    (SEQ ID NO:17)

The EcoAmi(DSM) GI mutant, K253R, was well expressed and displayed an enzymatic activity 120% that of wildtype's with xylose as a substrate (Table 3).

The thermostability of this mutant was tested in 50 mM (N-2-Hydroxyethylpiperazine-N'-2-ethanesulfonic acid) (EPPS), pH 7.5, 5 mM MgSO$_4$, at temperatures ranging from 82°-92° C. Table 4 lists the half-lives in hours for K253R and wildtype enzymes; the results demonstrate that over this temperature range K253R is consistently more stable than wildtype enzyme.

To assess the stability of the mutant K253R with regard to inactivation by glucose at high temperatures, both enzymes were incubated in the presence of 250 mM D-glucose at 60° C. in 12.5 mM potassium phosphate buffer, pH 7.7. Shown in FIG. 14 is the time course of inactivation for about 70 hours; the data clearly demonstrate the enhanced protection against inactivating-irreversible-chemical modification achieved in the K253R mutant as its half-life is increased 5-fold compared to wildtype's.

As a negative control, LYS-100 was mutated into arginine, in which case it was expected that, as mentioned earlier, a bad steric accomodation of the new residue would lead to a decrease of stability, although without affecting enzymatic activity.

3. LYSINE-100→>ARGININE

For the construction of the gdDNA, the large KpnI-AatII fragment of pMc5-I and the following oligonucleotide primer were used:

5'-CCGCCGTCCCGGAACACCGG-3'    (SEQ ID NO:18)

The specific activity of the K100R GI was 22 units per mg using xylose as a substrate. It is thus comparable to the activity of the wildtype EcoAmi(DSM) GI (24.5 units per mg). Heat inactivation of this mutant enzyme, however, proceeded about 100 times faster with $k_D = 0.3$ min$^{-1}$, in 50 mM EPPS, pH 7.5 at 84° C., 5 mM MgSO$_4$.

4. LYSINE-294→>ARGININE.

For the construction of the gdDNA, the large XhoI-SmaI fragment of pMc5-I and the following oligonucleotide primer were used:

5'-GGGGACGGCCGGTAGTCGAAG-3'    (SEQ ID NO:19)

The EcoAmi(DSM) GI mutant, K294R, was well expressed and displayed an enzymatic activity that was 85% of the wildtype's with xylose as a substrate (Table 3).

The thermostability of this mutant was tested in 50 mM (N-2-Hydroxyethylpiperazine-N'-2-ethanesulfonic acid) (EPPS), pH 7.5, 5 mM MgSO$_4$, at temperatures ranging from 82°-92° C. The half-lives in hours for K294R are listed in Table 4; the results demonstrate that over this temperature range K294R has approximately the same stability as the wildtype enzyme.

TABLE 3

Catalytic parameters of wildtype (WT) and mutant EcoAmi(DSM) GI with either D-xylose (coupled assay) or D-glucose as substrates.

| | Xylose | | | Glucose | |
|---|---|---|---|---|---|
| | Spa | Vmax | Km | Vmax | Km |
| WT-GI | 24.5 | 24.2 | 4.8 | 34.8 | 290 |
| K253R | 30.0 | 24.6 | 5.3 | 27.2 | 177 |
| K253Q | 23 | 15.1 | 4.4 | 29.2 | 210 |
| K100R | 22.2 | ND | ND | ND | ND |
| K294R | 20.5 | 13.8 | 4.5 | 25.8 | 187 |
| G70S;A73S;G74T | 28 | 24.9 | 5.3 | 39.2 | 235 |

Spa = specific activity in micromoles of product (D-xylulose or D-fructose) per minute (unit), per mg of enzyme.
$V_{max}$ is expressed in units per mg of enzyme.
$K_M$ is the Michaelis constant, expressed in mM.
ND = not determined.

5. LYSINE-309→>ARGININE (K309R)

Figure 18A:
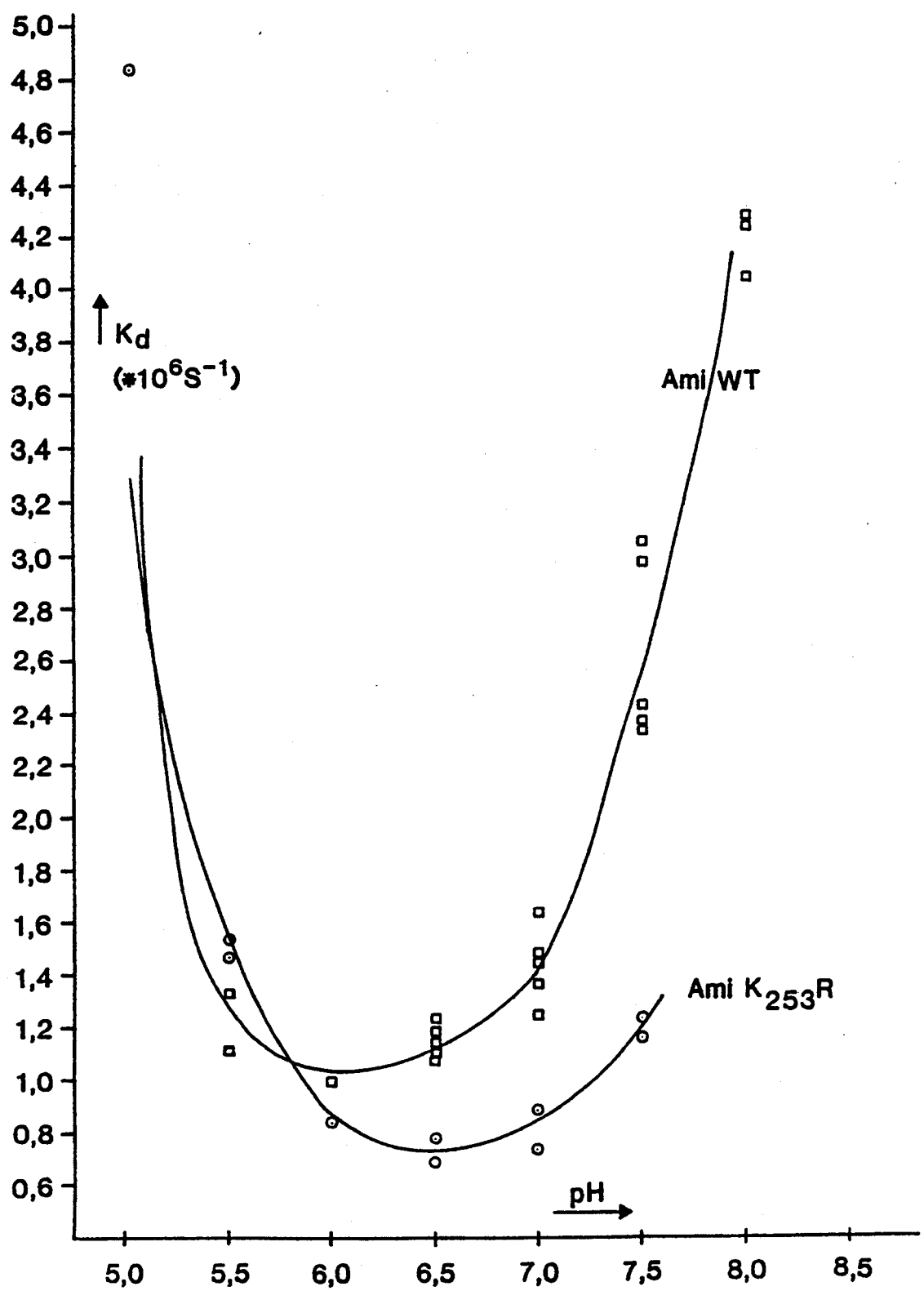
FIG. 18A. Shows the properties of the K253R glucose isomerase mutant at various pH, wherein separate k$_d$ measurements for AmiWT (□) and AmiK253R (o) are plotted. It can be seen that AmiK253R has an improved k$_d$ value over a wide pH range.
Figure 18B:
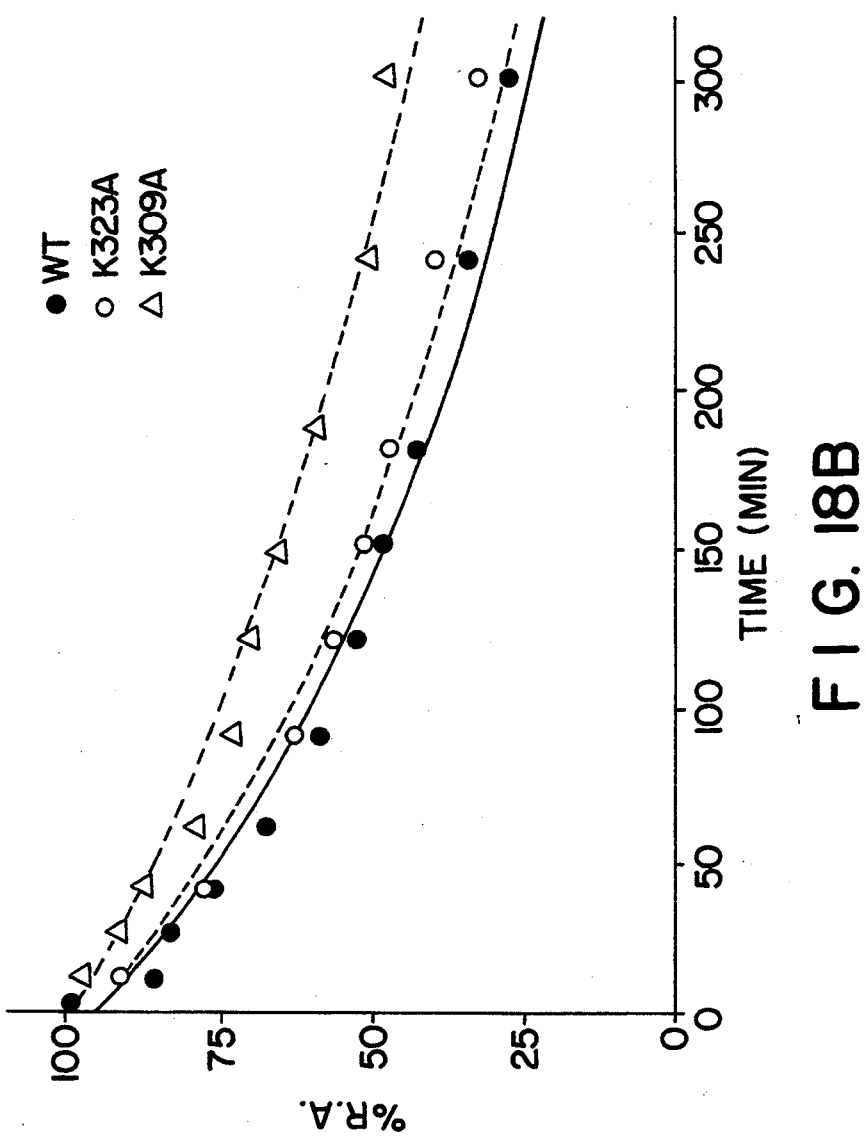
FIG. 18B. Shows the heat inactivation kinetics of wildtype glucose isomerase (solid circles) along with the mutants K323R (open circles) and K309R (open triangles).

The large SacI-XhoI fragment of pMc5-I was used with an oligonucleotide primer appropriate to make the conversion of the lysyl residue at position 309 to arginine, as described in 1.D.2. The mutated gene was expressed in *E. coli* as described above and purified by heat treatment. The specific activity was 22.2 units/mg and the thermal stability in the presence of 5 mM Mg$^{+2}$, 50 mM EPPS, pH 7.5 at 84° C. corresponds to a decay constant of $2.7 \times 10^{-3}$/min. The thermal inactivation curve of K309R at this temperature is shown in FIG. 18B.

The substitution occurs at a position located at the surface of an alpha-helix in an amphiphilic region which has an excess of positive charges, increasing the possibility glycosylation. Modification surface residues usually decreases stability while only marginally affecting activity and glycosylation properties may also be altered. However, the thermal stability of this mutant is higher than wild-type when measured under the same conditions, although the specific activity remains the same.

6. LYSINE 319→>ARGININE (K319R)

cDNA encoding this mutant was prepared as described for K309R above and the mutated gene expressed in *E. coli*. The measured specific activity was 20 units/mg and the thermostability constant at 84° C. in 50 mM EPPS, pH 7.5, 5 mM Mg$^{+2}$ ion was $2.5 \times 10^{-3}$ min. This lysine is also a conserved residue at the surface of an alpha-helix which is amphiphilic with an excess of positive charges. Glycosylation in this area should be affected. Modification of this residue increases stability while only marginally affecting the activity.

7. LYSINE 323→>ARGININE (K323R)

The mutated gene encoding this protein was prepared as described above for K309R and the gene was expressed *E. coli*. The specific activity was 22.3 units/mg and the thermostability, as determined under the above-described conditions gave it a decay constant of $4.0 \times 10^{-3}$/min, which is the same as wild-type within experimental error when measured under the same conditions. The heat in activation of K323R is also shown in FIG. 18B. This lysyl residue occurs in a surface region of an amphiphilic helix which has an excess of positive charges.

8. TRIPLE MUTANT K309R/K319R/K323R

The gene encoding this modified form was prepared as described for the individual mutants above. The mutated gene was expressed in *E. coli* and has the following heat inactivation characteristics. At 72° C. in the absence of metal the decay constant for this mutant is $8.7 \times 10^{-3}$/min ($t_{\frac{1}{2}}=87$ min). At 84° C. in the presence of 5 mM MgSO$_4$, the decay constant is $1.7 \times 10^{-3}$/min ($t_{\frac{1}{2}}=418$ min). The triple mutant title compound is extremely stable compared both to wild-type and to the individual mutants. In summary, 72° C. in the absence of metal ion:

K309R, $k_d=9.3 \times 10^{-3}$/min, $t_{\frac{1}{2}}=75$ min;

K319R, $k_d=8.9 \times 10^{-3}$/min, $t_{\frac{1}{2}}=78$ min;

K323R, kd=$13.5 \times 10^{-3}$/min, $t_{\frac{1}{2}}=51$ min;

wild-type, $k_d=11.8 \times 10^{-3}$, $t_{\frac{1}{2}}=59$ min.

It can be calculated that under these conditions each mutation contributes independently to a stabilizing effect, since the result of this relationship:

$75/59 \times 78/59 \times 51/59 = t_{\frac{1}{2}}(3)/59$ is that wherein $T_{178}$ is calculated at 86 min.

Similarly, at 84° C. in the presence of Mg$^{+2}$:

K309R, $k_d=2.6 \times 10^{-3}$/min; $t_{\frac{1}{2}}=271$ min;

K319R, $k_d=2.5 \times 10^{-3}$/min; $t_{\frac{1}{2}}=273$ min;

K323R, $k_d=4.0 \times 10^{-3}$/min; $t_{\frac{1}{2}}=172$ min;

wild-type, $K_d=4.2 \times 10^{-3}$/min; $t_{\frac{1}{2}}=167$ min.

Again, the theoretical calculation:
$271/167 \times 273/167 \times 172/167$ $t_{\frac{1}{2}}(3)/167$ which is based on an assumed independence of effect of each mutation leads to a calculated half-life of 456 min.

EXAMPLE 5 stabilisation of glucose isomerase through mutations within the monomer

Although mutations which would improve the stability of the monomer subunit, were with regard to Example 2 not very likely to affect tetramer stability of glucose isomerase some mutations in that direction have been performed. Three residues from helix B of the 8 stranded β-barrel of glucose isomerase monomer were mutated with the aim to stabilize this β-helix and indirectly stabilize the monomer. Glycine 70 was mutated into Serine, Alanine 73 was mutated into Serine and Glycine 74 was mutated into Threonine.

For the construction of the gdDNA, the large KpnI-AatII fragment of pMc5-I and the following oligonucleotide primer were used:

5'-GCCTTCTTGAAGGTCGAGATGATG-
    GAGTCGCGG-3'          (SEQ ID NO:20)

The EcoAmi(DSM) GI mutant, G70S;A73S;G74T, was well expressed and its specific activity that was 28 units per mg (115% of the wildtype) with xylose as a substrate (Table 3).

The thermostability of this mutant was tested in 50 mM (N-2-Hydroxyethylpiperazine-N'-2-ethanesulfonic acid) (EPPS), pH 7.5, 5 mM MgSO4, at temperatures ranging from 82°-92° C. The half-lives in hours for G70S;A73S;G74T are listed in Table 4; the results demonstrate that over this temperature range and under the conditions used, G70S;A73S;G74T is more stable than the wildtype enzyme, and also more stable than mutant K253R.

EXAMPLE 6

Production and purification of wildtype and mutant A. missouriensis glucose isomerase for application testing For production of *A. missouriensis* glucose isomerase in *E. coli*, use was made of the expression unit on the pMa type vector exclusively.

Transformants of glucose isomerase deficient *E. coli* strain K527 (thi, thr, leu, tonA, lacY, supE, xylA, $r_k^- m_k^+$), harbouring the *A. missouriensis* glucose isomerase gene encoding the wildtype protein or the desired mutant protein were grown in a medium composed of: yeast extract (20 g/l), Bacto tryptone ( 40 g/l), casamino acids ( 4 g/l), NaCl1 ( 10 g/l), and ampicillin (100 mg/l) for 16 hrs at 37° C. After centrifugation the cells were resuspended in a minimal volume of buffer consisting of 20 mM Tris, 10 mM EDTA, 50 mM glucose, pH 8.0. Lysozyme was then added to a final concentration of 1.5 g/l. After incubation at 37° C. for 30 minutes, the suspension was heated to 70° C. for 30 minutes. Next the suspension was cooled to room temperature and MgCl$_2$ and DNaseI were added to final concentrations of 20 mM and 1.5 mg/l, respectively, and incubated at 37° C. for another 30 minutes. Cellular debris were precipitated by centrifugation and the supernatant dialysed against 50 mM Tris (pH 7.5) overnight.

EXAMPLE 7

Immobilization of wildtype and mutant glucose isomerases

The enzyme solution can be immobilized on an ionic exchange resin. Before each experiment the ion exchange resins are regenerated by treatment of the resin with a 0.5 NaOH solution (>10 bedvolumes), water (until pH <8), a 10% NaCl solution (>10 bedvolumes) and water (>20 bedvolumes). Resins Lewatit MP500A (Bayer) and Amberlite IRA 904 (Rohm & Haas) were selected for the immobilisation of glucose isomerase. The adsorption of enzyme on these anion exchange resins occurs with high efficiency. There is a linear relationship between the adsorbed amount of enzyme and the activity of the application column.

10 g of the anion exchange resin (Cl⁻ form) is placed in 50 ml of buffer (50 mM Tris HCl pH 7.5). Purified glucose isomerase is added and allowed to bind overnight at 4° C. in a total volume of 100 ml with 50 mM Tris. HCl1 buffer (pH 7.5).

EXAMPLE 8

Application testing of wildtype and mutant glucose isomerases

The initial activity and the stability of the immobilized glucose isomerase and its mutant were determined by measuring the pump rate at 45% conversion as a function of time according to R. van Tilburg (Thesis: Engineering aspects of Biocatalysts in Industrial Starch Conversion Technology, Delftse Universitaire Pers, 1983). From this $K_o$ and $k_d$ can be calculated. $K_o$, a pseudo-first-order reaction rate constant is a measure for the enzyme activity. $k_d$, a first order decay constant, is a measure for the stability of the enzyme. Although the $k_d$ calculation has been described for gelatin-immobilized glucose isomerase only (R. van Tilburg, ibid.), the same calculations can be used for resin-immobilized glucose isomerase. The experimental conditions were: temperature: 70° C.; reactor: downflow packed bed; substrate: 3M glucose, 3 mM MgSO4, 3 mM Na2SO3; conversion: 45% fructose; pH 7.5 (measured at 35° C.); Ca: $\leq$3 ppm. Results for $k_d$ are shown in Table 5.

TABLE 5

Decay constants for wildtype and mutant glucose isomerase, immobilized on different resins.

| | $k_d (\times 10^6 \sec^{-1})$ Lewatit | $k_d (\times 10^6 \sec^{-1})$ Amberlite |
|---|---|---|
| Wildtype | 2.7 | 2.4 |
| K253R | 1.0 | 0.7 |
| K294R | 2.8 | 2.9 |
| K253Q | n.d. | 3.7 |
| (G70S;A73S;G74T) | 2.0 | 2.1 |

N.B.: Both wildtype and mutant enzymes were produced, purified, and immobilized according to the description in Examples 6 and 7.

It can be deduced from Table 5 that both mutant K253R and G70S;A73S;G74T have a significantly improved stability in the 70° C. application test. These results can be translated with a fair degree of accuracy into results that will be obtained if tests are carried out at a temperature customary in industry (R. van Tilburg, ibid.).

The low performance of mutant K253Q is an indication of the importance of a basic residue at position 253, as already deduced from the in vitro experiments described in Example 4. The Glutamine mutant probably does not form any hydrogen bond at all thereby destabilising the dimer-dimer contact.

Similarly the K294R mutant has a somewhat lower stability than the wildtype enzyme in accordance with the results obtained in the in vitro experiments.

The above results show that improvement of the dimer-dimer interface contact of glucose isomerase can result in an enzyme with superior behaviour in industrial applications. It will be clear that other residues involved in interface contacts can also be selected by one of ordinary skill. Residues which are susceptible to chemical modification or which do not show an optimal hydrogen bonding may be substituted by other amino acids according to the teaching of this specification.

Surprisingly mutations which are aimed at stabilizing the monomeric subunit also show a positive effect on tetramer stabilisation, as evidenced by the $k_d$ values observed for the mutant G70S;A73S;G74T.

In an attempt to rationalize these results one should bear in mind that substitution of Glycine residues in an α-helix can result in a decreased entropy of the unfolded state of a protein thereby rendering the protein more resistant to reversible unfolding and denaturation (Proteins, 1 (1986) 43–46). In doing so the susceptibility of glucose isomerase to chemical modification (and therefore irreversible denaturation) of (partially) unfolded protein might be significantly lowered, resulting in a more thermostable enzyme. Alternatively one may consider the fact that the mutations inserted in the mutant G70S;A73S;G74T are all more hydrophilic in nature and therefore likely to be favoured on the exposed surface of helix B. This can as such lead to enhanced stability of the monomer against reversible unfolding. As stated previously this can lower the susceptibility of the tetrameric protein against irreversible denaturation.

The mutations exemplified in this Example can be introduced in a similar way in all α-helices of glucose isomerase. Helix regions as determined from the 3D structure of A. missouriensis glucose isomerase (F. Rey et al., ibid.) are at positions: α1 35–47, α2 64–80, α3 108–128, α4 150–173, α5 195–206, 227–239, α7 264–276, α8 300–328. Substitution of Glycine residues, introduction of hydrophobic residues and introduction of Proline residues at the amino terminus of an α-helix can be envisaged.

Both engineered mutations K253R and G70S;A73S;G74T lead to improved heat stabilization relative to wildtype glucose isomerase. However, mutant K253R appears more stable than mutant G70S;A73S;G74T in the application tests contrary to the results of the in vitro experiments described in Example 4. This can be seen as a reflection of the fact that results obtained under laboratory conditions are only to a certain degree predictive for the performance of an enzyme under application conditions. Possibly the high glucose concentration used under application conditions and the glycation process, which is dependent on glucose concentration, are responsible for this phenomenon.

EXAMPLE 9 properties of mutant glucose isomerase at different pH

Comparative tests were carried out with mutant K253R and WT A. missouriensis glucose isomerase at different pH values. Enzyme preparations of K253R and WT were immobilized on Lewatit as described in Example 7 and subjected to an isomerisation test as described in Example 8. Conditions were as derived from R. van Tilburg (ibid.) with glucose syrups at various pH. FIG. 18 shows the $k_d$ values of both enzymes as a function of pH. It can be seen that mutant K253R exhibits an improved $k_d$ at values below pH 7.5 up to a value of pH 5.8.Measurements were performed at least in duplicate. Thus, mutant K253R shows not only superior behaviour in industrial applications at higher temperature (higher conversion rate), but also at lower pH (better stability of the product fructose).

EXAMPLE 10

Cloning and sequencing of glucose isomerase genes from other bacterial strains

In order to obtain amino acid sequence information on glucose isomerase from different bacteria, the genes encoding the glucose isomerase were isolated from the chromosome of the respective bacteria via molecular cloning in E. Coli.

The following bacteria, several of which are known to produce industrially applied enzymes, were selected for this purpose:
  Arthrobacter species
  *Streptomyces violaceoruber* LMG 7183
  *Streptomyces thermovulgaris* DSM 40444
  *Streptomyces murinus* DSM 40091
  Ampullariella species ATCC 31351

Chromosomal DNA for all species mentioned was isolated and purified essentially as described by Hopwood (ibid.)

For Arthrobacter, *S. violaceoruber*, and Ampullariella partial digestion with restriction endonuclease Sau3AI and cloning of the resulting fragments in *E. coli* was performed exactly as described for *A. missouriensis* in Example 1. Chromosomal DNA from *S. murinus* and *S. thermovulgaris* was digested completely with PstI followed by ligation into pECOR251 as described in Example 1.

Colonies containing the desired glucose isomerase gene were detected by colony hybridization using a 712 bp MluI restriction fragment from the *A. missouriensis* glucose isomerase gene or a 853 bp SacII restriction fragment located within the *S. violaceoruber* glucose isomerase gene.

The recombinant plasmids containing the glucose isomerase genes from the different bacteria were further characterized by restriction mapping as described for the *A. missouriensis* glucose isomerase gene. Nucleotide sequence analysis of the protein coding regions was performed using the chemical method devised by Maxam and Gilbert (ibid.). The clone containing the *S. thermovulgaris* glucose isomerase gene turned out to be incomplete: only the coding sequence upto amino acid 346 (equivalent to position 351 of *A. missouriensis* glucose isomerase) has therefore been established.

It should be noted that the amino acid sequence of the Ampullariella sp. glucose isomerase differs from the published sequence in that proline 177 of the published sequence was found to be an arginine.

The results of this example are summarized in FIG. 21, in which the amino acid sequences, derived from the established nucleotide sequences, are aligned as to maximally display the mutual homology.

EXAMPLE 11

Expression and Mutagenesis of Ampullariella sp. glucose isomerase

For expression of Ampullariella sp. glucose isomerase in *E. coli* use was made of the efficient expression unit already available for *A. missouriensis* glucose isomerase. In fact the *A. missouriensis* expression vector was mutated using restriction fragments from the Ampullariella sp. glucose isomerase gene covering all nucleotide and resulting amino acid differences of the coding regions of the two genes: a gapped duplex molecule was formed consisting of single-stranded DNA of pMa-I and the 4107 bp BstEII/NcoI fragment of pMc-I, a 124 bp BstEII/ApaLI fragment and a 1059 bp ApaLI/BssHII fragment, the latter two fragments being derived from the Ampullariella sp. glucose isomerase gene. The procedure was continued essentially as described in Example 1, including a renewed nucleotide sequence determination of the gene to check for unwanted alterations.

Thus the correct plasmid was found and named pMc-GIamp1.

The amino acid sequence comparison showed that the Ampullariella glucose isomerase, like the *A. missouriensis* glucose isomerase, contained a lysine residue at the equivalent position 253. Therefore a mutant of Ampullariella sp. glucose isomerase wherein lysine (K) at position 253 was replaced by arginine (R) was generated using a gapped duplex molecule formed by annealing single-stranded pMc-GIamp1 DNA with BamHI/HindIII digested pMa-GIamp1 and the phosphorylated mutagenic oligonucleotide:

5'-
  AGGTCCTGGT-
  CGAACCGCGGGCCGTGCTGG-3'        (SEQ ID NO:21)

The procedure following the annealing step, i.e. selection and analysis of the resulting mutant, was performed exactly as described in Example 1.

EXAMPLE 12

Figure 20:
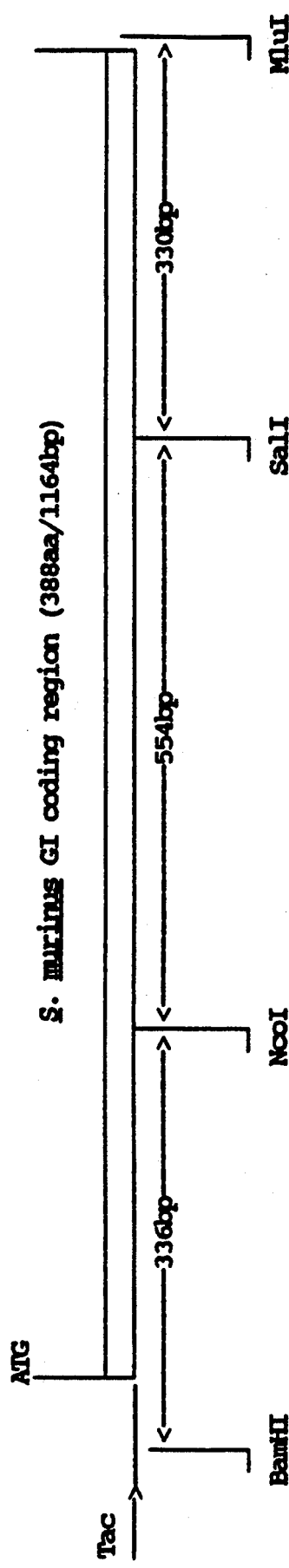
FIG. 20. Physical map of the glucose isomerase (GI) expression unit on pMa/c-GIsmuI. The positions of relevant restriction sites, the Tac promoter and the protein coding region are indicated.

Expression and site directed mutagenesis of streptomyces murinus glucose isomerase Expression of the Streptomyces murinus glucose isomerase gene was achieved by placing the gene downstream of the Tac promoter of plasmid pMaT5. pMaT5 is a derivative of plasmid pMa5$P_R$, in which the lambda $P_R$ promoter is replaced by the regulatable Tac promoter (H. de Boer Proc.Natl.Acad. Sci.USA 60 (1983) 21). The structure of this expression vector is indicated in FIG. 15a/c. A 1280 bp BstXI/MluI restriction fragment containing the complete *Streptomyces murinus* glucose isomerase gene as treated with DNA polymerase I (Klenow fragment) to convert the fragment boundaries to blunt ends, and subsequently was ligated into pUC19. Next the gene was excised again using BamHI and HindIII, and inserted into BamHI/HindIII digested pMc5T. The resulting plasmid was named pMc-GIsmu1. The nucleotide and derived amino acid sequence of the *Streptomyces murinus* glucose isomerase and the structure of the expression unit are shown in FIGS. 19 and 20, respectively.

Also *S. murinus* glucose isomerase has a lysine residue in the protein sequence at position 253, equivalent to K253 in *A. missouriensis*. The mutation resulting in a substitution of lysine 253 (K) into arginine (R) in the *Streptomyces murinus* glucose isomerase was introduced using a gapped duplex molecule consisting of single-stranded pMc-GIsmu1 DNA, BamHI/HindIII digested pMa5T, and the phosphorylated mutagenic oligonucleotide:

5'-GGTCCTGGTCGTACCGGATGCC-
  GGACTGG-3'                    (SEQ ID NO:22)

The procedure following the annealing step, i.e. selection and analysis of the resulting mutant, was performed essentially as described in Example 1.

It will be appreciated that the invention is not restricted to the above suggested and illustrated mutations. Although the foregoing invention has been described in some detail by way of illustration and example for the purposes of clarity of understanding, it will be obvious that certain changes and modifications may be practised within the scope of the appended claims.

We claim:

1. A modified glucose isomerase comprising a multimeric structure, each monomeric unit of said structure having an amino acid sequence which differs from a corresponding wild-type glucose isomerase obtained from *Actinoplanes missouriensis* by replacement of at least one amino acid by a different amino acid, wherein said replacement is selected from the group consisting of
    replacing Lys 253 by Arg 253;
    replacing Gly 70 by Ser 70;
    replacing Ala 73 by Ser 73;
    replacing Gly 74 by Thr 74;
    replacing Lys 309 by Arg 309;
    replacing Lys 319 by Arg 319; and
    replacing Lys 323 by Arg 323;
said replacement not altering the glucose isomerase activity, and said modified glucose isomerase exhibiting enhanced interaction resulting in enhanced resistance of said modified glucose isomerase toward covalent binding of substrate molecules and thermostability under standard application conditions as compared to said corresponding wild-type enzyme.

2. The modified glucose isomerase of claim 1 wherein Lys253 is replaced by Arg253.

3. The modified glucose isomerase of claim 1 wherein Gly70 is replaced by Ser70; Ala73 is replaced by Ser73; and Gly74 is replaced by Thr74.

4. The modified glucose isomerase of claim 1 wherein Lys309 is replaced by Arg309; or Lys319 is replaced by Arg319; or Lys323 is replaced by Arg323.

5. The modified glucose isomerase of claim 1 wherein Lys309 is replaced by Arg309; and Lys319 is replaced by Arg319; and Lys323 is replaced by Arg323.

6. The modified glucose isomerase of claim 1 in immobilized form.

7. A method to produce fructose syrup, which method comprises contacting a preparation containing glucose with the glucose isomerase of claim 1 under conditions effective to convert a desired amount of glucose to fructose.

8. The modified glucose isomerase according to claim 1 wherein the multimeric structure is a tetramer.

* * * * *

SEQUENCE LISTING ( 1 ) GENERAL INFORMATION:

( i i i ) NUMBER OF SEQUENCES: 22

( 2 ) INFORMATION FOR SEQ ID NO:1:

( i ) SEQUENCE CHARACTERISTICS:
    ( A ) LENGTH: 3803 base pairs
    ( B ) TYPE: nucleic acid
    ( C ) STRANDEDNESS: double
    ( D ) TOPOLOGY: circular ( i i i ) HYPOTHETICAL: NO ( x ) PUBLICATION INFORMATION:
    ( A ) AUTHORS: Stanssens, P
    ( G ) DATE: july-1987

( x i ) SEQUENCE DESCRIPTION: SEQ ID NO:1:

| | | | | | |
|---|---|---|---|---|---|
| AATTCACCTC | GAAAGCAAGC | TGATAAACCG | ATACAATTAA | AGGCTCCTTT | TGGAGCCTTT | 60 |
| TTTTTGGAG | ATTTTCAACG | TGAAAAAATT | ATTATTCGCA | ATTCCAAGCT | AATTCACCTC | 120 |
| GAAAGCAAGC | TGATAAACCG | ATACAATTAA | AGGCTCCTTT | TGGAGCCTTT | TTTTTGGAG | 180 |
| ATTTTCAACG | TGAAAAAATT | ATTATTCGCA | ATTCCAAGCT | CTGCCTCGCG | CGTTTCGGTG | 240 |
| ATGACGGTGA | AAACCTCTGA | CACATGCAGC | TCCCGGAGAC | GGTCACAGCT | TGTCTGTAAG | 300 |
| CGGATGCAGA | TCACGCGCCC | TGTAGCGGCG | CATTAAGCGC | GGCGGGTGTG | GTGGTTACGC | 360 |
| GCAGCGTGAC | CGCTACACTT | GCCAGCGCCC | TAGCGCCCGC | TCCTTTCGCT | TTCTTCCCTT | 420 |
| CCTTTCTCGC | CACGTTCGCC | GGCTTTCCCC | GTCAAGCTCT | AAATCGGGGG | CTCCCTTTAG | 480 |
| GGTTCCGATT | TAGTGCTTTA | CGGCACCTCG | ACCCCAAAAA | ACTTGATTAG | GGTGATGGTT | 540 |
| CACGTAGTGG | GCCATCGCCC | TGATAGACGG | TTTTTCGCCC | TTTGACGTTG | GAGTCCACGT | 600 |
| TCTTTAATAG | TGGACTCTTG | TTCCAAACTG | GAACAACACT | CAACCCTATC | TCGGTCTATT | 660 |
| CTTTTGATTT | ATAAGGGATT | TTGCCGATTT | CGGCCTATTG | GTTAAAAAAT | GAGCTGATTT | 720 |
| AACAAAAATT | TAACGCGAAT | TTTAACAAAA | TATTAACGTT | TACAATTTGA | TCTGCGCTCG | 780 |
| GTCGTTCGGC | TGCGGCGAGC | GGTATCAGCT | CACTCAAAGG | CGGTAATACG | GTTATCCACA | 840 |
| GAATCAGGGG | ATAACGCAGG | AAAGAACATG | TGAGCAAAAG | GCCAGCAAAA | GGCCAGGAAC | 900 |
| CGTAAAAAGG | CCGCGTTGCT | GGCGTTTTTC | CATAGGCTCC | GCCCCCCTGA | CGAGCATCAC | 960 |
| AAAAATCGAC | GCTCAAGTCA | GAGGTGGCGA | AACCCGACAG | GACTATAAAG | ATACCAGGCG | 1020 |
| TTTCCCCCTG | GAAGCTCCCT | CGTGCGCTCT | CCTGTTCCGA | CCCTGCCGCT | TACCGGATAC | 1080 |
| CTGTCCGCCT | TTCTCCCTTC | GGGAAGCGTG | GCGCTTTCTC | ATAGCTCACG | CTGTAGGTAT | 1140 |
| CTCAGTTCGG | TGTAGGTCGT | TCGCTCCAAG | CTGGGCTGTG | TGCACGAACC | CCCCGTTCAG | 1200 |
| CCCGACCGCT | GCGCCTTATC | CGGTAACTAT | CGTCTTGAGT | CCAACCCGGT | AAGACACGAC | 1260 |
| TTATCGCCAC | TGGCAGCAGC | CACTGGTAAC | AGGATTAGCA | GAGCGAGGTA | TGTAGGCGGT | 1320 |
| GCTACAGAGT | TCTTGAAGTG | GTGGCCTAAC | TACGGCTACA | CTAGAAGGAC | AGTATTTGGT | 1380 |
| ATCTGCGCTC | TGCTGAAGCC | AGTTACCTTC | GGAAAAAGAG | TTGGTAGCTC | TTGATCCGGC | 1440 |
| AAACAAACCA | CCGCTGGTAG | CGGTGGTTTT | TTTGTTTGCA | AGCAGCAGAT | TACGCGCAGA | 1500 |
| AAAAAAGGAT | CTCAAGAAGA | TCCTTTGATC | TTTTCTACGG | GGTCTGACGC | TCAGTGGAAC | 1560 |
| GAAAACTCAC | GTTAAGGGAT | TTTGGTCATG | AGATTATCAA | AAAGGATCTT | CACCTAGATC | 1620 |
| CTTTTAAATT | AAAAATGAAG | TTTTAAATCA | ATCTAAAGTA | TATATGAGTA | AACTTGGTCT | 1680 |
| GACAGTTACC | AATGCTTAAT | CAGTGAGGCA | CCTATCTCAG | CGATCTGTCT | ATTTCGTTCA | 1740 |

```
TCCATAGTTG CCTGACTCCC CGTCGTGTAG ATAACTACGA TACGGGAGGG CTTACCATCT    1800
GGCCCCAGTG CTGCAATGAT ACCGCGAGAC CCACGCTCAC CGGCTCCAGA TTTATCAGCA    1860
ATAAACCAGC CAGCCGGAAG GGCCGAGCGC AGAAGTGGTC CTGCAACTTT ATCCGCCTCC    1920
ATCCAGTCTA TTAATTGTTG CCGGGAAGCT AGAGTAAGTA GTTCGCCAGT TAATAGTTTG    1980
CGCAACGTTG TTGCCATTGC TGCAGGCATC GTGGTGTCAC GCTCGTCGTT TGGTATGGCT    2040
TCATTCAGCT CCGGTTCCCA ACGATCAAGG CGAGTTACAT GATCCCCAT GTTGTGCAAA     2100
AAAGCGGTTA GCTCCTTCGG TCCTCCGATC GTTGTCAGAA GTAAGTTGGC CGCAGTGTTA    2160
TCACTCATGG TTATGGCAGC ACTGCATAAT TCTCTTACTG TCATGCCATC CGTAAGATGC    2220
TTTTCTGTGA CTGGTGAGTA CTCAACCAAG TCATTCTGAG AATAGTGTAT GCGGCGACCG    2280
AGTTGCTCTT GCCCGGCGTC AACACGGGAT AATACCGCGC CACATAGCAG AACTTTAAAA    2340
GTGCTCATCA TTGGAAAACG TTCTTCGGGG CGAAAACTCT CAAGGATCTT ACCGCTGTTG    2400
AGATCCAGTT CGATGTAACC CACTCGTGCA CCCAACTGAT CTTCAGCATC TTTTACTTTC    2460
ACCAGCGTTT CTGGGTGAGC AAAAACAGGA AGGCAAAATG CCGCAAAAAA GGGAATAAGG    2520
GCGACACGGA AATGTTGAAT ACTCATACTC TTCCTTTTTC AATATTATTG AAGCAGACAG    2580
TTTTATTGTT CATGATGATA TATTTTTATC TTGTGCAATG TAACATCAGA GATTTTGAGA    2640
CACAACGTGG CTTTGTTGAA TAAATCGAAC TTTTGCTGAG TTGACTCCCC GCGCGCGATG    2700
GGTCGAATTT GCTTTCGAAA AAAAGCCCG CTCATTAGGC GGGCTAAAAA AAGCCCGCT      2760
CATTAGGCGG GCTCGAATTT CTGCCATTCA TCCGCTTATT ATCACTTATT CAGGCGTAGC    2820
AACCAGGCGT TAAGGGCAC CAATAACTGC CTTAAAAAAA TTACGCCCCG CCTGCCACT      2880
CATCGCAGTA CTGTTGTAAT TCATTAAGCA TTCTGCCGAC ATGGAAGCCA TCACAGACGG    2940
CATGATGAAC CTGAATCGCC AGCGGCATCA GCACCTTGTC GCCTTGCGTA TAATATTTGC    3000
CCATAGTGAA AACGGGGGCG AAGAAGTTGT CCATATTCGC CACGTTTAAA TCAAAACTGG    3060
TGAAACTCAC CCAGGGATTG GCTGAGACGA AAAACATATT CTCAATAAAC CCTTTAGGGA    3120
AATAGGCCAG GTTTTCACCG TAACACGCCA CATCTTGCGA ATATATGTGT AGAAACTGCC    3180
GGAAATCGTC GTGGTATTCA CTCCAGAGCG ATGAAAACGT TCAGTTTGC TCATGGAAAA     3240
CGGTGTAACA AGGGTGAACA CTATCCCATA TCACCAGCTC ACCGTCTTTC ATTGCCATAC    3300
GAAATTCCGG ATGAGCATTC ATCAGGCGGG CAAGAATGTG AATAAAGGCC GGATAAAACT    3360
TGTGCTTATT TTTCTTTACG GTCTTTAAAA AGGCCGTAAT ATCCAGCTAA ACGGTCTGGT    3420
TATAGGTACA TTGAGCAACT GACTGAAATG CCTCAAAATG TTCTTTACGA TGCCATTGGG    3480
ATATATCAAC GGTGGTATAT CCAGTGATTT TTTTCTCCAT TTTAGCTTCC TTAGCTCCTG    3540
AAAATCTCGA TAACTCAAAA AATACGCCCG GTAGTGATCT TATTTCATTA TGGTGAAAGT    3600
TGGAACCTCT TACGTGCCGA TCAACGTCTC ATTTTCGCCA AAAGTTGGCC CAGGGCTTCC    3660
CGGTATCAAC AGGGACACCA GGATTTATTT ATTCTGCGAA GTGATCTTCC GTCACAGGTA    3720
TTTATTCGAA GACGAAAGGG CATCGCGCGC GGGGAATTCC CGGGGATCCG TCGACCTGCA    3780
GCCAAGCTTG GTCTAGAGGT CGA                                            3803
```

( 2 ) INFORMATION FOR SEQ ID NO:2:

( i ) SEQUENCE CHARACTERISTICS:
        ( A ) LENGTH: 129 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO

-continued ( v i ) ORIGINAL SOURCE:
    ( A ) ORGANISM: Bacteriophage lambda ( i x ) FEATURE:
    ( A ) NAME/KEY: promoter
    ( B ) LOCATION: 1..129

( x i ) SEQUENCE DESCRIPTION: SEQ ID NO:2:

```
GAATTCCGCA AGGGATAAAT ATCTAACACC GTGCGTGTTG ACTATTTTAC CTCTGGCGGT      60

GATAATGGTT GCATGTACTA AGGAGGTTGT ATGGAACAAC GCATAACCCT GAAAGATAGC     120

TTGGGATCC                                                             129
```

( 2 ) INFORMATION FOR SEQ ID NO:3:

( i ) SEQUENCE CHARACTERISTICS:
        ( A ) LENGTH: 109 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i x ) FEATURE:
        ( A ) NAME/KEY: promoter
        ( B ) LOCATION: 1..109

( x i ) SEQUENCE DESCRIPTION: SEQ ID NO:3:

```
GAATTCGAGC TCGAGCTTAC TCCCCATCCC CCTGTTGACA ATTAATCATC GGCTCGTATA      60

ATGTGTGGAA TTGTGAGCGG ATAACAATTT CACACAGGAA ACAGGATCC                 109
```

( 2 ) INFORMATION FOR SEQ ID NO:4:

( i ) SEQUENCE CHARACTERISTICS:
        ( A ) LENGTH: 1182 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Actinoplanes missouriensis
        ( B ) STRAIN: DSM 4643

( i x ) FEATURE:
        ( A ) NAME/KEY: CDS
        ( B ) LOCATION: 1..1182
        ( C ) IDENTIFICATION METHOD: experimental
        ( D ) OTHER INFORMATION: /ECnumber=5.3.1.5
            / product="xylose isomerase (glucose isomerase)"
            / evidence=EXPERIMENTAL
            / standardname="D-xylose ketol isomerase"

( x i ) SEQUENCE DESCRIPTION: SEQ ID NO:4:

```
GTG TCT GTC CAG GCC ACA CGC GAA GAC AAG TTC TCC TTC GGT CTC TGG       48
Val Ser Val Gln Ala Thr Arg Glu Asp Lys Phe Ser Phe Gly Leu Trp
 1           5                  10                  15

ACC GTT GGA TGG CAG GCT CGT GAC GCG TTC GGT GAC GCC ACG CGT ACG       96
Thr Val Gly Trp Gln Ala Arg Asp Ala Phe Gly Asp Ala Thr Arg Thr
            20                  25                  30

GCA CTC GAC CCG GTC GAG GCC GTG CAC AAG CTC GCT GAG ATC GGC GCC      144
Ala Leu Asp Pro Val Glu Ala Val His Lys Leu Ala Glu Ile Gly Ala
        35                  40                  45

TAC GGC ATC ACG TTC CAC GAC GAC GAC CTG GTG CCC TTC GGC TCG GAC      192
```

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
| Tyr | Gly | Ile | Thr | Phe | His | Asp | Asp | Leu | Val | Pro | Phe | Gly | Ser | Asp |     |     |
|     | 50  |     |     |     | 55  |     |     |     |     | 60  |     |     |     |     |     |     |
| GCC | CAG | ACC | CGC | GAC | GGC | ATC | ATC | GCG | GGC | TTC | AAG | AAG | GCG | CTC | GAC | 240 |
| Ala | Gln | Thr | Arg | Asp | Gly | Ile | Ile | Ala | Gly | Phe | Lys | Lys | Ala | Leu | Asp |     |
| 65  |     |     |     | 70  |     |     |     |     | 75  |     |     |     |     |     | 80  |     |
| GAG | ACC | GGC | CTG | ATC | GTC | CCG | ATG | GTG | ACC | ACC | AAC | CTC | TTC | ACC | CAC | 288 |
| Glu | Thr | Gly | Leu | Ile | Val | Pro | Met | Val | Thr | Thr | Asn | Leu | Phe | Thr | His |     |
|     |     |     |     | 85  |     |     |     |     | 90  |     |     |     |     | 95  |     |     |
| CCG | GTG | TTC | AAG | GAC | GGC | GGC | TTC | ACC | AGC | AAC | GAC | CGT | TCC | GTG | CGG | 336 |
| Pro | Val | Phe | Lys | Asp | Gly | Gly | Phe | Thr | Ser | Asn | Asp | Arg | Ser | Val | Arg |     |
|     |     |     | 100 |     |     |     |     | 105 |     |     |     |     | 110 |     |     |     |
| CGC | TAC | GCG | ATC | CGC | AAG | GTG | CTG | CGC | CAG | ATG | GAC | CTC | GGC | GCC | GAG | 384 |
| Arg | Tyr | Ala | Ile | Arg | Lys | Val | Leu | Arg | Gln | Met | Asp | Leu | Gly | Ala | Glu |     |
|     |     | 115 |     |     |     | 120 |     |     |     |     | 125 |     |     |     |     |     |
| CTG | GGC | GCG | AAG | ACG | CTC | GTC | CTC | TGG | GGC | GGC | CGC | GAG | GGC | GCC | GAG | 432 |
| Leu | Gly | Ala | Lys | Thr | Leu | Val | Leu | Trp | Gly | Gly | Arg | Glu | Gly | Ala | Glu |     |
|     | 130 |     |     |     |     | 135 |     |     |     |     | 140 |     |     |     |     |     |
| TAC | GAC | TCG | GCC | AAG | GAC | GTC | AGC | GCC | GCC | CTC | GAC | CGC | TAC | CGC | GAG | 480 |
| Tyr | Asp | Ser | Ala | Lys | Asp | Val | Ser | Ala | Ala | Leu | Asp | Arg | Tyr | Arg | Glu |     |
| 145 |     |     |     |     | 150 |     |     |     |     | 155 |     |     |     |     | 160 |     |
| GCG | CTC | AAC | CTG | CTC | GCG | CAG | TAC | TCC | GAG | GAC | CGC | GGT | TAC | GGC | CTG | 528 |
| Ala | Leu | Asn | Leu | Leu | Ala | Gln | Tyr | Ser | Glu | Asp | Arg | Gly | Tyr | Gly | Leu |     |
|     |     |     |     | 165 |     |     |     |     | 170 |     |     |     |     | 175 |     |     |
| CGC | TTC | GCC | ATC | GAG | CCG | AAG | CCG | AAC | GAG | CCC | CGC | GGC | GAC | ATC | CTG | 576 |
| Arg | Phe | Ala | Ile | Glu | Pro | Lys | Pro | Asn | Glu | Pro | Arg | Gly | Asp | Ile | Leu |     |
|     |     |     | 180 |     |     |     |     | 185 |     |     |     |     | 190 |     |     |     |
| CTC | CCG | ACC | GCC | GGC | CAC | GCC | ATC | GCG | TTC | GTG | CAG | GAG | CTG | GAG | CGT | 624 |
| Leu | Pro | Thr | Ala | Gly | His | Ala | Ile | Ala | Phe | Val | Gln | Glu | Leu | Glu | Arg |     |
|     |     | 195 |     |     |     | 200 |     |     |     |     | 205 |     |     |     |     |     |
| CCC | GAG | CTC | TTC | GGC | ATC | AAC | CCG | GAG | ACC | GGG | CAC | GAG | CAG | ATG | TCG | 672 |
| Pro | Glu | Leu | Phe | Gly | Ile | Asn | Pro | Glu | Thr | Gly | His | Glu | Gln | Met | Ser |     |
| 210 |     |     |     |     | 215 |     |     |     |     | 220 |     |     |     |     |     |     |
| AAC | CTC | AAC | TTC | ACC | CAG | GGC | ATC | GCC | CAG | GCG | CTG | TGG | CAC | AAG | AAG | 720 |
| Asn | Leu | Asn | Phe | Thr | Gln | Gly | Ile | Ala | Gln | Ala | Leu | Trp | His | Lys | Lys |     |
| 225 |     |     |     |     | 230 |     |     |     |     | 235 |     |     |     |     | 240 |     |
| CTG | TTC | CAC | ATC | GAC | CTG | AAC | GGT | CAG | CAC | GGC | CCG | AAG | TTC | GAC | CAG | 768 |
| Leu | Phe | His | Ile | Asp | Leu | Asn | Gly | Gln | His | Gly | Pro | Lys | Phe | Asp | Gln |     |
|     |     |     |     | 245 |     |     |     |     | 250 |     |     |     |     | 255 |     |     |
| GAC | CTG | GTC | TTC | GGC | CAC | GGT | GAC | CTG | CTC | AAC | GCG | TTC | TCG | CTG | GTC | 816 |
| Asp | Leu | Val | Phe | Gly | His | Gly | Asp | Leu | Leu | Asn | Ala | Phe | Ser | Leu | Val |     |
|     |     |     | 260 |     |     |     |     | 265 |     |     |     |     | 270 |     |     |     |
| GAC | CTC | CTG | GAG | AAC | GGC | CCG | GAC | GGC | GCC | CCG | GCG | TAC | GAC | GGA | CCC | 864 |
| Asp | Leu | Leu | Glu | Asn | Gly | Pro | Asp | Gly | Ala | Pro | Ala | Tyr | Asp | Gly | Pro |     |
|     |     | 275 |     |     |     |     | 280 |     |     |     |     | 285 |     |     |     |     |
| CGT | CAC | TTC | GAC | TAC | AAG | CCG | TCC | CGT | ACC | GAG | GAC | TAC | GAC | GGC | GTC | 912 |
| Arg | His | Phe | Asp | Tyr | Lys | Pro | Ser | Arg | Thr | Glu | Asp | Tyr | Asp | Gly | Val |     |
|     | 290 |     |     |     |     | 295 |     |     |     |     | 300 |     |     |     |     |     |
| TGG | GAG | TCG | GCG | AAG | GCC | AAC | ATC | CGG | ATG | TAC | CTG | CTG | CTC | AAG | GAG | 960 |
| Trp | Glu | Ser | Ala | Lys | Ala | Asn | Ile | Arg | Met | Tyr | Leu | Leu | Leu | Lys | Glu |     |
| 305 |     |     |     |     | 310 |     |     |     |     | 315 |     |     |     |     | 320 |     |
| CGG | GCC | AAG | GCG | TTC | CGC | GCC | GAC | CCC | GAG | GTG | CAG | GAG | GCG | CTC | GCC | 1008 |
| Arg | Ala | Lys | Ala | Phe | Arg | Ala | Asp | Pro | Glu | Val | Gln | Glu | Ala | Leu | Ala |     |
|     |     |     |     | 325 |     |     |     |     | 330 |     |     |     |     | 335 |     |     |
| GCC | AGC | AAG | GTC | GCG | GAG | CTG | AAG | ACC | CCG | ACC | CTG | AAC | CCG | GGC | GAG | 1056 |
| Ala | Ser | Lys | Val | Ala | Glu | Leu | Lys | Thr | Pro | Thr | Leu | Asn | Pro | Gly | Glu |     |
|     |     |     | 340 |     |     |     |     | 345 |     |     |     |     | 350 |     |     |     |
| GGA | TAC | GCC | GAG | CTG | CTC | GCC | GAC | CGC | AGC | GCG | TTC | GAG | GAC | TAC | GAC | 1104 |
| Gly | Tyr | Ala | Glu | Leu | Leu | Ala | Asp | Arg | Ser | Ala | Phe | Glu | Asp | Tyr | Asp |     |
|     |     | 355 |     |     |     |     | 360 |     |     |     |     | 365 |     |     |     |     |
| GCC | GAC | GCC | GTG | GGC | GCC | AAG | GGC | TTC | GGC | TTC | GTC | AAG | CTG | AAC | CAG | 1152 |
| Ala | Asp | Ala | Val | Gly | Ala | Lys | Gly | Phe | Gly | Phe | Val | Lys | Leu | Asn | Gln |     |
| 370 |     |     |     |     | 375 |     |     |     |     | 380 |     |     |     |     |     |     |

```
            CTC  GCG  ATC  GAG  CAC  CTG  CTC  GGA  GCC  CGC                    1182
            Leu  Ala  Ile  Glu  His  Leu  Leu  Gly  Ala  Arg
            385                 390
```

(2) INFORMATION FOR SEQ ID NO:5:

(i) SEQUENCE CHARACTERISTICS:
        (A) LENGTH: 394 amino acids
        (B) TYPE: amino acid
        (D) TOPOLOGY: linear (ii) MOLECULE TYPE: protein (xi) SEQUENCE DESCRIPTION: SEQ ID NO:5:

```
Val  Ser  Val  Gln  Ala  Thr  Arg  Glu  Asp  Lys  Phe  Ser  Phe  Gly  Leu  Trp
 1                   5                        10                       15

Thr  Val  Gly  Trp  Gln  Ala  Arg  Asp  Ala  Phe  Gly  Asp  Ala  Thr  Arg  Thr
               20                       25                       30

Ala  Leu  Asp  Pro  Val  Glu  Ala  Val  His  Lys  Leu  Ala  Glu  Ile  Gly  Ala
          35                       40                       45

Tyr  Gly  Ile  Thr  Phe  His  Asp  Asp  Leu  Val  Pro  Phe  Gly  Ser  Asp
     50                       55                       60

Ala  Gln  Thr  Arg  Asp  Gly  Ile  Ile  Ala  Gly  Phe  Lys  Lys  Ala  Leu  Asp
 65                      70                       75                       80

Glu  Thr  Gly  Leu  Ile  Val  Pro  Met  Val  Thr  Thr  Asn  Leu  Phe  Thr  His
                    85                       90                       95

Pro  Val  Phe  Lys  Asp  Gly  Phe  Thr  Ser  Asn  Asp  Arg  Ser  Val  Arg
               100                      105                      110

Arg  Tyr  Ala  Ile  Arg  Lys  Val  Leu  Arg  Gln  Met  Asp  Leu  Gly  Ala  Glu
               115                      120                      125

Leu  Gly  Ala  Lys  Thr  Leu  Val  Leu  Trp  Gly  Gly  Arg  Glu  Gly  Ala  Glu
     130                      135                      140

Tyr  Asp  Ser  Ala  Lys  Asp  Val  Ser  Ala  Ala  Leu  Asp  Arg  Tyr  Arg  Glu
145                      150                      155                      160

Ala  Leu  Asn  Leu  Leu  Ala  Gln  Tyr  Ser  Glu  Asp  Arg  Gly  Tyr  Gly  Leu
               165                      170                      175

Arg  Phe  Ala  Ile  Glu  Pro  Lys  Pro  Asn  Glu  Pro  Arg  Gly  Asp  Ile  Leu
               180                      185                      190

Leu  Pro  Thr  Ala  Gly  His  Ala  Ile  Ala  Phe  Val  Gln  Glu  Leu  Glu  Arg
               195                      200                      205

Pro  Glu  Leu  Phe  Gly  Ile  Asn  Pro  Glu  Thr  Gly  His  Glu  Gln  Met  Ser
     210                      215                      220

Asn  Leu  Asn  Phe  Thr  Gln  Gly  Ile  Ala  Gln  Ala  Leu  Trp  His  Lys  Lys
225                      230                      235                      240

Leu  Phe  His  Ile  Asp  Leu  Asn  Gly  Gln  His  Gly  Pro  Lys  Phe  Asp  Gln
               245                      250                      255

Asp  Leu  Val  Phe  Gly  His  Gly  Asp  Leu  Leu  Asn  Ala  Phe  Ser  Leu  Val
               260                      265                      270

Asp  Leu  Leu  Glu  Asn  Gly  Pro  Asp  Gly  Ala  Pro  Ala  Tyr  Asp  Gly  Pro
          275                      280                      285

Arg  His  Phe  Asp  Tyr  Lys  Pro  Ser  Arg  Thr  Glu  Asp  Tyr  Asp  Gly  Val
     290                      295                      300

Trp  Glu  Ser  Ala  Lys  Ala  Asn  Ile  Arg  Met  Tyr  Leu  Leu  Leu  Lys  Glu
305                      310                      315                      320

Arg  Ala  Lys  Ala  Phe  Arg  Ala  Asp  Pro  Glu  Val  Gln  Glu  Ala  Leu  Ala
                    325                      330                      335

Ala  Ser  Lys  Val  Ala  Glu  Leu  Lys  Thr  Pro  Thr  Leu  Asn  Pro  Gly  Glu
               340                      345                      350
```

Gly Tyr Ala Glu Leu Leu Ala Asp Arg Ser Ala Phe Glu Asp Tyr Asp
        355                 360                 365

Ala Asp Ala Val Gly Ala Lys Gly Phe Gly Phe Val Lys Leu Asn Gln
    370                 375                 380

Leu Ala Ile Glu His Leu Leu Gly Ala Arg
385             390

( 2 ) INFORMATION FOR SEQ ID NO:6:

( i ) SEQUENCE CHARACTERISTICS:
        ( A ) LENGTH: 1164 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Streptomyces murinus
        ( B ) STRAIN: DSM 40091

( i x ) FEATURE:
        ( A ) NAME/KEY: CDS
        ( B ) LOCATION: 1..1164
        ( C ) IDENTIFICATION METHOD: experimental
        ( D ) OTHER INFORMATION: /ECnumber=5.3.1.5
            / product="xylose isomerase (glucose isomerase)"
            / evidence=EXPERIMENTAL
            / standardname="D-xylose ketol isomerase"

( x i ) SEQUENCE DESCRIPTION: SEQ ID NO:6:

```
ATG AGC TTC CAG CCC ACC CCC GAG GAC AGG TTC ACC TTC GGT CTG TGG      48
Met Ser Phe Gln Pro Thr Pro Glu Asp Arg Phe Thr Phe Gly Leu Trp
 1           5                  10                  15

ACC GTC GGC TGG CAG GGA AGG GAC CCG TTC GGC GAC GCC ACC CGC CCC      96
Thr Val Gly Trp Gln Gly Arg Asp Pro Phe Gly Asp Ala Thr Arg Pro
             20                  25                  30

GCC CTC GAC CCG GTC GAG ACG GTG CAG CGC CTG GCC GAG CTG GGC GCC     144
Ala Leu Asp Pro Val Glu Thr Val Gln Arg Leu Ala Glu Leu Gly Ala
         35                  40                  45

TAC GGA GTG ACC TTC CAC GAC GAC GAC CTG ATC CCC TTC GGG TCC TCC     192
Tyr Gly Val Thr Phe His Asp Asp Asp Leu Ile Pro Phe Gly Ser Ser
     50                  55                  60

GAC ACC GAG CGC GAG TCG CAC ATC AAG CGC TTC CGC CAG GCC CTG GAC     240
Asp Thr Glu Arg Glu Ser His Ile Lys Arg Phe Arg Gln Ala Leu Asp
 65                  70                  75                  80

GCC ACC GGC ATG ACG GTG CCC ATG GCC ACC ACC AAC CTC TTC ACC CAC     288
Ala Thr Gly Met Thr Val Pro Met Ala Thr Thr Asn Leu Phe Thr His
                 85                  90                  95

CCC GTC TTC AAG GAC GGC GGC TTC ACC GCC AAC GAC CGC GAC GTA CGC     336
Pro Val Phe Lys Asp Gly Gly Phe Thr Ala Asn Asp Arg Asp Val Arg
            100                 105                 110

CGG TAC GCG CTG CGC AAG ACG ATC GGC AAC ATC GAC CTG GCG GCC GAA     384
Arg Tyr Ala Leu Arg Lys Thr Ile Gly Asn Ile Asp Leu Ala Ala Glu
        115                 120                 125

CTG GGT GCC AAG ACG TAT GTC GCC TGG GGC GGC CGT GAG GGC GCC GAG     432
Leu Gly Ala Lys Thr Tyr Val Ala Trp Gly Gly Arg Glu Gly Ala Glu
    130                 135                 140

TCC GGT GGC GCC AAG GAC GTG CGC GAC GCC CTC GAC CGC ATG AAG GAG     480
Ser Gly Gly Ala Lys Asp Val Arg Asp Ala Leu Asp Arg Met Lys Glu
145                 150                 155                 160

GCG TTC GAC CTC CTC GGC GAG TAC GTC ACC GCC CAG GGC TAC GAC CTC     528
Ala Phe Asp Leu Leu Gly Glu Tyr Val Thr Ala Gln Gly Tyr Asp Leu
```

| | | | | | | | | | | | | | | | | |
|---|---|---|---|---|---|---|---|---|---|---|---|---|---|---|---|---|
| | | | | 165 | | | | | 170 | | | | | 175 | | |
| CGC | TTC | GCC | ATC | GAG | CCC | AAG | CCC | AAC | GAG | CCC | CGC | GGC | GAC | ATC | CTG | 576 |
| Arg | Phe | Ala | Ile 180 | Glu | Pro | Lys | Pro | Asn 185 | Glu | Pro | Arg | Gly | Asp 190 | Ile | Leu | |
| CTG | CCC | ACC | GTC | GGC | CAC | GCC | CTG | GCC | TTC | ATC | GAG | CGC | CTG | GAG | CGC | 624 |
| Leu | Pro | Thr 195 | Val | Gly | His | Ala | Leu 200 | Ala | Phe | Ile | Glu | Arg 205 | Leu | Glu | Arg | |
| CCG | GAG | CTG | TAC | GGC | GTC | AAC | CCG | GAG | GTC | GGC | CAC | GAG | CAG | ATG | GCC | 672 |
| Pro | Glu 210 | Leu | Tyr | Gly | Val | Asn 215 | Pro | Glu | Val | Gly | His 220 | Glu | Gln | Met | Ala | |
| GGC | CTG | AAC | TTC | CCG | CAC | GGC | ATC | GCG | CAG | GCC | CTG | TGG | GCG | GGC | AAG | 720 |
| Gly 225 | Leu | Asn | Phe | Pro | His 230 | Gly | Ile | Ala | Gln | Ala 235 | Leu | Trp | Ala | Gly | Lys 240 | |
| CTC | TTC | CAC | ATC | GAC | CTC | AAC | GGC | CAG | TCC | GGC | ATC | AAG | TAC | GAC | CAG | 768 |
| Leu | Phe | His | Ile | Asp 245 | Leu | Asn | Gly | Gln | Ser 250 | Gly | Ile | Lys | Tyr | Asp 255 | Gln | |
| GAC | CTG | CGG | TTC | GGC | GCC | GGC | GAC | CTG | CGG | GCG | GCG | TTC | TGG | CTG | GTC | 816 |
| Asp | Leu | Arg | Phe 260 | Gly | Ala | Gly | Asp | Leu 265 | Arg | Ala | Ala | Phe | Trp 270 | Leu | Val | |
| GAC | CTC | CTG | GAG | ACC | GCC | GGT | TAC | GAG | GGC | CCG | CGG | CAC | TTC | GAC | TTC | 864 |
| Asp | Leu | Leu 275 | Glu | Thr | Ala | Gly | Tyr 280 | Glu | Gly | Pro | Arg | His 285 | Phe | Asp | Phe | |
| AAG | CCG | CCG | CGG | ACC | GAG | GAC | TTC | GAC | GGC | GTG | TGG | GCC | TCG | GCC | GCG | 912 |
| Lys | Pro 290 | Pro | Arg | Thr | Glu | Asp 295 | Phe | Asp | Gly | Val | Trp 300 | Ala | Ser | Ala | Ala | |
| GGC | TGC | ATG | CGC | AAC | TAC | CTG | ATC | CTC | AAG | GAC | CGT | GCG | GCC | GCC | TTC | 960 |
| Gly 305 | Cys | Met | Arg | Asn | Tyr 310 | Leu | Ile | Leu | Lys | Asp 315 | Arg | Ala | Ala | Ala | Phe 320 | |
| CGT | GCC | GAC | CCG | GAG | GTG | CAG | GAG | GCG | CTG | CGT | GCC | GCG | CGT | CTG | GAC | 1008 |
| Arg | Ala | Asp | Pro | Glu 325 | Val | Gln | Glu | Ala | Leu 330 | Arg | Ala | Ala | Arg | Leu 335 | Asp | |
| CAG | CTG | GCC | CAG | CCG | ACC | GCG | GCC | GAC | GGC | CTT | GAC | GCC | CTG | CTC | GCC | 1056 |
| Gln | Leu | Ala | Gln 340 | Pro | Thr | Ala | Ala | Asp 345 | Gly | Leu | Asp | Ala | Leu 350 | Leu | Ala | |
| GAC | CGC | GCG | GCG | TTC | GAG | GAC | TTC | GAC | GTC | GAT | GCC | GCC | GCC | GCG | CGC | 1104 |
| Asp | Arg | Ala 355 | Ala | Phe | Glu | Asp | Phe 360 | Asp | Val | Asp | Ala | Ala 365 | Ala | Ala | Arg | |
| GGT | ATG | GCG | TTC | GAG | CAC | CTC | GAC | CAG | CTG | GCG | ATG | GAC | CAC | CTG | CTG | 1152 |
| Gly | Met 370 | Ala | Phe | Glu | His | Leu 375 | Asp | Gln | Leu | Ala | Met 380 | Asp | His | Leu | Leu | |
| GGC | GCG | CGC | GGC | | | | | | | | | | | | | 1164 |
| Gly | Ala | Arg | Gly 385 | | | | | | | | | | | | | |

( 2 ) INFORMATION FOR SEQ ID NO:7:

( i ) SEQUENCE CHARACTERISTICS:
        ( A ) LENGTH: 388 amino acids
        ( B ) TYPE: amino acid
        ( D ) TOPOLOGY: linear ( i i ) MOLECULE TYPE: protein ( x i ) SEQUENCE DESCRIPTION: SEQ ID NO:7:

| | | | | | | | | | | | | | | | |
|---|---|---|---|---|---|---|---|---|---|---|---|---|---|---|---|
| Met 1 | Ser | Phe | Gln | Pro 5 | Thr | Pro | Glu | Asp | Arg 10 | Phe | Thr | Phe | Gly | Leu 15 | Trp |
| Thr | Val | Gly | Trp 20 | Gln | Gly | Arg | Asp | Pro 25 | Phe | Gly | Asp | Ala | Thr 30 | Arg | Pro |
| Ala | Leu | Asp 35 | Pro | Val | Glu | Thr | Val 40 | Gln | Arg | Leu | Ala | Glu 45 | Leu | Gly | Ala |
| Tyr | Gly 50 | Val | Thr | Phe | His | Asp 55 | Asp | Asp | Leu | Ile | Pro 60 | Phe | Gly | Ser | Ser |

```
Asp Thr Glu Arg Glu Ser His Ile Lys Arg Phe Arg Gln Ala Leu Asp
 65              70                  75                  80

Ala Thr Gly Met Thr Val Pro Met Ala Thr Thr Asn Leu Phe Thr His
                 85              90                      95

Pro Val Phe Lys Asp Gly Gly Phe Thr Ala Asn Asp Arg Asp Val Arg
             100             105                 110

Arg Tyr Ala Leu Arg Lys Thr Ile Gly Asn Ile Asp Leu Ala Ala Glu
         115             120                 125

Leu Gly Ala Lys Thr Tyr Val Ala Trp Gly Gly Arg Glu Gly Ala Glu
     130             135                 140

Ser Gly Gly Ala Lys Asp Val Arg Asp Ala Leu Asp Arg Met Lys Glu
145                 150             155                     160

Ala Phe Asp Leu Leu Gly Glu Tyr Val Thr Ala Gln Gly Tyr Asp Leu
                 165             170                 175

Arg Phe Ala Ile Glu Pro Lys Pro Asn Glu Pro Arg Gly Asp Ile Leu
             180             185                 190

Leu Pro Thr Val Gly His Ala Leu Ala Phe Ile Glu Arg Leu Glu Arg
             195             200             205

Pro Glu Leu Tyr Gly Val Asn Pro Glu Val Gly His Glu Gln Met Ala
     210             215             220

Gly Leu Asn Phe Pro His Gly Ile Ala Gln Ala Leu Trp Ala Gly Lys
225             230                 235                     240

Leu Phe His Ile Asp Leu Asn Gly Gln Ser Gly Ile Lys Tyr Asp Gln
             245             250             255

Asp Leu Arg Phe Gly Ala Gly Asp Leu Arg Ala Ala Phe Trp Leu Val
             260             265             270

Asp Leu Leu Glu Thr Ala Gly Tyr Glu Gly Pro Arg His Phe Asp Phe
         275             280             285

Lys Pro Pro Arg Thr Glu Asp Phe Asp Gly Val Trp Ala Ser Ala Ala
     290             295             300

Gly Cys Met Arg Asn Tyr Leu Ile Leu Lys Asp Arg Ala Ala Ala Phe
305             310             315                     320

Arg Ala Asp Pro Glu Val Gln Glu Ala Leu Arg Ala Ala Arg Leu Asp
             325             330             335

Gln Leu Ala Gln Pro Thr Ala Ala Asp Gly Leu Asp Ala Leu Leu Ala
         340             345             350

Asp Arg Ala Ala Phe Glu Asp Phe Asp Val Asp Ala Ala Ala Ala Arg
         355             360             365

Gly Met Ala Phe Glu His Leu Asp Gln Leu Ala Met Asp His Leu Leu
     370             375             380

Gly Ala Arg Gly
385
```

( 2 ) INFORMATION FOR SEQ ID NO:8:

( i ) SEQUENCE CHARACTERISTICS:
        ( A ) LENGTH: 394 amino acids
        ( B ) TYPE: amino acid
        ( D ) TOPOLOGY: linear ( i i ) MOLECULE TYPE: protein ( i i i ) HYPOTHETICAL: NO ( v i ) ORIGINAL SOURCE:
        ( A ) ORGANISM: Ampullariella species
        ( B ) STRAIN: ATCC 31351

( i x ) FEATURE:
        ( A ) NAME/KEY: Protein
        ( B ) LOCATION: 1..394

( x ) PUBLICATION INFORMATION:
  ( A ) AUTHORS: Saari, J
  ( C ) JOURNAL: J. Bacteriol.
  ( D ) VOLUME: 169
  ( F ) PAGES: 612-
  ( G ) DATE: 1987

( x i ) SEQUENCE DESCRIPTION: SEQ ID NO:8:

| Met | Ser | Leu | Gln | Ala | Thr | Pro | Asp | Asp | Lys | Phe | Ser | Phe | Gly | Leu | Trp |
| 1 | | | | 5 | | | | | 10 | | | | | 15 | |

| Thr | Val | Gly | Trp | Gln | Ala | Arg | Asp | Ala | Phe | Gly | Asp | Ala | Thr | Arg | Pro |
| | | | 20 | | | | | 25 | | | | | 30 | | |

| Val | Leu | Asp | Pro | Ile | Glu | Ala | Val | His | Lys | Leu | Ala | Glu | Ile | Gly | Ala |
| | | 35 | | | | | 40 | | | | | 45 | | | |

| Tyr | Gly | Val | Thr | Phe | His | Asp | Asp | Leu | Val | Pro | Phe | Gly | Ala | Asp |
| | 50 | | | | | 55 | | | | 60 | | | | |

| Ala | Ala | Thr | Arg | Asp | Gly | Ile | Val | Ala | Gly | Phe | Ser | Lys | Ala | Leu | Asp |
| 65 | | | | | 70 | | | | | 75 | | | | | 80 |

| Glu | Thr | Gly | Leu | Ile | Val | Pro | Met | Val | Thr | Thr | Asn | Leu | Phe | Thr | His |
| | | | | 85 | | | | | 90 | | | | | 95 | |

| Pro | Val | Phe | Lys | Asp | Gly | Gly | Phe | Thr | Ser | Asn | Asp | Arg | Ser | Val | Arg |
| | | | 100 | | | | | 105 | | | | | 110 | | |

| Arg | Tyr | Ala | Ile | Arg | Lys | Val | Leu | Arg | Gln | Met | Asp | Leu | Gly | Ala | Glu |
| | | | 115 | | | | 120 | | | | | 125 | | | |

| Leu | Gly | Ala | Lys | Thr | Leu | Val | Leu | Trp | Gly | Gly | Arg | Glu | Gly | Ala | Glu |
| | 130 | | | | | 135 | | | | | 140 | | | | |

| Tyr | Asp | Ser | Ala | Lys | Asp | Val | Gly | Ala | Ala | Leu | Asp | Arg | Tyr | Arg | Glu |
| 145 | | | | | 150 | | | | | 155 | | | | | 160 |

| Ala | Leu | Asn | Leu | Leu | Ala | Gln | Tyr | Ser | Glu | Asp | Gln | Gly | Tyr | Gly | Leu |
| | | | | 165 | | | | | 170 | | | | | 175 | |

| Pro | Phe | Ala | Ile | Glu | Pro | Lys | Pro | Asn | Glu | Pro | Arg | Gly | Asp | Ile | Leu |
| | | | 180 | | | | | 185 | | | | | 190 | | |

| Leu | Pro | Thr | Ala | Gly | His | Ala | Ile | Ala | Phe | Val | Gln | Glu | Leu | Glu | Arg |
| | | | 195 | | | | | 200 | | | | | 205 | | |

| Pro | Glu | Leu | Phe | Gly | Ile | Asn | Pro | Glu | Thr | Gly | His | Glu | Gln | Met | Ser |
| | 210 | | | | | 215 | | | | | 220 | | | | |

| Asn | Leu | Asn | Phe | Thr | Gln | Gly | Ile | Ala | Gln | Ala | Leu | Trp | His | Lys | Lys |
| 225 | | | | | 230 | | | | | 235 | | | | | 240 |

| Leu | Phe | His | Ile | Asp | Leu | Asn | Gly | Gln | His | Gly | Pro | Lys | Phe | Asp | Gln |
| | | | | 245 | | | | | 250 | | | | | 255 | |

| Asp | Leu | Val | Phe | Gly | His | Gly | Asp | Leu | Leu | Asn | Ala | Phe | Ser | Leu | Val |
| | | | 260 | | | | | 265 | | | | | 270 | | |

| Asp | Leu | Leu | Glu | Asn | Gly | Pro | Asp | Gly | Gly | Pro | Ala | Tyr | Asp | Gly | Pro |
| | | 275 | | | | | 280 | | | | | 285 | | | |

| Arg | His | Phe | Asp | Tyr | Lys | Pro | Ser | Arg | Thr | Glu | Asp | Phe | Asp | Gly | Val |
| | 290 | | | | | 295 | | | | | 300 | | | | |

| Trp | Glu | Ser | Ala | Lys | Asp | Asn | Ile | Arg | Met | Tyr | Leu | Leu | Leu | Lys | Glu |
| 305 | | | | | 310 | | | | | 315 | | | | | 320 |

| Arg | Ala | Lys | Ala | Phe | Arg | Ala | Asp | Pro | Glu | Val | Gln | Ala | Ala | Leu | Ala |
| | | | | 325 | | | | | 330 | | | | | 335 | |

| Glu | Ser | Lys | Val | Asp | Glu | Leu | Arg | Thr | Pro | Thr | Leu | Asn | Pro | Gly | Glu |
| | | | 340 | | | | | 345 | | | | | 350 | | |

| Thr | Tyr | Ala | Asp | Leu | Leu | Ala | Asp | Arg | Ser | Ala | Phe | Glu | Asp | Tyr | Asp |
| | | 355 | | | | | 360 | | | | | 365 | | | |

| Ala | Asp | Ala | Val | Gly | Ala | Lys | Gly | Tyr | Gly | Phe | Val | Lys | Leu | Asn | Gln |
| 370 | | | | | 375 | | | | | 380 | | | | | |

Leu Ala Ile Asp His Leu Leu Gly Ala Arg
385                 390

(2) INFORMATION FOR SEQ ID NO:9:

(i) SEQUENCE CHARACTERISTICS:
        (A) LENGTH: 395 amino acids
        (B) TYPE: amino acid
        (D) TOPOLOGY: linear (ii) MOLECULE TYPE: protein (vi) ORIGINAL SOURCE:
        (A) ORGANISM: Arthrobacter species (ix) FEATURE:
        (A) NAME/KEY: Protein
        (B) LOCATION: 1..395

(xi) SEQUENCE DESCRIPTION: SEQ ID NO:9:

```
Met Ser Val Gln Pro Thr Pro Ala Asp His Phe Thr Phe Gly Leu Trp
 1               5                  10                  15

Thr Val Gly Trp Thr Gly Ala Asp Pro Phe Gly Val Ala Thr Arg Lys
                20                  25                  30

Asn Leu Asp Pro Val Glu Ala Val His Lys Leu Ala Glu Leu Gly Ala
             35                  40                  45

Tyr Gly Ile Thr Phe His Asp Asn Asp Leu Ile Pro Phe Asp Ala Thr
     50                  55                  60

Glu Ala Glu Arg Glu Lys Ile Leu Gly Asp Phe Asn Gln Ala Leu Lys
65                  70                  75                  80

Asp Thr Gly Leu Lys Val Pro Met Val Thr Thr Asn Leu Phe Ser His
                 85                  90                  95

Pro Val Phe Lys Asp Gly Phe Thr Ser Asn Asp Arg Ser Ile Arg
                100                 105                 110

Arg Phe Ala Leu Ala Lys Val Leu His Asn Ile Asp Leu Ala Ala Glu
             115                 120                 125

Met Gly Ala Glu Thr Phe Val Met Trp Gly Gly Arg Glu Gly Ser Glu
    130                 135                 140

Tyr Asp Gly Ser Lys Asp Leu Ala Ala Ala Leu Asp Arg Met Arg Glu
145                 150                 155                 160

Gly Val Asp Thr Ala Ala Gly Tyr Ile Lys Asp Lys Gly Tyr Asn Leu
                165                 170                 175

Arg Ile Ala Leu Glu Pro Lys Pro Asn Glu Pro Arg Gly Asp Ile Phe
            180                 185                 190

Leu Pro Thr Val Gly His Gly Leu Ala Phe Ile Glu Gln Leu Glu His
    195                 200                 205

Gly Asp Ile Val Gly Leu Asn Pro Glu Thr Gly His Glu Gln Met Ala
210                 215                 220

Gly Leu Asn Phe Thr His Gly Ile Ala Gln Ala Leu Trp Ala Glu Lys
225                 230                 235                 240

Leu Phe His Ile Asp Leu Asn Gly Gln Arg Gly Ile Lys Tyr Asp Gln
            245                 250                 255

Asp Leu Val Phe Gly His Gly Asp Leu Thr Ser Ala Phe Phe Thr Val
            260                 265                 270

Asp Leu Leu Glu Asn Gly Phe Pro Asn Gly Gly Pro Lys Tyr Thr Gly
    275                 280                 285

Pro Arg His Phe Asp Tyr Lys Pro Ser Arg Thr Asp Gly Tyr Asp Gly
    290                 295                 300

Val Trp Asp Ser Ala Lys Ala Asn Met Ser Met Tyr Leu Leu Leu Lys
305                 310                 315                 320
```

```
Glu  Arg  Ala  Leu  Ala  Phe  Arg  Ala  Asp  Pro  Glu  Val  Gln  Glu  Ala  Met
               325                      330                      335

Lys  Thr  Ser  Gly  Val  Phe  Glu  Leu  Gly  Glu  Thr  Thr  Leu  Asn  Ala  Gly
               340                      345                      350

Glu  Ser  Ala  Ala  Asp  Leu  Met  Asn  Asp  Ser  Ala  Ser  Phe  Ala  Gly  Phe
               355                      360                      365

Asp  Ala  Glu  Ala  Ala  Ala  Glu  Arg  Asn  Phe  Ala  Phe  Ile  Arg  Leu  Asn
               370                      375                      380

Gln  Leu  Ala  Ile  Glu  His  Leu  Leu  Gly  Ser  Arg
385                      390                      395
```

( 2 ) INFORMATION FOR SEQ ID NO:10:

( i ) SEQUENCE CHARACTERISTICS:
        ( A ) LENGTH: 347 amino acids
        ( B ) TYPE: amino acid
        ( D ) TOPOLOGY: linear ( i i ) MOLECULE TYPE: protein ( v i ) ORIGINAL SOURCE:
        ( A ) ORGANISM: Streptomyces thermovulgaris
        ( B ) STRAIN: DSM 40444

( i x ) FEATURE:
        ( A ) NAME/KEY: Protein
        ( B ) LOCATION: 1..347
        ( D ) OTHER INFORMATION: /note="The C-terminal region of
            this protein is not complete."

( x i ) SEQUENCE DESCRIPTION: SEQ ID NO:10:

```
Met  Ser  Tyr  Gln  Pro  Thr  Pro  Glu  Asp  Arg  Phe  Ser  Phe  Gly  Leu  Trp
1                   5                        10                       15

Thr  Val  Gly  Trp  Gln  Gly  Arg  Asp  Pro  Phe  Gly  Asp  Ala  Thr  Arg  Arg
               20                       25                       30

Pro  Leu  Asp  Pro  Val  Gly  Thr  Val  Gln  Arg  Leu  Ala  Glu  Leu  Gly  Ala
               35                       40                       45

Tyr  Gly  Val  Thr  Phe  His  Asp  Asp  Leu  Ile  Pro  Phe  Gly  Ala  Ser
     50                       55                       60

Glu  Ala  Glu  Arg  Glu  Ala  His  Val  Lys  Arg  Phe  Arg  Gln  Ala  Leu  Asp
65                       70                       75                       80

Ala  Thr  Gly  Met  Thr  Val  Pro  Met  Ala  Thr  Thr  Asn  Leu  Phe  Thr  His
                    85                       90                       95

Pro  Val  Phe  Lys  Asp  Gly  Ala  Phe  Thr  Ala  Asn  Asp  Arg  Asp  Val  Arg
               100                      105                      110

Arg  Tyr  Ala  Leu  Arg  Lys  Thr  Ile  Arg  Asn  Ile  Asp  Leu  Ala  Val  Glu
               115                      120                      125

Leu  Gly  Ala  Arg  Thr  Tyr  Val  Ala  Trp  Gly  Gly  Arg  Glu  Gly  Ala  Glu
     130                      135                      140

Ser  Gly  Ala  Ala  Lys  Asp  Val  Arg  Ala  Ala  Leu  Asp  Arg  Met  Lys  Glu
145                      150                      155                      160

Ala  Phe  Asp  Leu  Leu  Gly  Glu  Tyr  Val  Thr  Ser  Gln  Gly  Tyr  Asp  Ile
               165                      170                      175

Arg  Phe  Ala  Ile  Glu  Pro  Lys  Pro  Asn  Glu  Pro  Arg  Gly  Asp  Ile  Leu
               180                      185                      190

Leu  Pro  Thr  Val  Gly  His  Ala  Leu  Ala  Phe  Ile  Glu  Arg  Leu  Glu  Arg
               195                      200                      205

Pro  Glu  Leu  Phe  Gly  Val  Asn  Pro  Glu  Val  Gly  His  Glu  Gln  Met  Ala
     210                      215                      220

Gly  Leu  Asn  Phe  Pro  His  Gly  Ile  Ala  Gln  Ala  Leu  Trp  Ala  Gly  Lys
225                      230                      235                      240
```

-continued

```
Leu Phe His Ile Asp Leu Asn Gly Gln Ser Gly Ile Lys Tyr Asp Gln
            245             250                 255

Asp Leu Arg Phe Gly Ala Gly Asp Leu Arg Ala Ala Phe Trp Leu Val
            260             265                 270

Asp Leu Leu Glu Ser Ser Gly Tyr Asp Gly Pro Arg His Phe Asp Phe
            275             280                 285

Lys Pro Pro Arg Thr Glu Asp Leu Asp Gly Val Trp Ala Ser Ala Ala
            290             295                 300

Gly Cys Met Arg Asn Tyr Leu Ile Leu Lys Glu Arg Ser Ala Ala Phe
305             310             315                         320

Arg Ala Asp Pro Glu Val Gln Glu Ala Leu Arg Ala Ser Arg Leu Asp
            325             330                 335

Gln Leu Ala Gln Pro Thr Ala Ala Asp Gly Leu
            340             345
```

( 2 ) INFORMATION FOR SEQ ID NO:11:

( i ) SEQUENCE CHARACTERISTICS:
( A ) LENGTH: 389 amino acids
( B ) TYPE: amino acid
( C ) STRANDEDNESS: single
( D ) TOPOLOGY: linear ( i i ) MOLECULE TYPE: protein ( i i i ) HYPOTHETICAL: NO ( v i ) ORIGINAL SOURCE:
( A ) ORGANISM: Streptomyces violaceoniger
( B ) STRAIN: CBS 409.73

( i x ) FEATURE:
( A ) NAME/KEY: Protein
( B ) LOCATION: 1..389

( x ) PUBLICATION INFORMATION:
( A ) AUTHORS: Tiraby,
( C ) JOURNAL: Nucleic Acids Res.
( D ) VOLUME: 16
( F ) PAGES: 9337-
( G ) DATE: 1988

( x i ) SEQUENCE DESCRIPTION: SEQ ID NO:11:

```
Met Ser Phe Gln Pro Thr Pro Glu Asp Lys Phe Thr Phe Gly Leu Trp
1               5                   10                  15

Thr Val Gly Trp Gln Gly Arg Asp Pro Phe Gly Asp Ala Thr Arg Pro
                20                  25                  30

Ala Leu Asp Pro Val Glu Thr Val Gln Arg Leu Ala Glu Leu Gly Ala
            35              40                  45

Tyr Gly Val Thr Phe His Asp Asp Leu Ile Pro Phe Gly Ser Ser
    50              55                  60

Asp Thr Glu Arg Glu Ser His Ile Lys Arg Phe Arg Gln Ala Leu Asp
65              70                  75                          80

Ala Thr Gly Met Thr Val Pro Met Ala Thr Thr Asn Leu Phe Thr His
                85              90                  95

Pro Val Phe Lys Asp Gly Gly Phe Thr Ala Asn Asp Arg Asp Val Arg
            100             105                 110

Arg Tyr Ala Leu Arg Lys Thr Ile Arg Asn Ile Asp Leu Ala Ala Glu
            115             120                 125

Leu Gly Ala Lys Thr Tyr Val Ala Trp Gly Gly Arg Glu Gly Ala Glu
            130             135                 140

Ser Gly Gly Ala Lys Asp Val Arg Asp Ala Leu Asp Arg Met Lys Glu
145             150                 155                     160

Ala Phe Asp Leu Leu Gly Glu Tyr Val Thr Ala Gln Gly Tyr Asp Leu
```

|  |  |  |  |  | 165 |  |  |  | 170 |  |  |  | 175 |  |
|---|---|---|---|---|---|---|---|---|---|---|---|---|---|---|
| Arg | Phe | Ala | Ile | Glu | Pro | Lys | Pro | Asn | Glu | Pro | Arg | Gly | Asp | Ile | Leu |
|  |  |  | 180 |  |  |  |  | 185 |  |  |  | 190 |  |  |
| Leu | Pro | Thr | Val | Gly | His | Ala | Leu | Ala | Phe | Ile | Glu | Arg | Leu | Glu | Arg |
|  |  | 195 |  |  |  |  | 200 |  |  |  |  | 205 |  |  |  |
| Pro | Glu | Leu | Tyr | Gly | Val | Asn | Pro | Glu | Val | Gly | His | Glu | Gln | Met | Ala |
|  | 210 |  |  |  |  | 215 |  |  |  |  | 220 |  |  |  |  |
| Gly | Leu | Asn | Phe | Pro | His | Gly | Ile | Ala | Gln | Ala | Leu | Trp | Ala | Gly | Lys |
| 225 |  |  |  |  | 230 |  |  |  | 235 |  |  |  |  |  | 240 |
| Leu | Phe | His | Ile | Asp | Leu | Asn | Gly | Gln | Ser | Gly | Ile | Lys | Tyr | Asp | Gln |
|  |  |  |  | 245 |  |  |  |  | 250 |  |  |  |  | 255 |  |
| Asp | Leu | Arg | Phe | Gly | Ala | Gly | Asp | Leu | Arg | Ala | Ala | Phe | Trp | Leu | Val |
|  |  |  | 260 |  |  |  |  |  | 265 |  |  |  | 270 |  |  |
| Asp | Leu | Leu | Glu | Ser | Ala | Gly | Tyr | Glu | Gly | Pro | Arg | His | Phe | Asp | Phe |
|  |  | 275 |  |  |  |  |  | 280 |  |  |  | 285 |  |  |  |
| Lys | Pro | Pro | Arg | Thr | Glu | Asp | Phe | Asp | Gly | Val | Trp | Ala | Ser | Ala | Glu |
|  | 290 |  |  |  |  | 295 |  |  |  |  | 300 |  |  |  |  |
| Gly | Cys | Met | Arg | Asn | Tyr | Leu | Ile | Leu | Lys | Glu | Arg | Ala | Ala | Ala | Phe |
| 305 |  |  |  |  | 310 |  |  |  |  | 315 |  |  |  |  | 320 |
| Arg | Ala | Asp | Pro | Glu | Val | Gln | Glu | Ala | Leu | Arg | Ala | Ala | Arg | Leu | Asp |
|  |  |  |  | 325 |  |  |  |  | 330 |  |  |  |  | 335 |  |
| Gln | Leu | Ala | Gln | Pro | Thr | Ala | Ala | Asp | Gly | Leu | Glu | Ala | Leu | Leu | Ala |
|  |  |  | 340 |  |  |  |  | 345 |  |  |  |  | 350 |  |  |
| Asp | Arg | Thr | Ala | Phe | Glu | Asp | Phe | Asp | Val | Glu | Ala | Ala | Ala | Ala | Arg |
|  |  | 355 |  |  |  |  | 360 |  |  |  |  |  | 365 |  |  |
| Ala | Ala | Trp | Pro | Phe | Glu | Arg | Leu | Asp | Gln | Leu | Ala | Met | Asp | His | Leu |
|  | 370 |  |  |  |  |  | 375 |  |  |  | 380 |  |  |  |  |
| Leu | Gly | Ala | Arg | Gly |  |  |  |  |  |  |  |  |  |  |  |
| 385 |  |  |  |  |  |  |  |  |  |  |  |  |  |  |  |

( 2 ) INFORMATION FOR SEQ ID NO:12:

( i ) SEQUENCE CHARACTERISTICS:
        ( A ) LENGTH: 387 amino acids
        ( B ) TYPE: amino acid
        ( D ) TOPOLOGY: linear ( i i ) MOLECULE TYPE: protein ( v i ) ORIGINAL SOURCE:
        ( A ) ORGANISM: Streptomyces violaceoruber
        ( B ) STRAIN: LMG 7183

( i x ) FEATURE:
        ( A ) NAME/KEY: Protein
        ( B ) LOCATION: 1..387

( x i ) SEQUENCE DESCRIPTION: SEQ ID NO:12:

| Met | Asn | Tyr | Gln | Pro | Thr | Pro | Glu | Asp | Arg | Phe | Thr | Phe | Gly | Leu | Trp |
|---|---|---|---|---|---|---|---|---|---|---|---|---|---|---|---|
| 1 |  |  |  | 5 |  |  |  |  | 10 |  |  |  |  | 15 |  |
| Thr | Val | Gly | Trp | Gln | Gly | Arg | Asp | Pro | Phe | Gly | Asp | Ala | Thr | Arg | Gln |
|  |  |  | 20 |  |  |  |  | 25 |  |  |  |  | 30 |  |  |
| Ala | Leu | Asp | Pro | Ala | Glu | Ser | Val | Arg | Arg | Leu | Ser | Glu | Leu | Gly | Ala |
|  |  | 35 |  |  |  |  | 40 |  |  |  |  | 45 |  |  |  |
| Tyr | Gly | Val | Thr | Phe | His | Asp | Asp | Asp | Leu | Ile | Pro | Phe | Gly | Ser | Ser |
|  | 50 |  |  |  |  | 55 |  |  |  |  | 60 |  |  |  |  |
| Asp | Thr | Glu | Arg | Glu | Ser | His | Ile | Lys | Arg | Phe | Arg | Gln | Ala | Leu | Asp |
| 65 |  |  |  |  | 70 |  |  |  |  | 75 |  |  |  |  | 80 |
| Ala | Thr | Gly | Met | Lys | Val | Pro | Met | Ala | Thr | Thr | Asn | Leu | Phe | Thr | His |
|  |  |  |  | 85 |  |  |  |  | 90 |  |  |  |  | 95 |  |

|     |     |     |     |     |     |     |     |     |     |     |     |     |     |     |
|-----|-----|-----|-----|-----|-----|-----|-----|-----|-----|-----|-----|-----|-----|-----|
| Pro | Val | Phe | Lys<br>100 | Asp | Gly | Ala | Phe | Thr<br>105 | Ala | Asn | Asp | Arg<br>110 | Asp | Val | Arg |
| Arg | Tyr | Ala<br>115 | Leu | Arg | Lys | Thr | Ile<br>120 | Arg | Asn | Ile | Asp<br>125 | Leu | Ala | Val | Glu |
| Leu | Gly<br>130 | Ala | Ser | Val | Tyr<br>135 | Val | Ala | Trp | Gly | Gly<br>140 | Arg | Glu | Gly | Ala | Glu |
| Ser<br>145 | Gly | Ala | Ala | Lys<br>150 | Asp | Val | Arg | Asp | Ala<br>155 | Leu | Asp | Arg | Met | Lys | Glu<br>160 |
| Ala | Phe | Asp | Leu | Leu<br>165 | Gly | Glu | Tyr | Val | Thr<br>170 | Glu | Gln | Gly | Tyr | Asp<br>175 | Leu |
| Lys | Phe | Ala | Ile<br>180 | Glu | Pro | Lys | Pro | Asn<br>185 | Glu | Pro | Arg | Gly | Asp<br>190 | Ile | Leu |
| Leu | Pro | Thr<br>195 | Val | Gly | His | Ala | Leu<br>200 | Ala | Phe | Ile | Glu | Arg<br>205 | Leu | Glu | Arg |
| Pro | Glu<br>210 | Leu | Tyr | Gly | Val | Asn<br>215 | Pro | Glu | Val | Gly | His<br>220 | Glu | Gln | Met | Ala |
| Gly<br>225 | Leu | Asn | Phe | Pro | His<br>230 | Gly | Ile | Ala | Gln | Ala<br>235 | Leu | Trp | Ala | Gly | Lys<br>240 |
| Leu | Phe | His | Ile | Asp<br>245 | Leu | Asn | Gly | Gln | Ser<br>250 | Gly | Ile | Lys | Tyr | Asp<br>255 | Gln |
| Asp | Leu | Arg | Phe<br>260 | Gly | Ala | Gly | Asp | Leu<br>265 | Arg | Ala | Ala | Phe | Trp<br>270 | Leu | Val |
| Asp | Leu | Leu<br>275 | Glu | Arg | Ala | Gly | Tyr<br>280 | Ala | Gly | Pro | Arg | His<br>285 | Phe | Asp | Phe |
| Lys | Pro<br>290 | Pro | Arg | Thr | Glu | Asp<br>295 | Phe | Asp | Gly | Val | Trp<br>300 | Ala | Ser | Ala | Ala |
| Gly<br>305 | Cys | Met | Arg | Asn | Tyr<br>310 | Leu | Ile | Leu | Lys | Asp<br>315 | Arg | Ala | Ala | Ala | Phe<br>320 |
| Arg | Ala | Asp | Pro | Gln<br>325 | Val | Gln | Glu | Ala | Leu<br>330 | Ala | Ala | Ala | Arg | Leu<br>335 | Asp |
| Glu | Leu | Ala | Arg<br>340 | Pro | Thr | Ala | Glu | Asp<br>345 | Gly | Leu | Ala | Ala | Leu<br>350 | Leu | Ala |
| Asp | Arg | Ser<br>355 | Ala | Tyr | Asp | Thr | Phe<br>360 | Asp | Val | Asp | Ala | Ala<br>365 | Ala | Ala | Arg |
| Gly | Met<br>370 | Ala | Phe | Glu | His | Leu<br>375 | Asp | Gln | Leu | Ala | Met<br>380 | Asp | His | Leu | Leu |
| Gly<br>385 | Ala | Arg |

( 2 ) INFORMATION FOR SEQ ID NO:13:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( x i ) SEQUENCE DESCRIPTION: SEQ ID NO:13:

GGACAGACAT GGTTACC     17

( 2 ) INFORMATION FOR SEQ ID NO:14:

( i ) SEQUENCE CHARACTERISTICS:
( A ) LENGTH: 14 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( x i ) SEQUENCE DESCRIPTION: SEQ ID NO:14:

CGAAGGGTAC CAGG                                                                14

( 2 ) INFORMATION FOR SEQ ID NO:15:

( i ) SEQUENCE CHARACTERISTICS:
 ( A ) LENGTH: 19 base pairs
 ( B ) TYPE: nucleic acid
 ( C ) STRANDEDNESS: single
 ( D ) TOPOLOGY: linear ( i i ) MOLECULE TYPE: cDNA ( i i i ) HYPOTHETICAL: NO ( x i ) SEQUENCE DESCRIPTION: SEQ ID NO:15:

GCCGTTCTCG AGGAGGTCG                                                           19

( 2 ) INFORMATION FOR SEQ ID NO:16:

( i ) SEQUENCE CHARACTERISTICS:
 ( A ) LENGTH: 20 base pairs
 ( B ) TYPE: nucleic acid
 ( C ) STRANDEDNESS: single
 ( D ) TOPOLOGY: linear ( i i ) MOLECULE TYPE: cDNA ( i i i ) HYPOTHETICAL: NO ( x i ) SEQUENCE DESCRIPTION: SEQ ID NO:16:

CCTGGTCGAA CTGCGGGCCG                                                          20

( 2 ) INFORMATION FOR SEQ ID NO:17:

( i ) SEQUENCE CHARACTERISTICS:
 ( A ) LENGTH: 20 base pairs
 ( B ) TYPE: nucleic acid
 ( C ) STRANDEDNESS: single
 ( D ) TOPOLOGY: linear ( i i ) MOLECULE TYPE: cDNA ( i i i ) HYPOTHETICAL: NO ( x i ) SEQUENCE DESCRIPTION: SEQ ID NO:17:

CCTGGTCGAA CCGCGGGCCG                                                          20

( 2 ) INFORMATION FOR SEQ ID NO:18:

( i ) SEQUENCE CHARACTERISTICS:
 ( A ) LENGTH: 20 base pairs
 ( B ) TYPE: nucleic acid
 ( C ) STRANDEDNESS: single
 ( D ) TOPOLOGY: linear ( i i ) MOLECULE TYPE: cDNA ( i i i ) HYPOTHETICAL: NO ( x i ) SEQUENCE DESCRIPTION: SEQ ID NO:18:

CCGCCGTCCC GGAACACCGG                                                          20

( 2 ) INFORMATION FOR SEQ ID NO:19:

( i ) SEQUENCE CHARACTERISTICS:
 ( A ) LENGTH: 20 base pairs (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO:19:

GGGACGGCCG GTAGTCGAAG                                           20

(2) INFORMATION FOR SEQ ID NO:20:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO:20:

GCCTTCTTGA AGGTCGAGAT GATGGAGTCG CGG                             33

(2) INFORMATION FOR SEQ ID NO:21:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO:21:

AGGTCCTGGT CGAACCGCGG GCCGTGCTGG                                 30

(2) INFORMATION FOR SEQ ID NO:22:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO:22:

GGTCCTGGTC GTACCGGATG CCGGACTGG                                  29